(12) United States Patent
Kosaka et al.

(10) Patent No.: US 9,103,816 B2
(45) Date of Patent: Aug. 11, 2015

(54) BLOOD SAMPLE ANALYZING APPARATUS, BLOOD SAMPLE COAGULATION DETERMINING APPARATUS, BLOOD SAMPLE COAGULATION DETERMINING METHOD AND COMPUTER PROGRAM PRODUCT

(75) Inventors: Tokihiro Kosaka, Kakogawa (JP); Koichi Okubo, Kobe (JP)

(73) Assignee: Sysmex Corporation (JP)

(*) Notice: Subject to any disclaimer, the term of this patent is extended or adjusted under 35 U.S.C. 154(b) by 741 days.

(21) Appl. No.: 12/460,657

(22) Filed: Jul. 21, 2009

(65) Prior Publication Data

US 2010/0027868 A1   Feb. 4, 2010

(30) Foreign Application Priority Data

Aug. 1, 2008 (JP) ................... 2008-200177
Aug. 1, 2008 (JP) ................... 2008-200178

(51) Int. Cl.
*A61B 5/00* (2006.01)
*G01N 33/49* (2006.01)
*G01N 35/10* (2006.01)
*G01N 1/28* (2006.01)

(52) U.S. Cl.
CPC ........ *G01N 33/4905* (2013.01); *G01N 35/1016* (2013.01); *G01N 1/2813* (2013.01); *G01N 2035/1018* (2013.01)

(58) Field of Classification Search
CPC ............ G01N 11/167; G01N 33/4905; G01N 2021/5973
USPC ................. 600/368, 369; 73/64.41–64.43
See application file for complete search history.

(56) References Cited

U.S. PATENT DOCUMENTS

| 3,119,253 | A | * | 1/1964 | Le Vacher ................... 73/64.41 |
| 5,763,265 | A | * | 6/1998 | Itsuzaki et al. ............. 435/288.7 |
| 2005/0163354 | A1 | * | 7/2005 | Ziegler ......................... 382/128 |
| 2007/0092405 | A1 | * | 4/2007 | Kautzky ........................ 422/73 |

FOREIGN PATENT DOCUMENTS

| JP | 10-019899 | 1/1998 |
| JP | 11-248853 | 9/1999 |

* cited by examiner

*Primary Examiner* — Patricia Mallari
*Assistant Examiner* — Tiffany Weston
(74) *Attorney, Agent, or Firm* — Brinks Gilson & Lione

(57) ABSTRACT

The present invention is to present a blood sample analyzing apparatus, comprising: an aspirator for aspirating a blood sample to be used for measurement; a coagulation determiner for determining whether the blood sample is coagulated or not; and an aspirating controller for controlling an operation of the aspirator based on a determination result by the coagulation determiner.

16 Claims, 37 Drawing Sheets

FIG.27

| RACK ID | SR0001 | | | 160 |
|---|---|---|---|---|
| 161a | 1 | × × ×1 | CBC,DIFF | |
| 161b | 2 | × × ×2 | CBC,DIFF | |
| 161c | 3 | | | |
| 161d | 4 | × × ×4 | CBC,DIFF,NRBC | |
| 161e | 5 | × × ×5 | CBC,DIFF | |
| 161f | 6 | × × ×6 | CBC,DIFF | MICRO-MEASUREMENT MODE |
| 161g | 7 | × × ×7 | CBC,DIFF,RET | |
| 161h | 8 | × × ×8 | CBC | |
| 161i | 9 | | | |
| 161j | 10 | × ×10 | CBC,DIFF | |
| | HOLDING POSITION INFORMATION | SPECIMEN ID | ANALYSIS ITEM DATA | MICRO-MEASUREMENT MODE INSTRUCTION DATA |

MEASURING ORDER (spans SPECIMEN ID and ANALYSIS ITEM DATA)

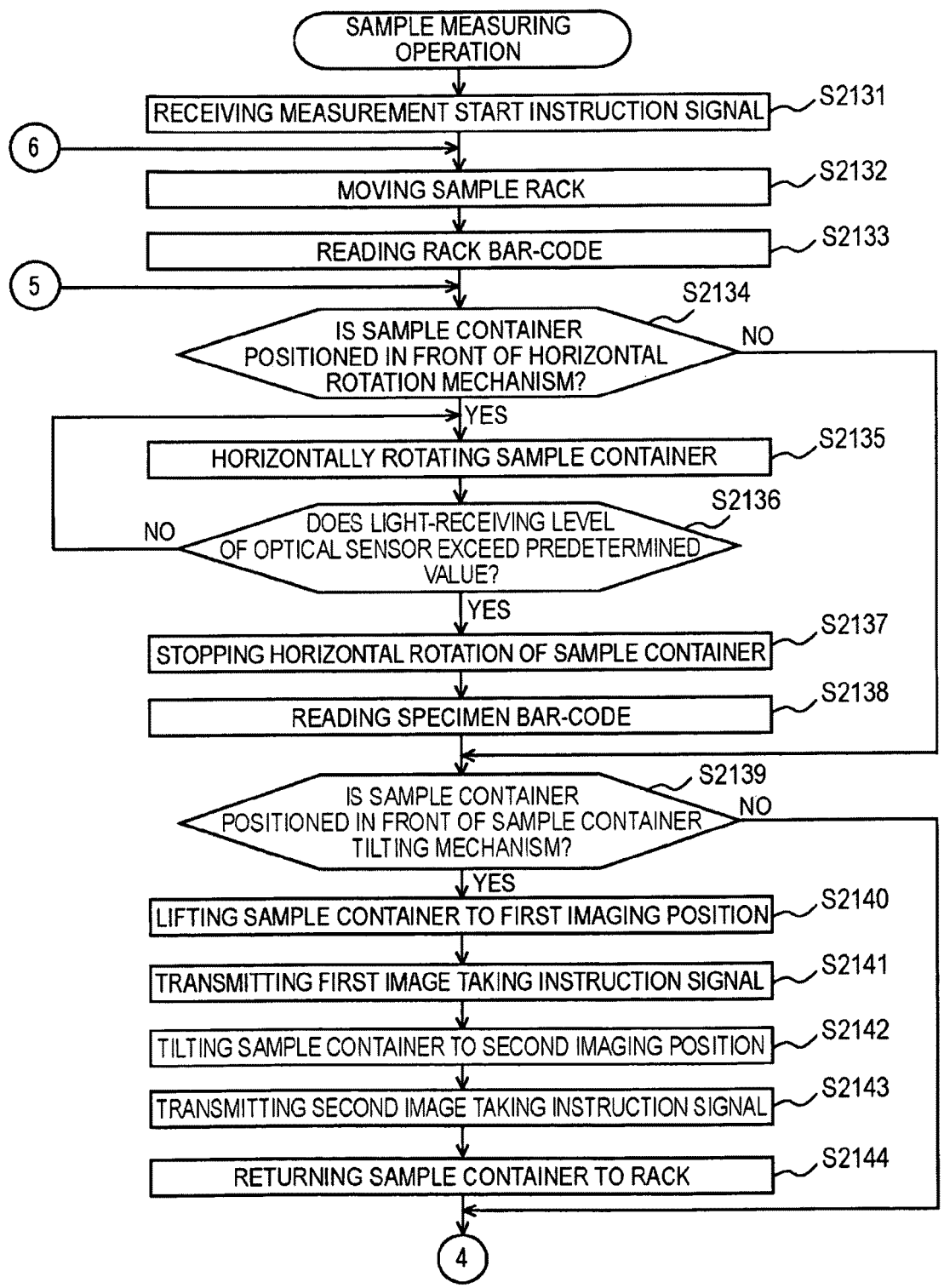

<2: SAMPLE PUTTING APPARATUS>

BLOOD SAMPLE ANALYZING APPARATUS, BLOOD SAMPLE COAGULATION DETERMINING APPARATUS, BLOOD SAMPLE COAGULATION DETERMINING METHOD AND COMPUTER PROGRAM PRODUCT

RELATED APPLICATIONS

This application claims priority under 35 U.S.C. §119 to Japanese Patent Application Nos. 2008-200177 and JP2008-200178 filed on Aug. 1, 2008, the entire contents of which are hereby incorporated by reference.

FIELD OF THE INVENTION

The present invention relates to a blood sample analyzing apparatus for analyzing a blood sample, a blood sample coagulation determining apparatus for imaging a sample container containing a blood sample and determining whether the blood sample in the sample container is coagulated based on the obtained image, a blood sample coagulation determining method and a computer program product.

BACKGROUND

Japanese Patent Publication No. H10-19899 discloses a blood analyzing apparatus which includes an analyzing operation module for aspirating blood from a blood collection tube used for containing the blood collected from a patient to perform analysis and a transport line for transporting the blood collection tube containing the blood to the analyzing operation module. Sometimes, the contained blood is coagulated in the blood collection tube. When the blood collection tube containing the coagulated blood is transported on the transport line and the blood is aspirated by the analyzing operation module, the nozzle for aspirating the blood becomes clogged. Accordingly, it is necessary to take all the blood collection tubes one by one by an operator's hand in order to confirm whether blood is coagulated and remove the blood collection tube containing the coagulated blood from the transport line.

Japanese Patent Publication No. H11-248853 discloses a coagulated specimen determining apparatus for automatically determining whether blood in a blood collection tube is coagulated without depending on human vision. The coagulated specimen determining apparatus is configured to image the blood in a blood collection tube vertically held and the blood in a blood collection tube tilted at a predetermined angle by a camera, calculate areas of blood portions by binarizing the taken images, and compare a difference between the two areas with a reference value, thereby determining whether the blood in the blood collection tube is coagulated. Moreover, the coagulated specimen determining apparatus is configured to display "there is coagulated matter" on a monitor screen when it is determined that the blood in the blood collection tube is coagulated.

In the coagulated specimen determining apparatus disclosed in Japanese Patent Publication No. H11-248853, it is possible to know whether blood in a blood collection tube is coagulated when a user confirms the display of the monitor screen. However, it is necessary to remove the blood collection tube containing the coagulated blood from a transport line in order to exclude the coagulated blood from the measuring targets. Accordingly, a problem occurs in that operator's time and effort is required. Moreover, in the coagulated specimen determining apparatus disclosed in Japanese Patent Publication No. H11-248853, an area of a blood portion is not accurately proportional to a blood volume in a blood collection tube and a difference between the areas of blood portions in two binarized images changes depending on the volume of blood contained in the blood collection tube. Accordingly, the accuracy of coagulation determination varies depending on the blood volume. In addition, when coagulated matter protrudes from the liquid surface of the blood in a blood collection tube, the liquid surface of the blood is lowered in accordance with an amount of the protrusion. Accordingly, in some cases, the difference between the areas of the blood portions in the binarized images is almost the same as the difference between areas of blood portions in binarized images obtained when blood which is not coagulated is imaged. Thus, in the coagulated specimen determining apparatus, it is impossible to achieve the desired high-accuracy determination of blood coagulation.

SUMMARY OF THE INVENTION

The first aspect of the present invention is a blood sample analyzing apparatus, comprising: an aspirator for aspirating a blood sample to be used for measurement; a coagulation determiner for determining whether the blood sample is coagulated or not; and an aspirating controller for controlling an operation of the aspirator based on a determination result by the coagulation determiner.

The second aspect of the present invention is a blood sample analyzing apparatus, comprising: a transporter for transporting a blood sample to be used for measurement; an aspirator for aspirating the blood sample transported by the transporter; a coagulation determiner for determining whether the blood sample is coagulated or not; and a transporting controller for controlling the transporter based on a determination result by the coagulation determiner.

The third aspect of the present invention is a blood sample coagulation determining apparatus, comprising: a sample container holder capable of holding a sample container, which has translucency, contains a blood sample and a top opening of which is sealed by a lid, in a state that a bottom portion of the sample container is positioned at the same height as the lid or higher than the lid; an imaging part for imaging the sample container held by the sample container holder in a state that the bottom portion of the sample container is positioned at the same height as the lid or higher than the lid; and a coagulation determiner for determining whether the blood sample in the sample container is coagulated or not, based on the presence or absence of a clot protruding from a liquid surface of the blood sample in the sample container in a container image obtained by imaging the sample container with the imaging part.

The fourth aspect of the present invention is a blood sample coagulation determining method, comprising steps of: holding a sample container, which has translucency, contains a blood sample and a top opening of which is sealed by a lid, in a state that a bottom portion of the sample container is positioned at the same height as the lid or higher than the lid; imaging the sample container held in a state that the bottom portion of the sample container is positioned at the same height as the lid or higher than the lid; and determining whether the blood sample in the sample container is coagulated or not, based on the presence or absence of a clot protruding from a liquid surface of the blood sample in the sample container in an image obtained by imaging the sample container.

The fifth aspect of the present invention is a computer program product for enabling a computer to determine whether a blood sample is coagulated or not, comprising: a computer readable medium, and software instructions, on the computer readable medium, for enabling the computer to perform predetermined operations comprising: processing an image obtained by imaging a sample container, which has translucency, contains a blood sample and a top opening of which is sealed by a lid, in a state that a bottom portion of the sample container is positioned at the same height as the lid or higher than the lid, and detecting a height of a liquid surface of the blood sample in the sample container in the image; and determining whether the blood sample in the sample container is coagulated or not, based on the presence or absence of a clot protruding from a liquid surface of the blood sample in the sample container in the image.

BRIEF DESCRIPTION OF THE DRAWINGS

FIG. 27 is a schematic diagram showing the data structure of measuring order information;

FIG. 30B is a flowchart (first half) showing the flow of a sample measuring operation of a measuring unit according to the second embodiment;

DETAILED DESCRIPTION OF THE PREFERRED EMBODIMENTS

Hereinafter, preferred embodiments of the invention will be described with reference to the drawings.

(First Embodiment)

[Configuration of Blood Sample Analyzing System]

Figure 1:
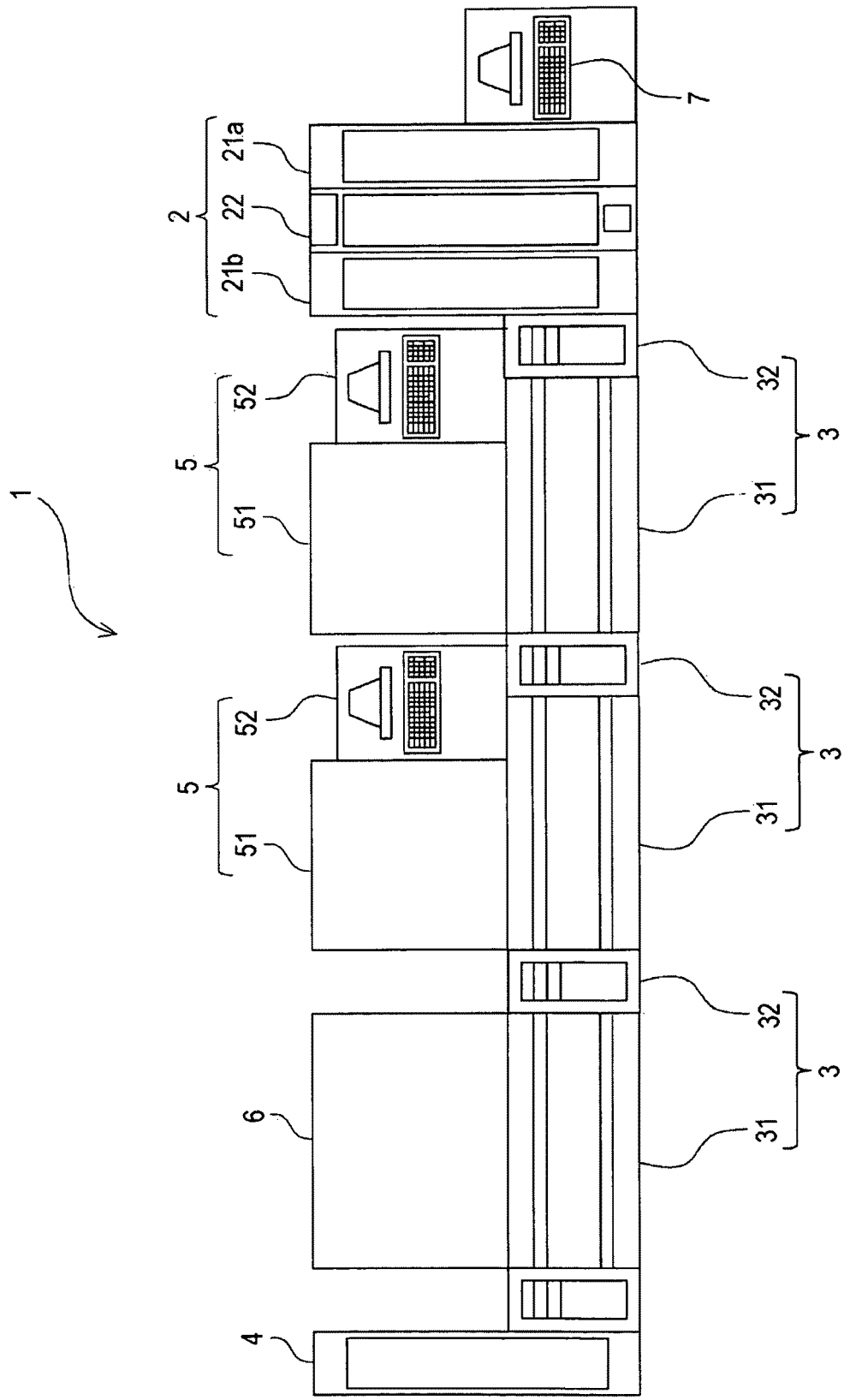
FIG. 1 is a schematic plan view showing the entire configuration of a blood sample analyzing system according to a first embodiment.

FIG. 1 is a schematic plan view showing the entire configuration of a blood sample analyzing system according to this embodiment. As illustrated in FIG. 1, a blood sample analyzing system 1 includes a sample putting apparatus 2, sample transport apparatuses 3, a sample storing apparatus 4, blood cell analyzing apparatuses 5, a smear preparing apparatus 6 and a system control apparatus 7.

<Configuration of Sample Putting Apparatus 2>

The sample putting apparatus 2 includes two sample delivery units 21a and 21b and a sample check unit 22 disposed between the two sample delivery units 21a and 21b. Plural sample racks storing plural sample containers can be placed in the sample putting apparatus 2. In addition, the sample putting apparatus performs coagulation determination and blood volume detection of a blood sample in a sample container stored in a sample rack, and reads a bar-code of a bar-code label adhered to the sample container to obtain a specimen ID and to transmit the specimen ID, a coagulation determination result, and data of a blood volume to the system control apparatus 7.

Figure 2:
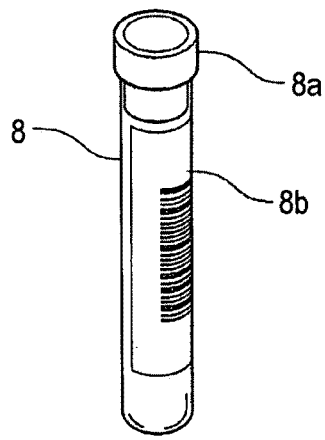
FIG. 2 is a perspective view showing the appearance of a sample container.
Figure 3:
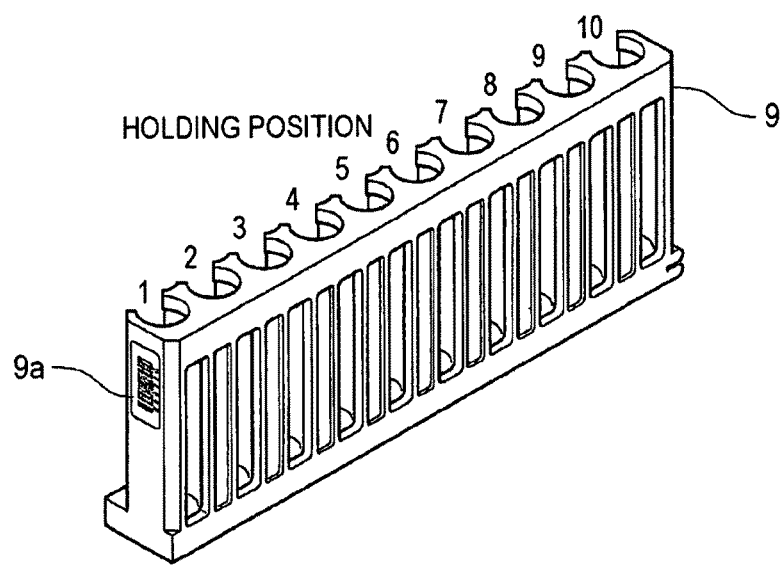
FIG. 3 is a perspective view showing the appearance of a sample rack.

FIG. 2 is a perspective view showing the appearance of the sample container and FIG. 3 is a perspective view showing the appearance of the sample rack. As shown in FIG. 2, a tube-shaped sample container 8 is open at a top end thereof. A blood sample collected from a patient is contained in the sample container 8 and the opening at the top end is sealed by a lid 8a. The sample container 8 is made of translucent glass or synthetic resin and the blood sample therein can be visually confirmed. A bar-code label 8b is adhered to a side face of the sample container 8 and a bar-code indicating a specimen ID is printed on the bar-code label 8b. A sample rack 9 can hold the ten sample containers 8 in parallel. In the sample rack 9, the sample containers 8 are held in a vertical state (erect state). A bar-code label 9a is adhered to a side face of the sample rack 9 and a bar-code indicating a rack ID is printed on the bar-code label 9a.

Figure 4:
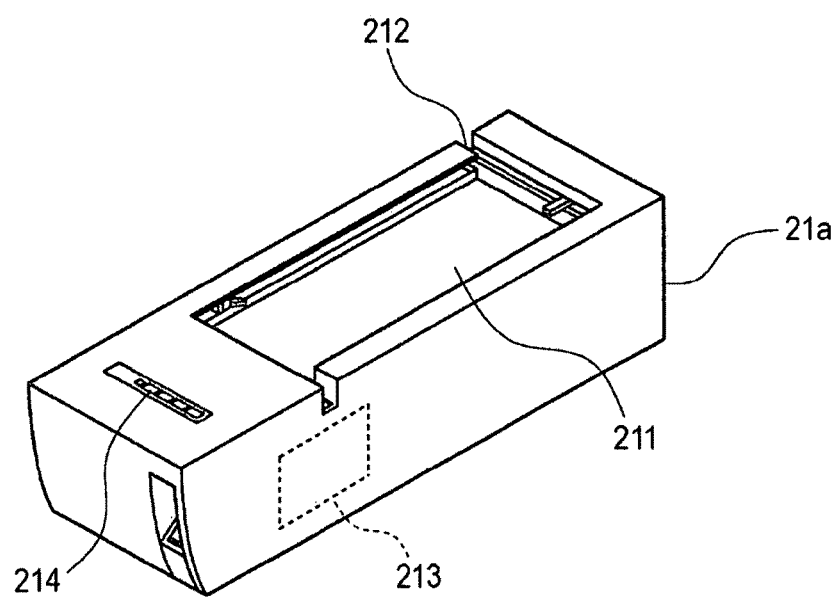
FIG. 4 is a perspective view showing the appearance configuration of a sample delivery unit.

FIG. 4 is a perspective view showing the appearance configuration of the sample delivery unit 21a. As shown in FIG. 4, the sample delivery unit 21a has a concave rack placing section 211 for placing the sample rack 9 storing the sample containers 8. The rack placing section 211 has a rectangular shape and the plural sample racks 9 can be simultaneously placed. At this time, the sample racks 9 are placed so that the sample containers 8 line up in a transverse direction. The rack placing section 211 is provided with an engaging section (not shown). The engaging section moves in a front-back direction while engaging with the sample rack 9 as so to move the sample rack 9 on the rack placing section 211. The sample delivery unit 21b is provided with a controller 213 composed of a CPU and a memory. The controller 213 controls the operating mechanisms such as the engaging section.

The sample delivery unit 21a is disposed on the right side of the sample check unit 22 (see FIG. 1 for reference). A left wall section on the inner side of the rack placing section 211 of the sample delivery unit 21a is missing and this missing portion serves as a rack delivery port 212. The sample rack 9 placed in the rack placing section 211 is moved in a direction toward the inner side from the front side, that is, in a backward direction to reach a position on the innermost side of the rack placing section 211, and then is conveyed toward the sample check unit 22 on the left side of the rack delivery port 212. In the sample delivery unit 21b disposed on the left side of the sample check unit 22, a right wall section on the inner side of a rack placing section 211 is missing so as to form a rack feed port (not shown) and the sample rack 9 is fed from the sample check unit 22 by the rack feed port. A left wall section on the front side (front face-side) of the rack placing section 211 of the sample delivery unit 21b is also missing (not shown) and this portion serves as a rack delivery port. The sample rack 9 fed from the rack feed port is moved to the front by the rack placing section 211 to reach a foremost position, and then is delivered to the left from the rack delivery port.

As shown in FIG. 4, the sample delivery unit 21a is provided with an operating panel 214. A user operates the operating panel 214 to issue an instruction for analysis start or an instruction for analysis completion to the blood sample analyzing system 1.

Figure 5:
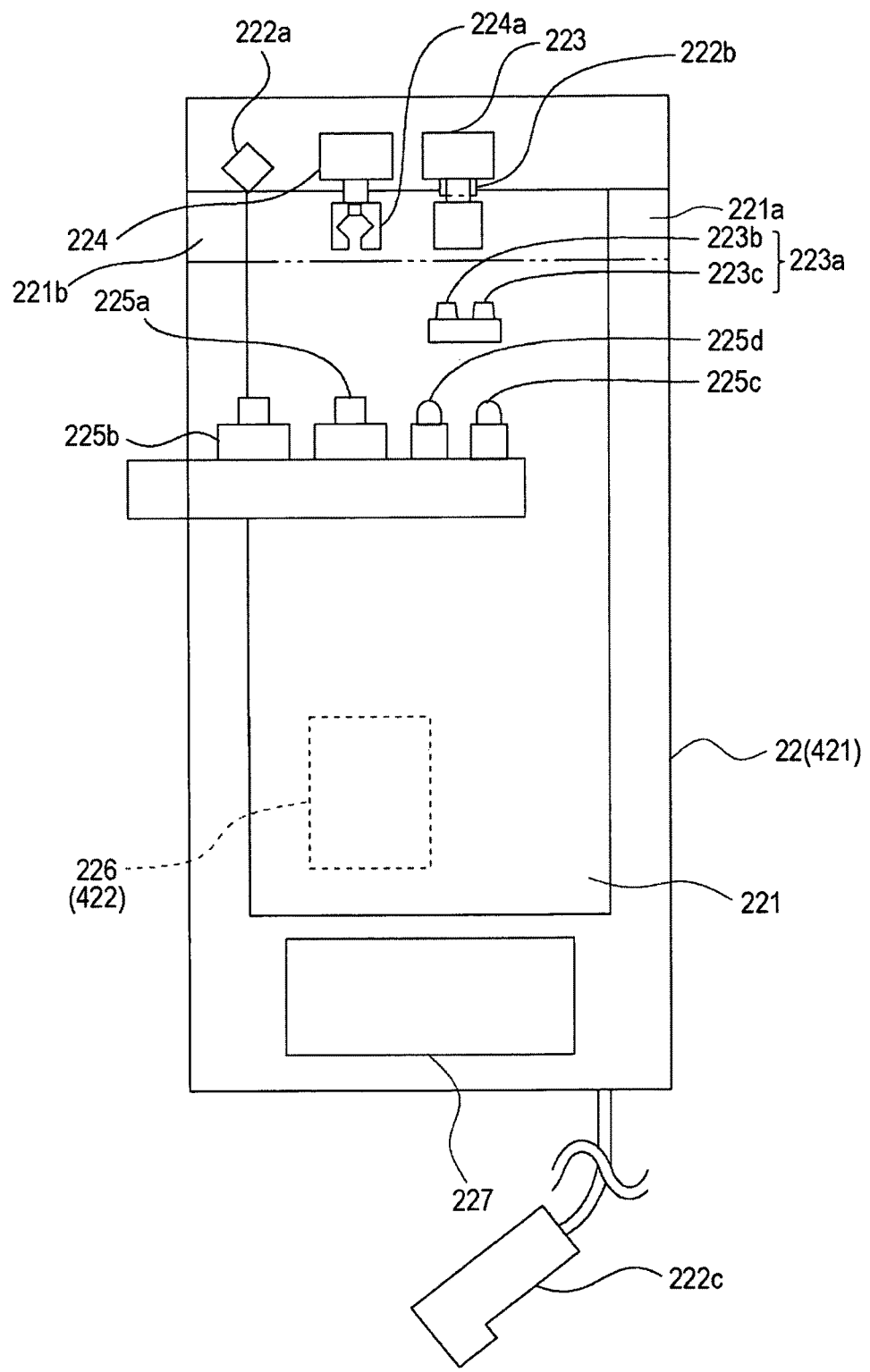
FIG. 5 is a plan view showing the configuration of a sample check unit.

FIG. 5 is a plan view showing the configuration of the sample check unit 22. As shown in FIG. 5, the sample check unit 22 includes a rack placing section 221 for placing the sample rack 9 fed from the sample delivery unit 21a, a bar-code reader 222a for reading a bar-code (rack bar-code) of the sample rack 9 on the rack placing section 221, a bar-code reader 222b for reading a bar-code (specimen bar-code) of the sample container 8 stored in the sample rack 9, a handy bar-code reader 222c which is manually operated by the user, a horizontal rotation mechanism 223 for horizontally rotating the sample container 8, an optical sensor 223a for detecting the presence or absence of the bar-code label 8b on the sample container 8, a sample container tilting mechanism 224 for taking out the sample container 8 from the sample rack 9 and tilting the sample container, two cameras 225a and 225b for imaging the sample container 8, a controller 226 for controlling the operating mechanisms such as the horizontal rotation mechanism 223 and the sample container tilting mechanism 224, and a liquid crystal display section 227. The controller 226 is composed of a CPU and a memory. The sample check unit 22 is connected to the system control apparatus 7 to perform data communication therewith, and is configured to transmit to the system control apparatus 7 the data read by the bar-code readers 222a, 222b and 222c and images captured by the cameras 225a and 225b.

The rack placing section 221 is rectangular in a plan view and is hollowed in a concave shape. A rack feed port 221a for feeding the sample rack 9 from the sample delivery unit 21a is provided in a right wall section at the inner end of the rack placing section 221. In addition, a rack delivery port 221b for delivering the sample rack 9 from the rack placing section 221 is provided in a left wall section at the inner end of the rack placing section 221. A portion on the innermost side of the rack placing section 221 (in the drawing, a portion shown by the two-dot chain line) is used as a transport path for transporting the sample rack 9 and a portion other than this portion is used to store the sample rack 9.

The bar-code reader 222a is provided with a light-emitting section and a light-receiving section (line sensor) (not shown), and is positioned so as to read the rack bar-code of the sample rack 9 on the transport path. The sample rack 9 fed from the rack feed port 221a is held by holding means (not shown) and moved on the above-described transport path. The bar-code reader 222a reads the rack bar-code of the sample rack 9 on the transport path. The read rack ID is transmitted to the system control apparatus 7.

The bar-code reader 222b is provided with a light-emitting section and a light-receiving section (line sensor) (not shown), and is positioned so as to read the specimen bar-code of the sample container 8 stored in the sample rack 9 on the transport path. The horizontal rotation mechanism 223 is provided above the bar-code reader 222*b*.

Figure 6:
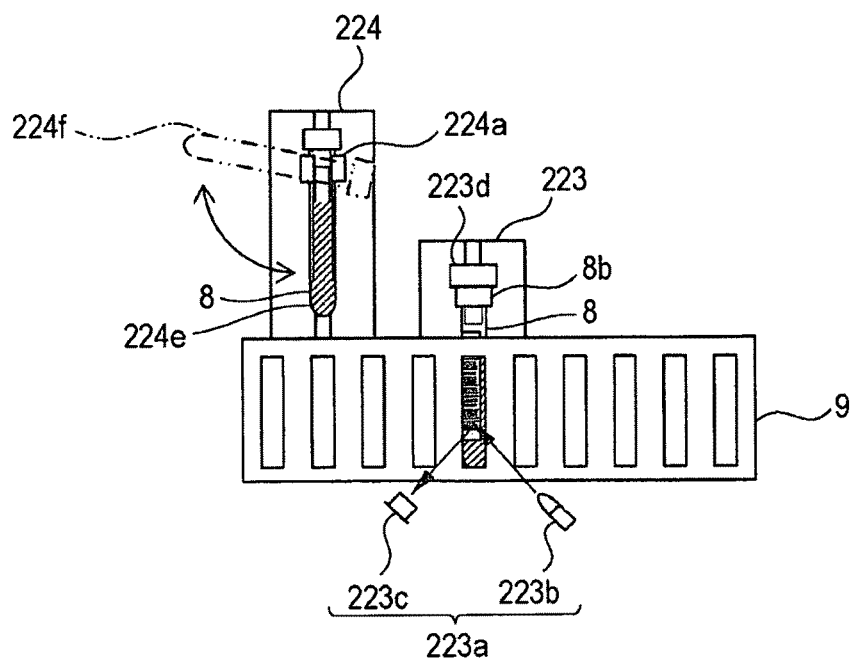
FIG. 6 is a front view schematically showing the configuration of a part of the sample check unit.

FIG. 6 is a front view schematically showing the configuration of a part of the sample check unit 22. As shown in FIG. 6, the horizontal rotation mechanism 223 has a contacting section 223*d* which is brought into contact with the upper end of the sample container 8 on the sample rack 9, and the contacting section 223*d* is configured to be horizontally rotated by a motor. When the contacting section 223*d* is horizontally rotated while brought into contact with the lid 8*a* of the sample container 8, the sample container 8 is horizontally rotated in the sample rack 9. In addition, the optical sensor 223*a* is disposed in front of the horizontal rotation mechanism 223. The optical sensor 223*a* is composed of a light-emitting element 223*b* and a light-receiving element 223*c*. While the sample container 8 is horizontally rotated by the horizontal rotation mechanism 223, the sample container 8 is irradiated with light from the light-emitting element 223*b* and the light reflected is received by the light-receiving element 223*c*. When the bar-code label is disposed on the face reflecting the light of the light-emitting element 223*b*, a light-receiving level of the light-receiving element 223*c* exceeds a predetermined value, and when the bar-code label is not disposed on the face reflecting the light of the light-emitting element 223*b*, the light-receiving level is less than the predetermined value. The controller 226 checks the light-receiving level of the light-receiving element 223*c* of the optical sensor 223*a* while horizontally rotating the sample container 8, and stops the horizontal rotation operation of the horizontal rotation mechanism 223 at a position where the light-receiving level is equal to or less than the predetermined value. Accordingly, an angle of the sample container 8 is adjusted so that the face on which the bar-code label 8*b* is not disposed faces the front side.

As described above, when the face on which the bar-code label 8*b* is not disposed faces the front side, the bar-code reader 222*b* in the rear of the sample container 8 is opposed to the bar-code label 8*b* of the sample container 8. Herein, the bar-code reader 222*b* reads the specimen ID from the bar-code label 8*b*.

Furthermore, the optical sensor 223*a* can be vertically moved by a vertical driving mechanism (not shown). The optical sensor 223*a* is disposed in front of the sample rack 9 when the sample rack 9 is on the transport path of the rack placing section 221. When the sample rack 9 is moved to the front side of the rack placing section 221, the optical sensor 223*a* is lifted by the vertical driving mechanism up to a position which does not interfere with the movement of the sample rack 9.

Figure 7:
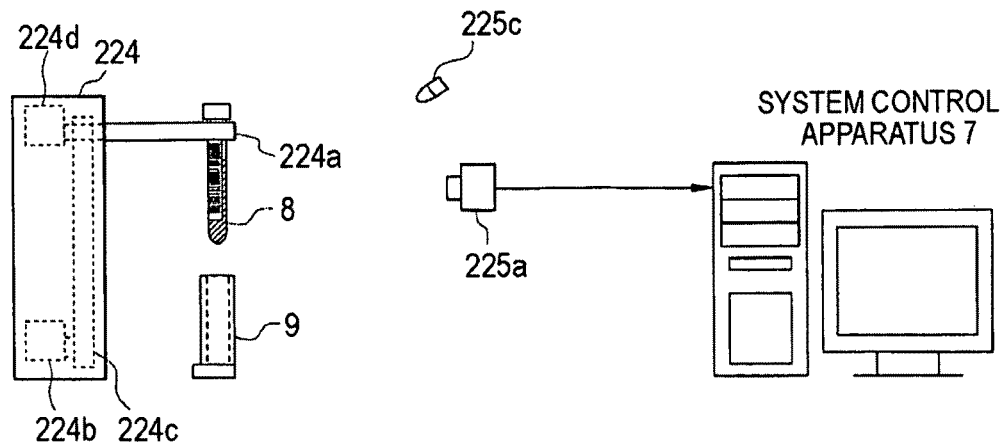
FIG. 7 is a side view showing the schematic configuration of a sample container tilting mechanism.

On the transport path of the rack placing section 221, the sample rack 9 is intermittently moved to the left in a pitch feeding manner in which the gap between the neighboring sample containers 8 is set as one pitch. The above-described sample container tilting mechanism 224 is provided so as to be positioned on the left side of the horizontal rotation mechanism 223 by a predetermined pitch. FIG. 7 is a side view showing the schematic configuration of the sample container tilting mechanism 224. The sample container tilting mechanism 224 includes a grasping section 224*a* for grasping the vicinity of the top end of the sample container from both the right and left sides, a motor 224*b*, and a belt 224*c* for connecting a rotation shaft of the motor 224*b* with the grasping section 224*a*, and the grasping section 224*a* can be vertically moved by the rotation of the motor 224*b*. Furthermore, the grasping section 224*a* is connected to a rotation shaft of a motor 224*d* and the grasping section 224*a* can be rotated around a center axis extending in a front-back direction by the rotation of the motor 224*d*.

The sample container 8, which is rotated by the horizontal rotation mechanism 223 so that the bar-code label 8*b* is not disposed on the front face, reaches the position of the sample container tilting mechanism 224 by moving the sample rack 9 to the left. Herein, when the grasping section 224*a* of the sample container tilting mechanism 224 grasps the vicinity of the top end of the sample container 8 and is lifted in such a state, the sample container 8 is taken out from the sample rack 9. When the sample container 8 is completely separated from the sample rack 9 and reaches a first imaging position 224*e*, the lift operation of the grasping section 224*a* is stopped. The camera 225*a* is disposed in front of the sample container 8 positioned at the first imaging position 224*e*. A white LED 225*c* is disposed at a predetermined position with respect to the camera 225*a* and the sample container 8 is illuminated by the white LED 225*c*.

Figure 8:
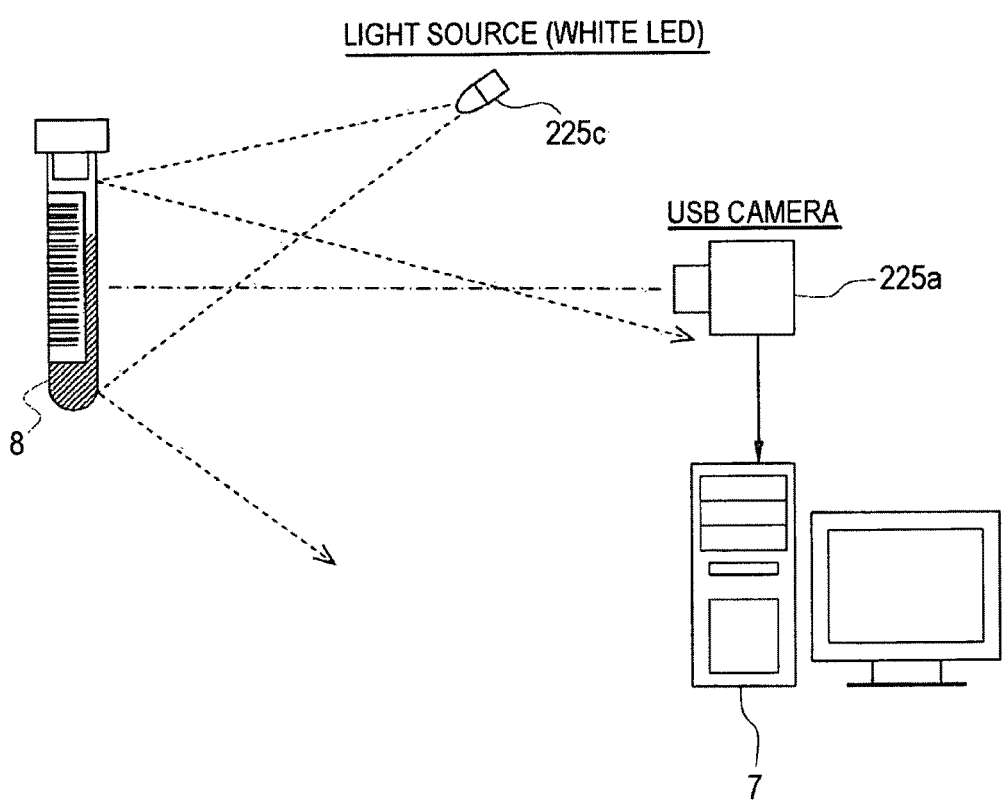
FIG. 8 is a schematic diagram for illustrating a positional relationship among a camera, a white LED and the sample container in the sample check unit, and a direction of the light emitted from the white LED.

FIG. 8 is a schematic diagram for illustrating a positional relationship among the camera 225*a*, the white LED 225*c* and the sample container 8, and a direction of the light emitted from the white LED. As shown in FIG. 8, the white LED 225*c* is disposed, so that light reflected from the sample container 8 does not directly enter the camera 225*a* positioned in front of the sample container 8 when the light is emitted toward the sample container 8 positioned at the first imaging position 224*e*. Accordingly, the camera 225*a* is not directly exposed to the reflected light and so-called halation by overexposure can be prevented.

The sample container 8 grasped at the first imaging position 224*e* by the grasping section 224*a* is imaged by the camera 225*a* while being in an erect state (vertical state), and the image data obtained in this manner is transmitted to the system control apparatus 7. After that, the grasping section 224*a* is vertically rotated by the motor 224*d* to tilt the sample container 8. As shown by the two-dot chain line in FIG. 6, the grasping section 224*a* is turned by a predetermined angle so that a bottom portion of the sample container 8 reaches a second imaging position 224*f* positioned higher than the lid 8*a*. The camera 225*b* (see FIG. 5 for reference) is disposed in front of the sample container 8 positioned at the second imaging position 224*f*. A white LED 225*d* (see FIG. 5 for reference) is disposed at a predetermined position with respect to the camera 225*b* and the sample container 8 is illuminated by the white LED 225*d*. A relative positional relationship between the white LED 225*d* and the camera 225*b* is the same as a relative positional relationship between the white LED 225*c* and the camera 225*a*. That is, the white LED 225*d* is disposed, so that light reflected from the sample container 8 does not directly enter the camera 225*b* positioned in front of the sample container 8 when the light is emitted toward the sample container 8 positioned at the second imaging position 224*f*.

The sample container 8 grasped at the second imaging position 224*f* by the grasping section 224*a* is imaged by the camera 225*a* while being tilted as described above, and the image data obtained in this manner is transmitted to the system control apparatus 7. The sample rack 9 in which all the sample containers 8 have been imaged is delivered from the rack delivery port 221*b*.

The bar-code reader 222*c* is provided with a light-emitting section and a light-receiving section (line sensor) (not shown), and is connected to a main body of the sample check unit 22 by a flexible cable for transmitting an electric signal.

The bar-code reader 222c is operated when the user manually reads the bar-code which cannot be read by the bar-code reader 222b again.

<Configuration of Sample Transport Apparatus 3>

Next, the configuration of the sample transport apparatus 3 will be described. As shown in FIG. 1, the blood sample analyzing system 1 is provided with the three sample transport apparatuses 3. The sample transport apparatuses 3 are disposed in front of the blood cell analyzing apparatuses 5 and the smear preparing apparatus 6, respectively. The neighboring sample transport apparatuses 3 are connected to each other and can deliver the sample rack 9. The rightmost sample transport apparatus 3 is connected to the above-described sample putting apparatus 2 to feed the sample rack 9 conveyed from the sample putting apparatus 2. The leftmost sample transport apparatus 3 is connected to the sample storing apparatus 4 to convey the sample rack 9 toward the sample storing apparatus 4.

Figure 9:
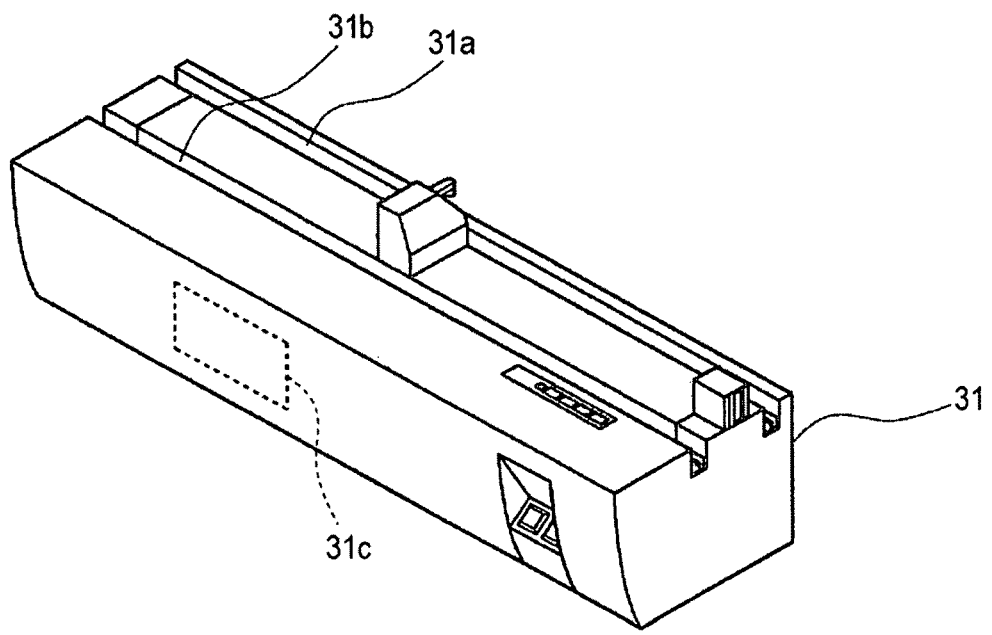
FIG. 9 is a perspective view showing the configuration of a conveyor.
Figure 10:
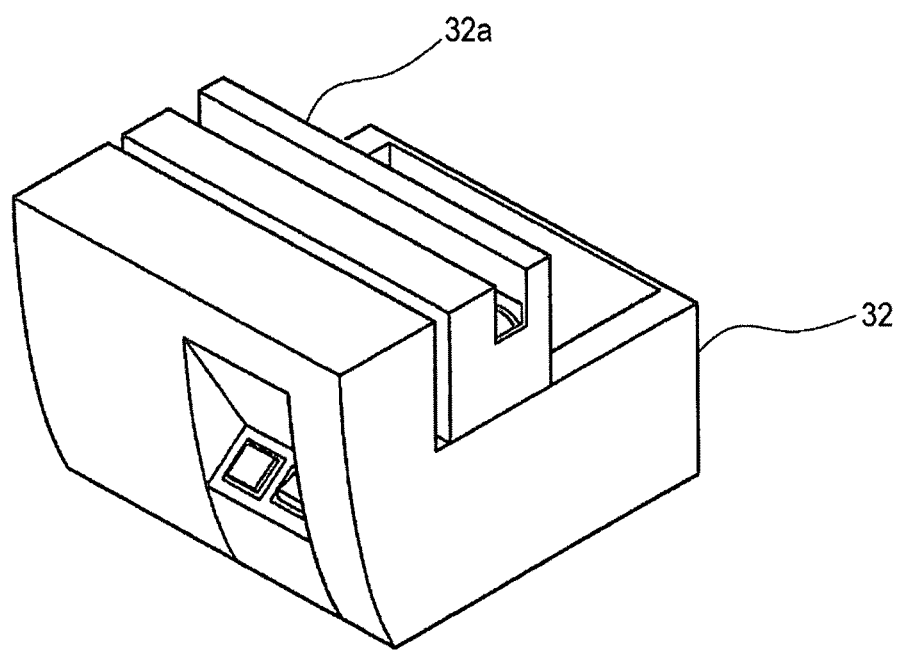
FIG. 10 is a perspective view showing the configuration of a rack slider.

The respective sample transport apparatuses 3 are provided with a conveyor 31 and a rack slider 32. FIG. 9 is a perspective view showing the configuration of the conveyor 31 and FIG. 10 is a perspective view showing the configuration of the rack slider 32. As shown in FIG. 9, the conveyor 31 is provided with two rack transport paths 31a and 31b extending in a horizontal direction. The rack transport path 31a at the rear side is a measuring line for transporting the sample rack 9 containing a sample to be supplied to the blood cell analyzing apparatus 5 or the smear preparing apparatus 6. The rack transport path 31b at the front side is a skip line for transporting the sample rack 9 not containing a sample to be supplied to the blood cell analyzing apparatus 5 or the smear preparing apparatus 6. In addition, the conveyor 31 is provided with a controller 31c for controlling the operating mechanisms. The controller 31c is provided with a CPU and a memory.

The rack slider 32 is disposed on the right side of the conveyor 31 to sort and put the sample racks 9 into the measuring line 31a and the skip line 31b of the conveyor 31. The rack slider 32 is provided with one movable transport path 32a and the movable transport path 32a can be moved in a front-back direction by a motor (not shown). The above-described controller 31c controls an operation of the movable transport path 32a.

In addition, the respective sample transport apparatus 3 are provided with a rack bar-code reader (not shown) and rack IDs read by the bar-code reader are provided to the controller 31c. Moreover, the sample transport apparatus 3 is connected to the system control apparatus 7 to communicate therewith and is configured to receive a measuring order from the system control apparatus 7. The controller 31c determines whether a sample to be supplied to the blood cell analyzing apparatus 5 or the smear preparing apparatus 6 is contained in the sample rack 9 on the basis of the measuring order provided from the system control apparatus 7 and the rack ID read by the bar-code reader. When the sample rack 9 containing the sample to be supplied to the blood cell analyzing apparatus 5 or the smear preparing apparatus 6 is fed to the rack slider 32, the movable transport path 32a is moved to the back to deliver the sample rack 9 to the measuring line 31a. When the sample rack 9 not containing the sample to be supplied to the blood cell analyzing apparatus 5 or the smear preparing apparatus 6 is fed to the rack slider 32, the movable transport path 32a is moved to the front to deliver the sample rack 9 to the skip line 31b. That is, the sample rack 9 containing only a sample which is not an analysis target of the blood cell analyzing apparatus 5 is transported to the skip line 31b in the sample transport apparatus 3 disposed in front of the blood cell analyzing apparatus 5. The sample rack 9 containing only a sample which is not a target for preparing a smear by the smear preparing apparatus 6 is transported to the skip line 31b in the sample transport apparatus 3 disposed in front of the smear preparing apparatus 6. When the sample rack 9 contains any sample, which is an analysis target of the blood cell analyzing apparatus 5, the sample rack 9 is transported to the measuring line 31a in the sample transport apparatus 3 disposed in front of the blood cell analyzing apparatus 5.

When the sample rack 9 is delivered to the measuring line 31a, the controller 31c repeats an operation of: moving the sample container which is a target of analysis (smear preparing process) to an aspiration position where the blood cell analyzing apparatus 5 (smear preparing apparatus 6) aspirates the sample; and moving the sample container which is the next analysis target (target for smear preparing process) to the aspiration position after the blood cell analyzing apparatus 5 (smear preparing apparatus 6) completes the aspiration of the sample.

<Configuration of Sample Storing Apparatus 4>

The sample storing apparatus 4 receives the sample rack 9, in which the analysis or smear preparing is completed, from the sample transport apparatus 3, and stores the sample rack. Since the configuration of the sample storing apparatus is the same as those of the sample delivery units 21a and 21b, a description thereof will be omitted.

<Configuration of Blood Cell Analyzing Apparatus 5>

The blood cell analyzing apparatus 5 as an optical flow cytometry type multiple blood cell analyzing apparatus obtains the fluorescent intensity, the side-scattered light intensity and the like of blood cells included in a blood sample, classifies the blood cells included in the sample on the basis of the above intensities, and counts the number of blood cells for each type. Moreover, the blood cell analyzing apparatus 5 creates a scattergram in which the classified blood cells are color-coded for each type, and displays the scattergram. The blood cell analyzing apparatus 5 includes a measuring unit 51 for measuring a blood sample and an information processing unit 52 for process measuring data output from the measuring unit 51 and displaying an analysis result of the blood sample.

Figure 11:
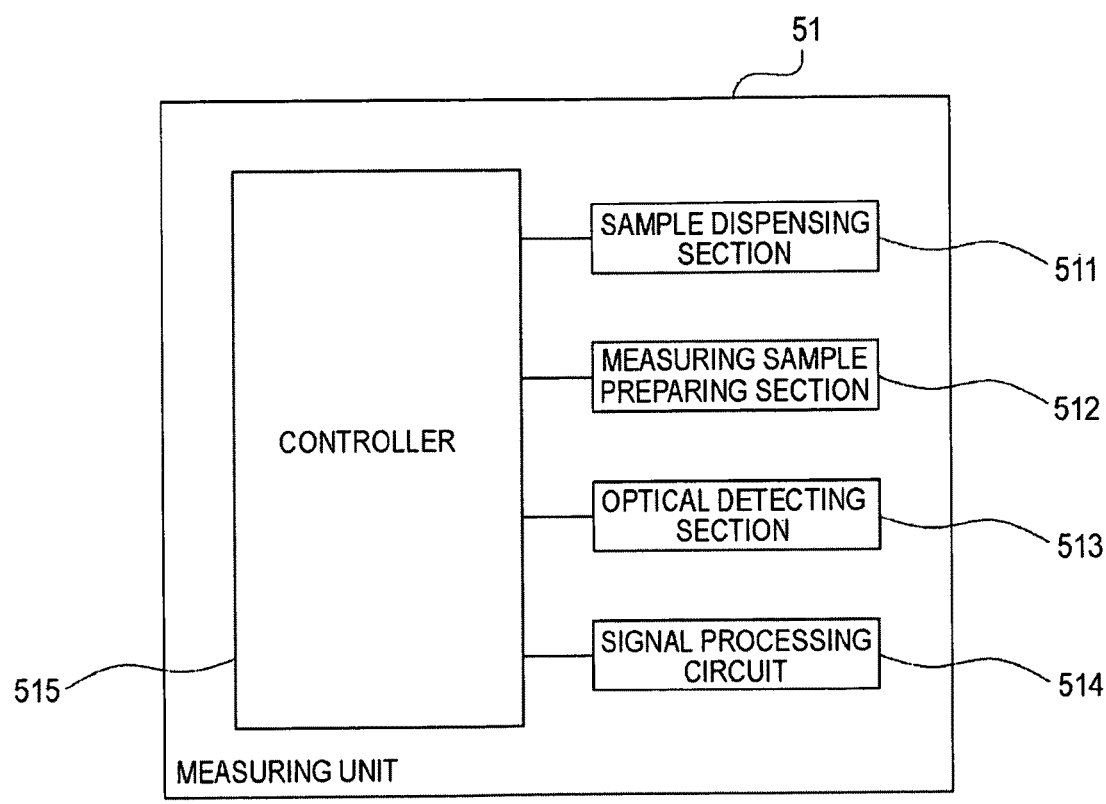
FIG. 11 is a block diagram showing the schematic configuration of a measuring unit according to a first embodiment.

FIG. 11 is a block diagram showing the schematic configuration of the measuring unit 51. The measuring unit 51 includes a sample dispensing section 511, a measuring sample preparing section 512, an optical detecting section 513, a signal processing circuit 514 and a controller 515.

The sample dispensing section 511 is provided with an aspiration tube (not shown) and the aspiration tube is stuck into the lid 8a of the sample container 8 in the sample rack 9 transported on the measuring line 31a of the sample transport apparatus 3 to aspirate a blood sample from the sample container 8. The measuring sample preparing section 512 is provided with a mixing container (not shown) to mix and stir the blood sample dispensed by the sample dispensing section 511, a reagent and a diluents and prepare a measuring sample.

The optical detecting section 513 is provided with a flow cell (not shown) to form a narrow flow of the measuring sample by supplying the measuring sample to the flow cell and exposes the measuring sample to light to obtain a side-scattered light signal, a forward-scattered light signal and a fluorescent signal by an optical sensor. These signals are output to the signal processing circuit 514. The signal processing circuit 514 processes an electric signal output from the optical detecting section 513. The signal processing circuit 514 obtains parameters such as peaks and pulse widths of the side-scattered light signal, the forward-scattered light signal and the fluorescent signal.

The controller 515 is provided with a CPU and a memory, and is connected to the sample transport apparatus 3 to perform data communication therewith. The controller 515 controls the sample dispensing section 5 11, the measuring sample preparing section 512, the optical detecting section 513 and the signal processing circuit 514 in accordance with an analysis item provided from the sample transport apparatus 3, and performs a measuring operation corresponding to the analysis item. In addition, the controller is configured to transmit measuring data including the parameters obtained by the signal processing circuit 514 to the information processing unit 52.

The measuring unit 51 can be operated in two operating modes which are a normal-measurement mode and a micro-measurement mode. In the micro-measurement mode, a smaller volume of a blood sample than in the normal-measurement mode is aspirated by the sample dispensing section 511, a measuring sample of a higher dilution ratio than in the normal-measurement mode is prepared by the measuring sample preparing section 512, and the measuring sample is optically measured by the optical detecting section 513. When the measurement in the micro-measurement mode is performed by the measuring unit 51, an analysis result obtained by the information processing unit 52 is corrected in accordance with the dilution ratio of the measuring sample. Accordingly, even when a slight volume of blood is measured, an analysis result can be obtained with excellent accuracy.

Figure 12:
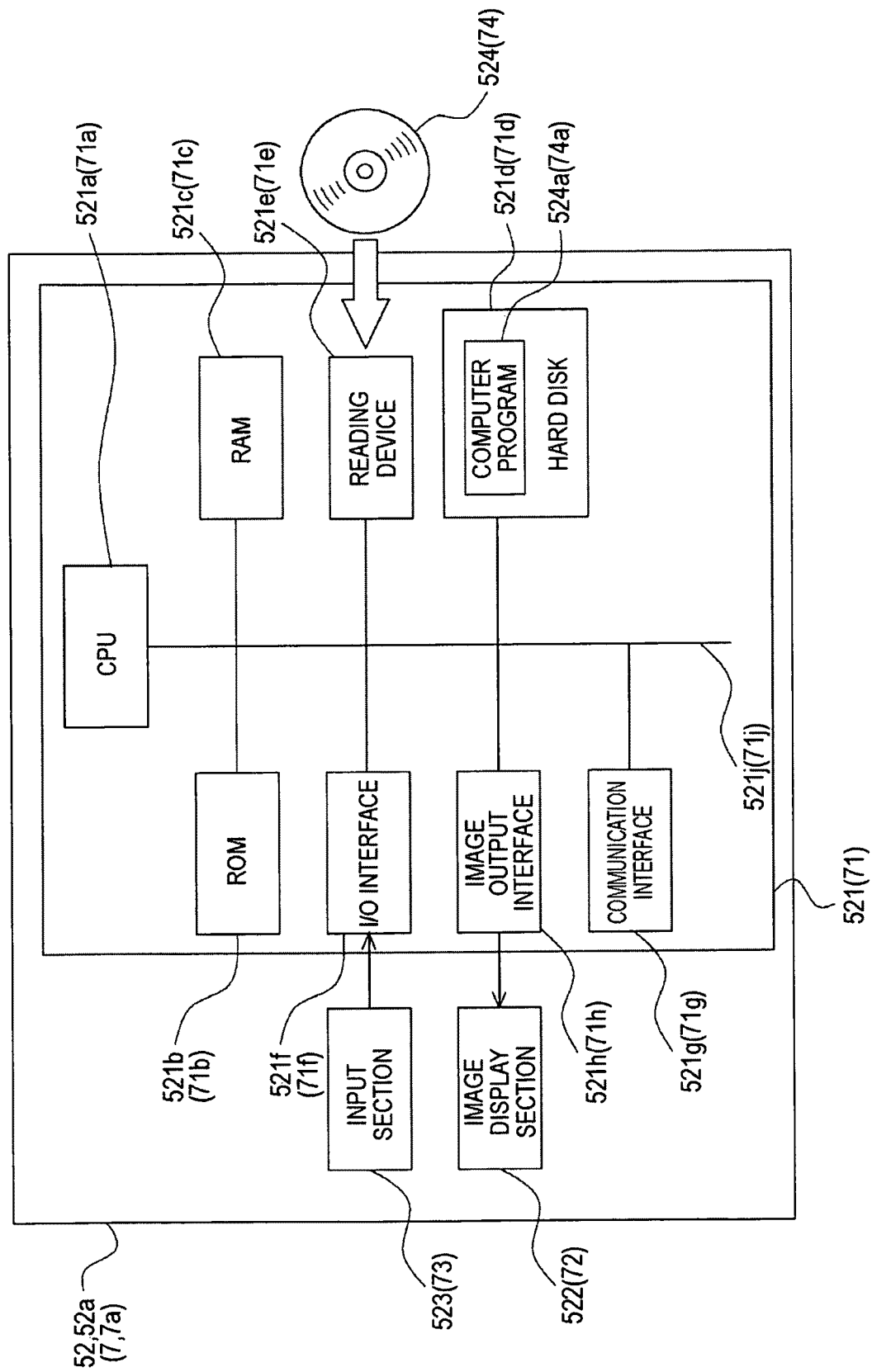
FIG. 12 is a block diagram showing the configuration of an information processing unit according to the first embodiment.

Next, the configuration of the information processing unit 52 will be described. The information processing unit 52 is composed of a computer. FIG. 12 is a block diagram showing the configuration of the information processing unit 52. The information processing unit 52 is realized by a computer 52a. As shown in FIG. 12, the computer 52a includes a main body 521, an image display section 522 and an input section 523. The main body 521 includes a CPU 521a, a ROM 521b, a RAM 521c, a hard disk 521d, a reading device 521e, an I/O interface 521f, a communication interface 521g and an image output interface 521h. The CPU 521a, ROM 521b, RAM 521c, hard disk 521d, reading device 521e, I/O interface 521f, communication interface 521g and image output interface 521h are connected to each other by a bus 521j.

The CPU 521a can execute a computer program loaded to the RAM 521c. The CPU 521a executes an analysis program 524a to be described later, so that the computer 52a functions as the information processing unit 52.

The ROM 521b is composed of a mask ROM, a PROM, an EPROM an EEPROM or the like and the computer program executed by the CPU 521a and data used for the computer program are recorded in the ROM.

The RAM 521c is composed of a SRAM, a DRAM or the like. The RAM 521c is used to read the analysis program 524a recorded in the hard disk 521d. Moreover, the RAM is used as an operating area of the CPU 521a when the CPU 521a executes a computer program.

In the hard disk 521d, various computer programs for being executed by the CPU 521a, such as an operating system and an application program, and data which are used to execute the computer programs are installed. The analysis program 524a to be described later is also installed in the hard disk 521d.

The reading device 521 e is composed of a flexible disk drive, a CD-ROM drive, a DVD-ROM drive or the like and can read the computer program or data recorded in a portable recording medium 524. In the portable recording medium 524, the analysis program 524a for prompting the computer to function as the information processing unit 52 is stored.

The computer 52a can read the analysis program 524a from the portable recording medium 524 and install the analysis program 524a in the hard disk 521d.

The analysis program 524a is provided by the portable recording medium 524 and can be also provided from an external device, which is connected to the computer 52a by an electric communication line (regardless of wired or wireless) to communicate therewith, through the electric communication line. For example, the analysis program 524a is stored in a hard disk of a server computer on the internet and the computer 52a accesses the server computer to download the computer program and install the computer program in the hard disk 521d.

Furthermore, in the hard disk 521d, for example, a multi-tasking operating system such as Windows (registered trade name), which is made and distributed by Microsoft corporation in America, is installed. In the following description, the analysis program 524a according to this embodiment operates on the above operating system.

The I/O interface 521f is composed of, for example, a serial interface such as USB, IEEE1394 or RS-232C, a parallel interface such as SCSI, IDE or IEEE1284, and an analog interface including a D/A converter and an A/D converter. The input section 523 composed of a keyboard and a mouse is connected to the I/O interface 521f and the user uses the input section 523 to input data to the computer 52a.

The communication interface 521g is an Ethernet (registered trade name) interface. The communication interface 521g is connected to the measuring unit 51 via a LAN. Thanks to the communication interface 521g, the computer 52a sends and receives data to and from the measuring unit 51 connected to the LAN by using a predetermined communication protocol.

The image output interface 521h is connected to the image display section 522 composed of a LCD or a CRT to output a picture signal corresponding to the image data provided from the CPU 521a to the image display section 522. The image display section 522 displays an image (screen) in accordance with an input picture signal.

<Configuration of Smear Preparing Apparatus 6>

The smear preparing apparatus 6 aspirates a blood sample so as to deliver it onto a slide glass by drops, spreads and dries the blood sample on the slide glass, and supplies a stain solution to the slide glass to stain the blood on the slide glass. In this manner, the smear preparing apparatus prepares a smear.

Figure 13:
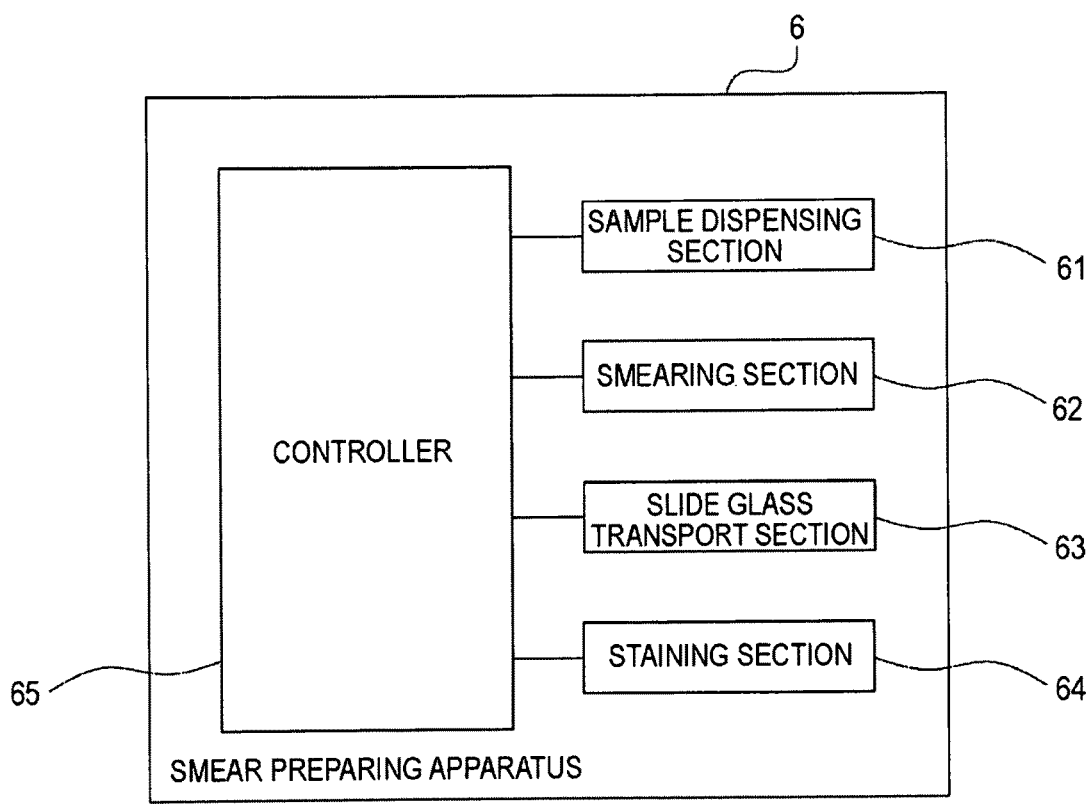
FIG. 13 is a block diagram showing the schematic configuration of a smear preparing apparatus.

FIG. 13 is a block diagram showing the schematic configuration of the smear preparing apparatus 6. As shown in FIG. 13, the smear preparing apparatus 6 includes a sample dispensing section 61, a smearing section 62, a slide glass transport section 63, a staining section 64 and a controller 65.

The sample dispensing section 61 is provided with an aspiration tube (not shown) and the aspiration tube is stuck into the lid 8a of the sample container 8 in the sample rack 9 transported on the measuring line 31a of the sample transport apparatus 3 to aspirate a blood sample from the sample container 8. The sample dispensing section 61 is configured to drop the aspirated blood sample onto a slide glass. The smearing section 62 is configured to smear and dry the blood sample dropped onto the slide glass and perform printing on the slide glass.

The slide glass transport section 63 is provided to receive the slide glass on which the blood sample is smeared by the smearing section 62 in a cassette (not shown) and to transport the cassette. The staining section 64 supplies a stain solution to the slide glass in the cassette transported to a staining position by the slide glass transport section 63. The controller 65 controls the sample dispensing section 61, the smearing section 62, the slide glass transport section 63 and the staining section 64 in accordance with a smear preparing instruction issued from the sample transport apparatus 3 so as to perform the above smear preparing operation. When preparing a smear is completed, the controller 65 transmits a notification of the completion of the preparation of the smear to the sample transport apparatus 3.

<Configuration of System Control Apparatus 7>

The system control apparatus 7 is composed of a computer and controls the entire blood sample analyzing system 1. The system control apparatus 7 receives a specimen ID and a rack ID from the sample putting apparatus 2 so as to obtain a measuring order from a host computer (not shown) by the specimen ID as a key. Furthermore, the system control apparatus 7 performs image processing of the images captured by and output from the cameras 225a and 225b to determine whether a blood sample in a storing container is coagulated and to detect a volume of the blood sample in the sample container. Moreover, the system control apparatus 7 transmits the measuring order to the sample transport apparatus 3.

The system control apparatus 7 is realized by a computer 7a. As shown in FIG. 12, the computer 7a includes a main body 71, an image display section 72 and an input section 73. The main body 71 includes a CPU 71a, a ROM 71b, a RAM 71c, a hard disk 71d, a reading device 71e, an I/O interface 71f, a communication interface 71g and an image output interface 71h. The CPU 71a, ROM 71b, RAM 71c, hard disk 71d, reading device 71e, I/O interface 71f, communication interface 71g and image output interface 71h are connected to each other by a bus 71j.

In the hard disk 71d, various computer programs for being executed in the CPU 71a, such as an operating system and an application program, and data which are used to execute the computer programs are installed. A system control program 74a to be described later is also installed in the hard disk 71d.

The reading device 71e is composed of a flexible disk drive, a CD-ROM drive, a DVD-ROM drive or the like and can read the computer program or data recorded in a portable recording medium 74. In the portable recording medium 74, the system control program 74a for prompting the computer to function as the system control apparatus 7 is stored. The computer 7a can read the system control program 74a from the portable recording medium 74 to install the system control program 74a in the hard disk 71d.

The I/O interface 71f is composed of, for example, a serial interface such as USB, IEEE1394 or RS-232C, a parallel interface such as SCSI, IDE or IEEE1284, and an analog interface including a D/A converter and an A/D converter. The input section 73 composed of a keyboard and a mouse is connected to the I/O interface 71f and the user uses the input section 73 to input data to the computer 52a. In addition, the cameras 225a and 225b provided in the above-described sample check unit 22 are connected to the I/O interface 71f to take the images captured by the cameras 225a and 225b.

The communication interface 71g is an Ethernet (registered trade name) interface. The communication interface 71g is connected to the sample putting apparatus 2, the sample transport apparatus 3, the sample storing apparatus 4 and the host computer (not shown) via a LAN. Via the communication interface 71g, the computer 7a sends and receives data to and from the above respective apparatuses connected to the LAN by using a predetermined communication protocol.

Since the other configurations of the system control apparatus 7 are the same as the configurations of the above-described information processing unit 52, a description thereof will be omitted.

[Operation of Blood Sample Analyzing System]

Hereinafter, an operation of the blood sample analyzing system 1 according to this embodiment will be described.

<Operation of Sample Putting Apparatus 2>

Figure 14A:
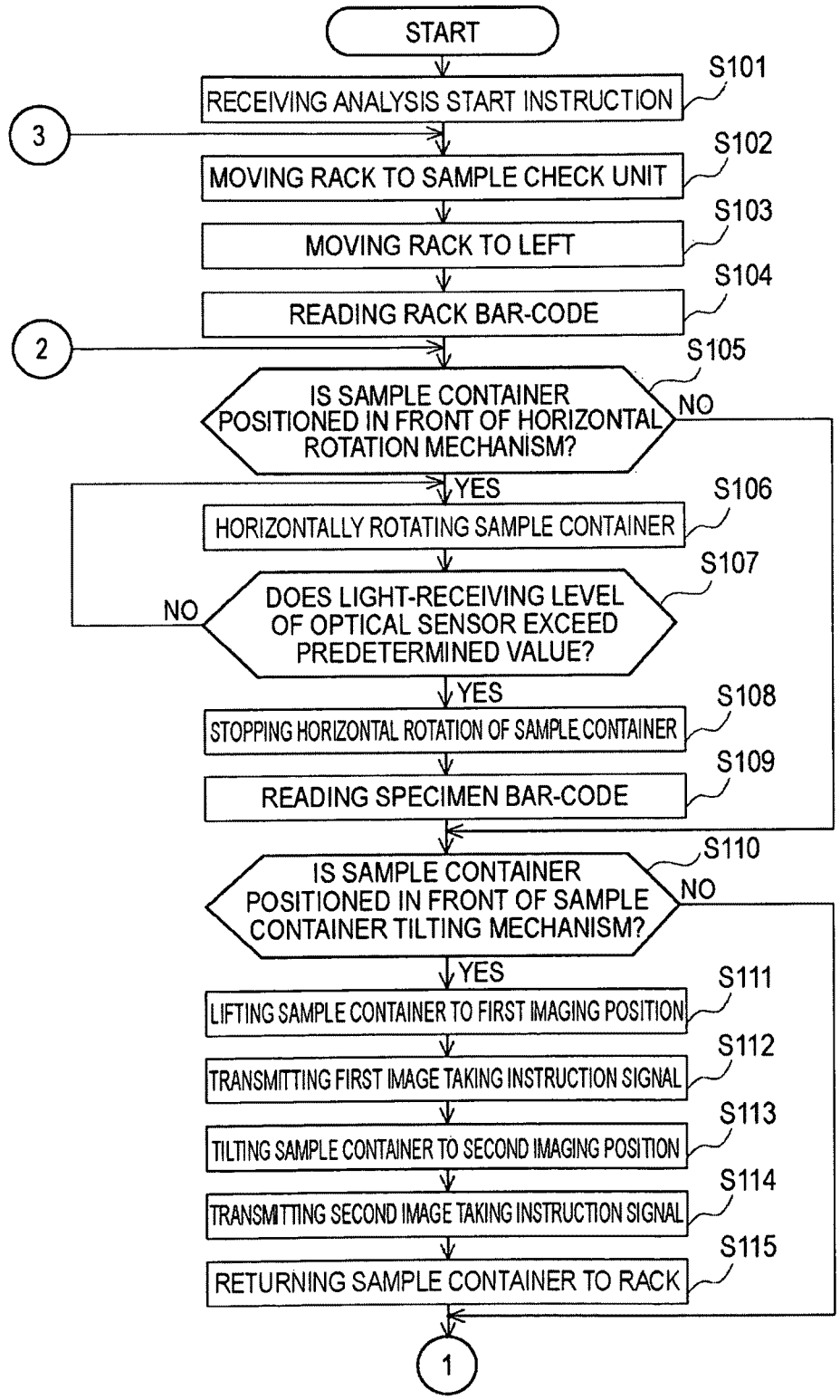
FIG. 14A is a flowchart (first half) showing the flow of an operation of a sample putting apparatus according to the first embodiment.
Figure 14B:
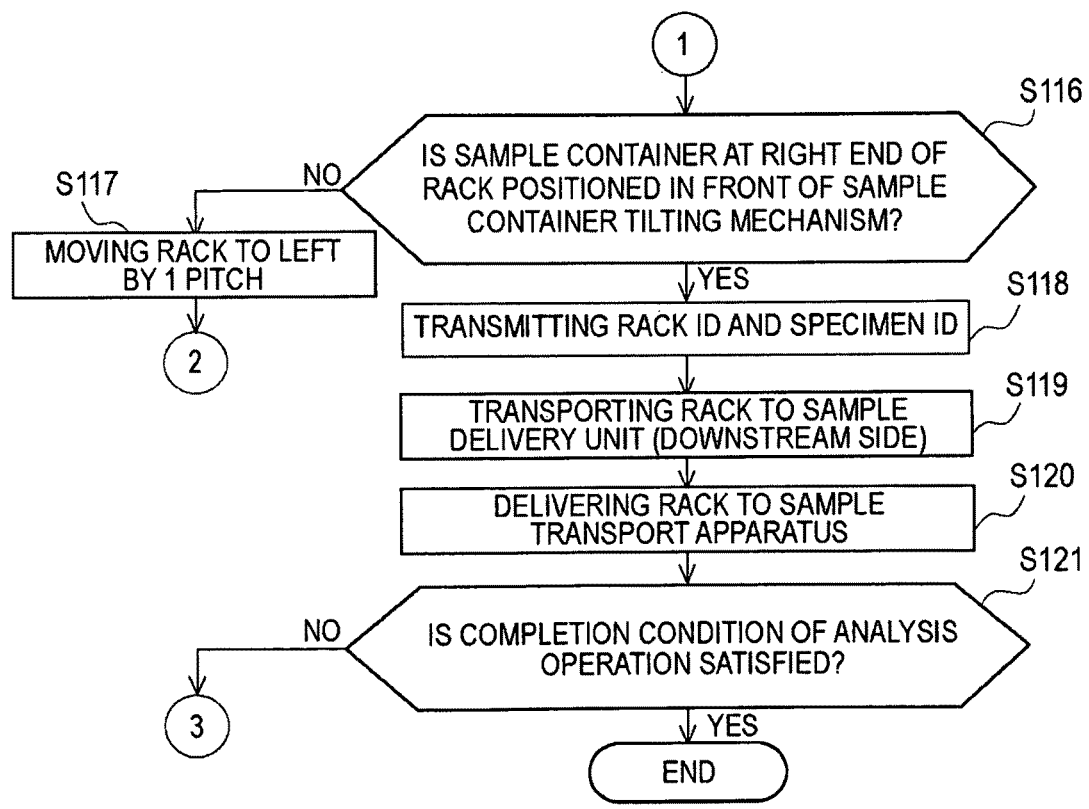
FIG. 14B is a flowchart (second half) showing the flow of the operation of the sample putting apparatus according to the first embodiment.

FIGS. 14A and 14B are flowcharts showing the flow of an operation of the sample putting apparatus 2. The user places the sample rack 9 storing the sample container 8 in the rack placing section 211 of the sample delivery unit 21a and operates the operating panel 214 of the sample delivery unit 21a to issue an instruction for analysis start to the blood sample analyzing system 1. The controller 213 of the sample delivery unit 21a receives the instruction for analysis start (Step S101) and starts movement of the sample rack 9 in accordance with the instruction (Step S102). The sample rack 9 placed in the rack placing section 211 of the sample delivery unit 21a is moved to the back on the rack placing section 211. Then, the sample rack 9 is moved to the left to be transferred to the sample check unit 22.

By the controller 226 of the sample check unit 22, the sample rack 9 fed to the sample check unit 22 is moved for every pitch to the left on the transport path of the rack placing section 221 (Step S103). A rack bar-code of the sample rack 9 is read by the bar-code reader 222a and provided to the controller 226 (Step S104). The controller 226 determines whether the sample container 8 is positioned in front of the horizontal rotation mechanism 223 (Step S105). This process is performed, by referring to, for example, a light-receiving level of the light-receiving element 223c of the optical sensor 223a. When the sample container 8 is not positioned in front of the horizontal rotation mechanism 223 (No in Step S105), the controller 226 returns the process to Step S110. On the other hand, when the sample container 8 is positioned in front of the horizontal rotation mechanism 223 (Yes in Step S105), the controller 226 compares the light-receiving level of the light-receiving element 223c of the optical sensor 223a with a predetermined value (Step S107), while bringing the contacting section 223d into contact with the lid 8a of the sample container 8 and rotating the contacting section (Step S106). When the light-receiving level is equal to or less than the predetermined value (No in Step S107), the controller returns the process to Step S106 and thus the horizontal rotation of the sample container 8 is continued. On the other hand, when the light-receiving level exceeds the predetermined value (Yes in Step S107), the controller 226 stops the horizontal rotation of the contacting section 223d (Step S108) and causes the bar-code reader 222b to read the specimen bar-code (Step S109).

Subsequently, the controller 226 determines whether the sample container 8 is disposed in front of the sample container tilting mechanism 224 (Step S110). This process is performed by, for example, determining how many times has the sample container 8 disposed in front of the horizontal rotation mechanism 223 been subjected to pitch feeding. When the sample container 8 is not disposed in front of the sample container tilting mechanism 224 (No in Step S110), the controller 226 performs a process of Step S116. When the sample container 8 is disposed in front of the sample container tilting mechanism 224 (Yes in Step S110), the controller 226 grasps the sample container 8 by the grasping section 224a to lift the sample container to the first imaging position on the upper side (Step S111), and transmits a first image taking instruction signal to the system control apparatus 7 (Step S112). As described later, the system control apparatus 7 takes an image captured by the camera 225a when receiving the first image taking instruction signal, and then performs image processing of the image and detects the blood volume in the sample container 8.

Next, the controller 226 vertically turns the grasping section 224a by a predetermined angle to tilt the sample container 8 to the second imaging position (Step S113) and transmits a second image taking instruction signal to the system control apparatus 7 (Step S114). As described later, the system control apparatus 7 takes an image captured by the camera 225b when receiving the second image taking instruction signal, and then performs image processing of the image and determines the presence or absence of blood coagulation in the sample container 8.

Next, the controller 226 turns the grasping section 224a in the counter direction to return the sample container 8 to the vertical state again, and moves the grasping section 224a downward to store the sample container 8 in the sample rack 9 (Step S115).

Herein, in order to simplify the description, the processes of Steps S105 to S109 and the processes of Steps S110 to S115 have been described so as to be sequentially performed. However, actually, the processes are performed in parallel. That is, for example, while one sample container 8 stored in the sample rack 9 is horizontally rotated, a different sample container 8 is pulled from the sample rack 9 of the sample containers 8.

The controller 226 determines whether all the sample containers 8 stored in the sample rack 9 have been subjected to the above processes, or more precisely, whether a sample container storing section at the right end of the sample rack 9 is positioned in front of the sample container tilting mechanism 224 (Step S116). When the right end of the sample rack 9 is not yet positioned in front of the sample container tilting mechanism 224 (No in Step S116), the controller moves the sample rack 9 to the left by one pitch (Step S117) and returns the process to Step S105.

When the right end of the sample rack 9 is positioned in front of the sample container tilting mechanism 224 (Yes in Step S116), the controller 226 transmits a rack ID of the sample rack 9 and specimen IDs of all the sample containers 8 stored in the sample rack 9 to the system control apparatus 7 (Step S118). In the data transmitted in Step S118, holding positions (1 to 10) of the sample containers 8 in the sample rack 9 correspond to the specimen IDs of the held sample containers. When the specimen ID cannot be obtained due to reading failure of the specimen bar-code, data indicating the reading failure of the specimen bar-code associated with the holding position is transmitted. Next, the controller 226 further moves the sample rack 9 to the left to deliver the sample rack 9 to the sample delivery unit 21b (Step S119). The controller 213 of the sample delivery unit 21b moves the received sample rack 9 (Step S120). The sample rack 9 is moved on the rack placing section 211 of the sample delivery unit 21b and then moved to the left to be transferred to the sample transport apparatus 3.

The controller 213 of the sample delivery unit 21a determines whether the conditions of the completion of the analysis operation (an analysis completion instruction is issued from the user, or the sample rack 9 is not on the rack placing section 211 of the sample delivery unit 21a) are satisfied (Step S121). When the conditions are not satisfied (No in Step S121), the controller returns the process to Step S102, and when the conditions are satisfied (Yes in Step S121), the controller completes the process.

<Measuring Order Obtaining Operation of System Control Apparatus 7>

Next, an operation of the system control apparatus 7 will be described. The system control apparatus obtains a measuring order of a specimen (blood sample) by the specimen ID received from the sample putting apparatus 2. Herein, the measuring order is data indicating an instruction of an analysis item for blood sample analysis, and includes attribute information of the specimen, such as the specimen ID, patient ID and name of the patient, and information of the analysis item.

Figure 15:
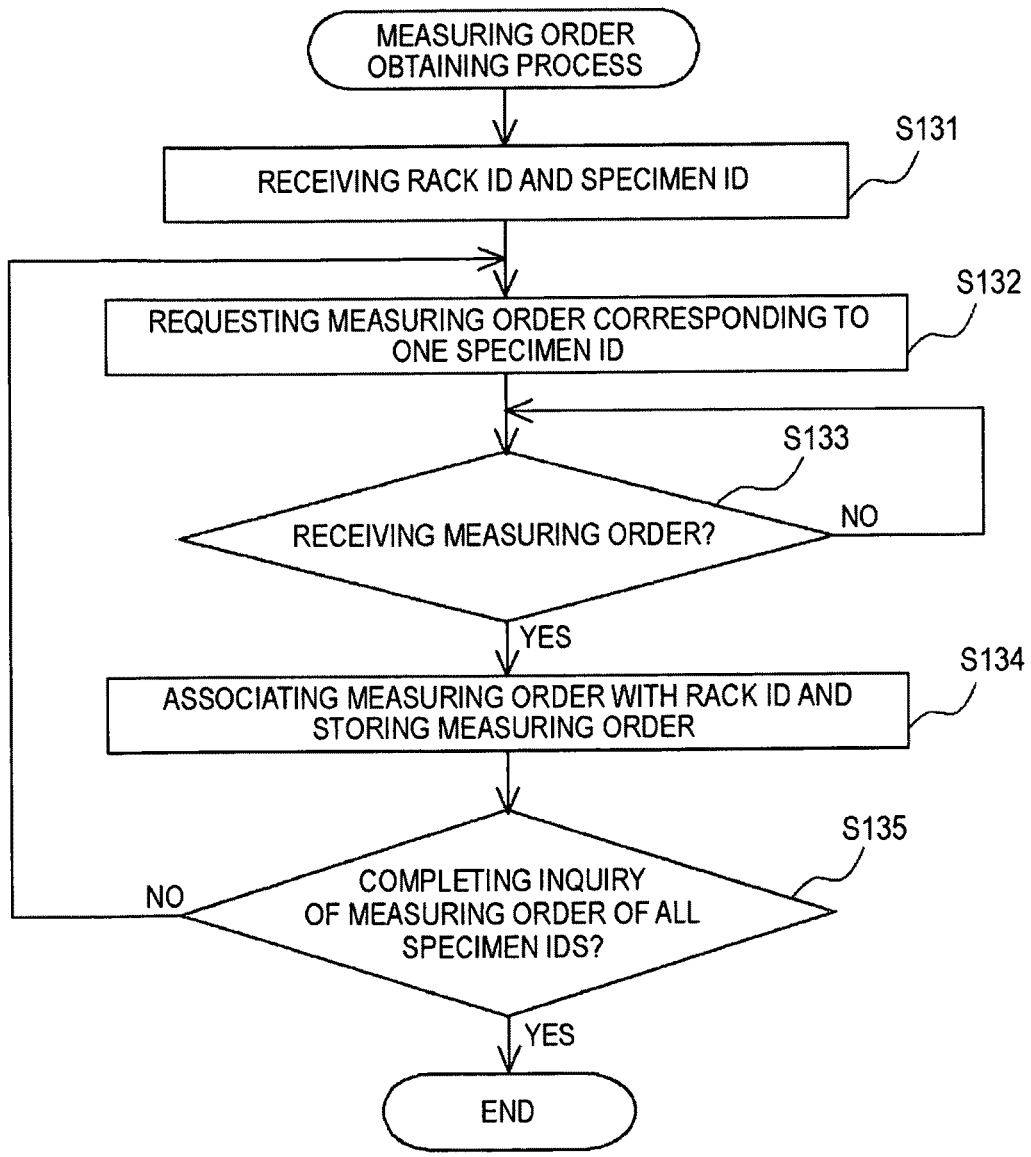
FIG. 15 is a flowchart showing the procedure of a measuring order obtaining process of a system control apparatus according to the first embodiment.

FIG. 15 is a flowchart showing the procedure of a process of obtaining a measuring order. As shown in FIG. 15, when the system control apparatus 7 receives the rack ID and specimen IDs transmitted from the sample putting apparatus 2 (Step S131), an interrupt request is generated for the CPU 71a of the system control apparatus 7 and a process of Step S132 is invoked.

In Step S132, the CPU 71a transmits one of the received specimen IDs and requests a measuring order corresponding to the specimen ID from a host computer (not shown) (Step S132). The CPU 71a stands by to receive the measuring order (No in Step S133), and when the system control apparatus 7 receives the measuring order transmitted from the host computer (Yes in Step S133), the CPU associates the received measuring order with the rack ID and stores the measuring order in the hard disk 71d (Step S134). The CPU 71a determines whether the specimen IDs corresponding to the rack ID, that is, all the specimen IDs of all the sample containers 8 stored in the sample rack 9 having the rack ID have been subjected to an inquiry of measuring order (Step S135). When there is the specimen ID not subjected to the inquiry of measuring order (No in Step S135), the CPU 71a returns the process to Step S132 and requests a measuring order corresponding to the specimen ID not yet subjected to the inquiry of measuring order from the host computer.

On the other hand, when all the specimen IDs have been subjected to the inquiry of measuring order (Yes in Step S135), the CPU 71a completes the process.

<Blood Volume Detecting Operation of System Control Apparatus 7>

In addition, the system control apparatus 7 takes an image captured by the camera 225a and performs image processing of the image to detect a blood volume in the sample container 8.

Figure 16:
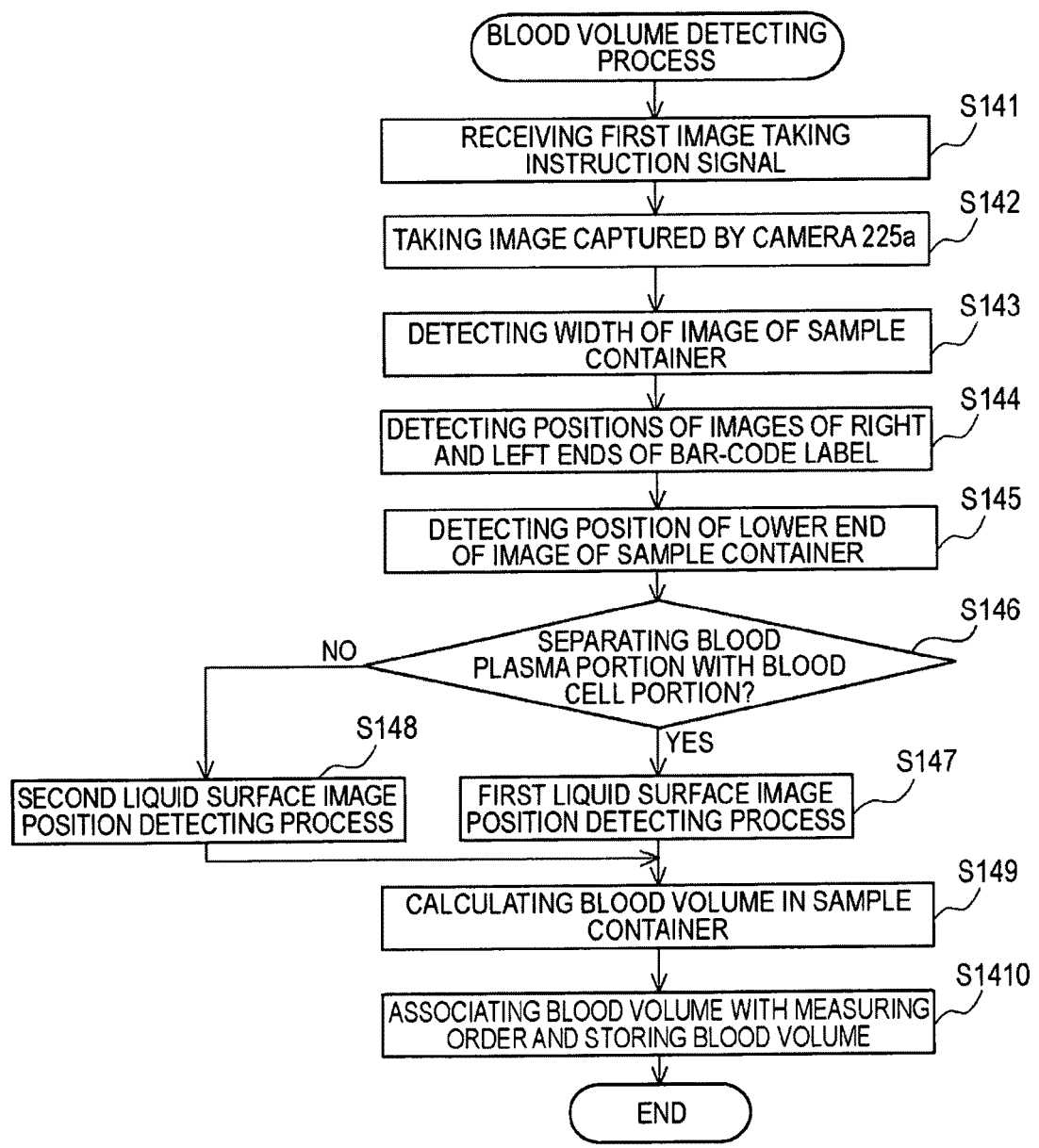
FIG. 16 is a flowchart showing the procedure of a blood volume detecting process of the system control apparatus according to the first embodiment.

FIG. 16 is a flowchart showing the procedure of a blood volume detecting process. As shown in FIG. 16, when the system control apparatus 7 receives the first image taking instruction signal transmitted from the sample putting apparatus 2 (Step S141), an interrupt request is generated for the CPU 71a of the system control apparatus 7 and a process of Step S142 is invoked.

Figure 17:
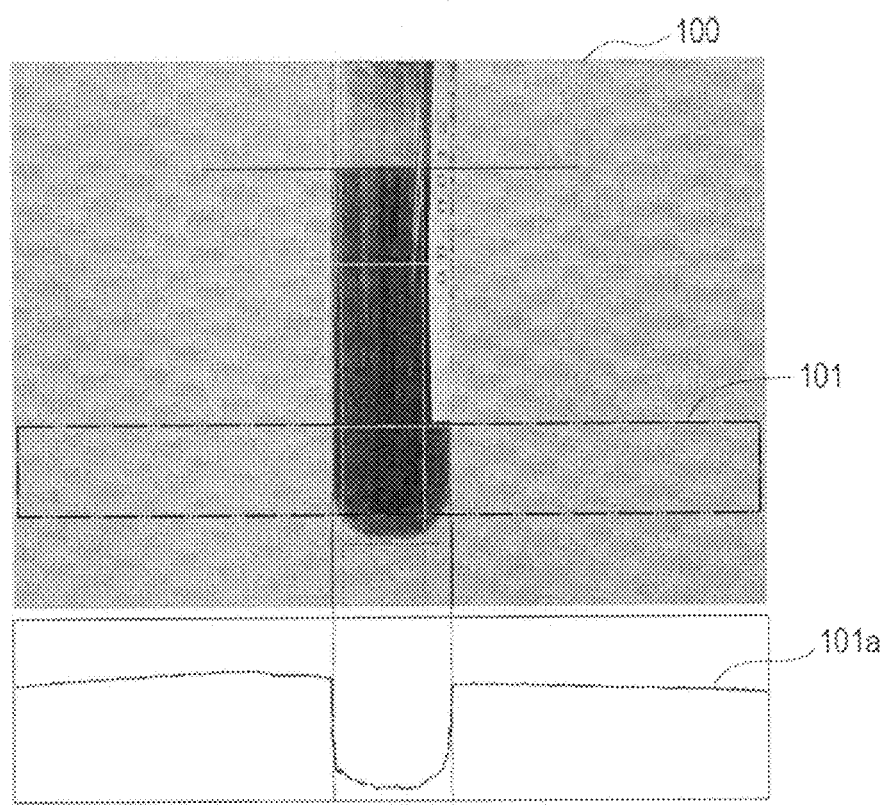
FIG. 17 is a schematic diagram for illustrating a process of detecting a width of an image of the sample container.

In Step S142, the CPU 71a takes the image captured by the camera 225a at that time (Step S142). Next, the CPU 71a detects a width of an image of the sample container 8 in the taken image (Step S143). This process will be described in detail. FIG. 17 is a schematic diagram for illustrating a process of detecting the width of the image of the sample container 8. An image 100 is a color image and has luminance information of RGB of respective pixels. A processing area 101 for obtaining the width of the sample container 8 in the image 100 is subjected to the following process by the CPU 71a. The processing area 101 is a predetermined area, which includes an image of the vicinity of the bottom portion of the sample container 8 and not includes an image of the bar-code label. For each X coordinate in the processing area 101, the CPU 71a accumulates B (blue) luminance values (hereinafter, referred to as "B value") of the pixels in a Y direction in the processing area 101. That is, an accumulation value (hereinafter, referred to as "B luminance accumulation value") of the B values of the pixels in a column of pixel groups at the left end included in the processing area 101 is calculated, and a B luminance accumulation value of a column of pixel groups on the right side thereof is calculated. This operation is repeated until reaching the right end of the processing area 101 while incrementing an X coordinate value.

In FIG. 17, a graph of the B luminance accumulation value obtained as described above in the processing area 101 is denoted by reference numeral 101a. The B luminance accumulation value related to the processing area 101 is high in a background image and is low in the image of the sample container 8. Accordingly, the CPU 71a differentiates the B luminance accumulation value in an X direction and detects a portion in which the B luminance accumulation value is sharply lowered and a portion in which the B luminance accumulation value sharply increases. In this manner, the width of the sample container 8 is detected.

Figure 18:
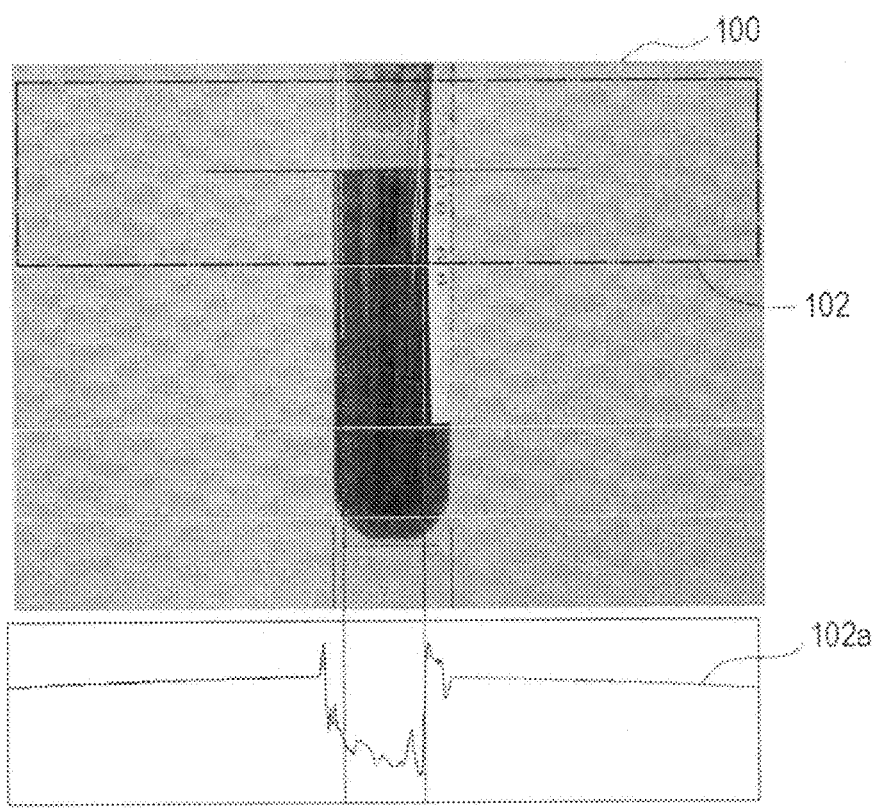
FIG. 18 is a schematic diagram for illustrating a process of detecting positions of the right and left ends of an image of a bar-code label.

Next, the CPU 71a detects positions of images of the right and left ends of the bar-code label 8b (Step S144). This process will be described in detail. FIG. 18 is a schematic diagram for illustrating a process of detecting positions of the right and left ends of an image of the bar-code label 8b. A processing area 102 for detecting the positions of the right and left ends of the image of the bar-code label 8b in the image 100 is subjected to the following process by the CPU 71a. The processing area 102 is a predetermined area, which is an upper portion in the image and includes the image of the bar-code label. For each X coordinate value in the processing area 102, the CPU 71a calculates a B luminance accumulation value. In the drawing, a graph of the B luminance accumulation value in the processing area 102 is denoted by reference numeral 102a. As shown by the graph 102a, the B luminance accumulation value related to the image of the bar-code label is higher than the B luminance accumulation value related to the background image and the image of the sample container. Accordingly, the CPU 71a scans the B luminance accumulation value from the left to the right and detects as the position of the image of the left end of the bar-code label a position where the B luminance accumulation value becomes high and then is sharply lowered. Then, the CPU scans the B luminance accumulation value from the right to the left and detects as the position of the image of the right end of the bar-code label a position where the B luminance accumulation value becomes high and then is sharply lowered.

Figure 19:
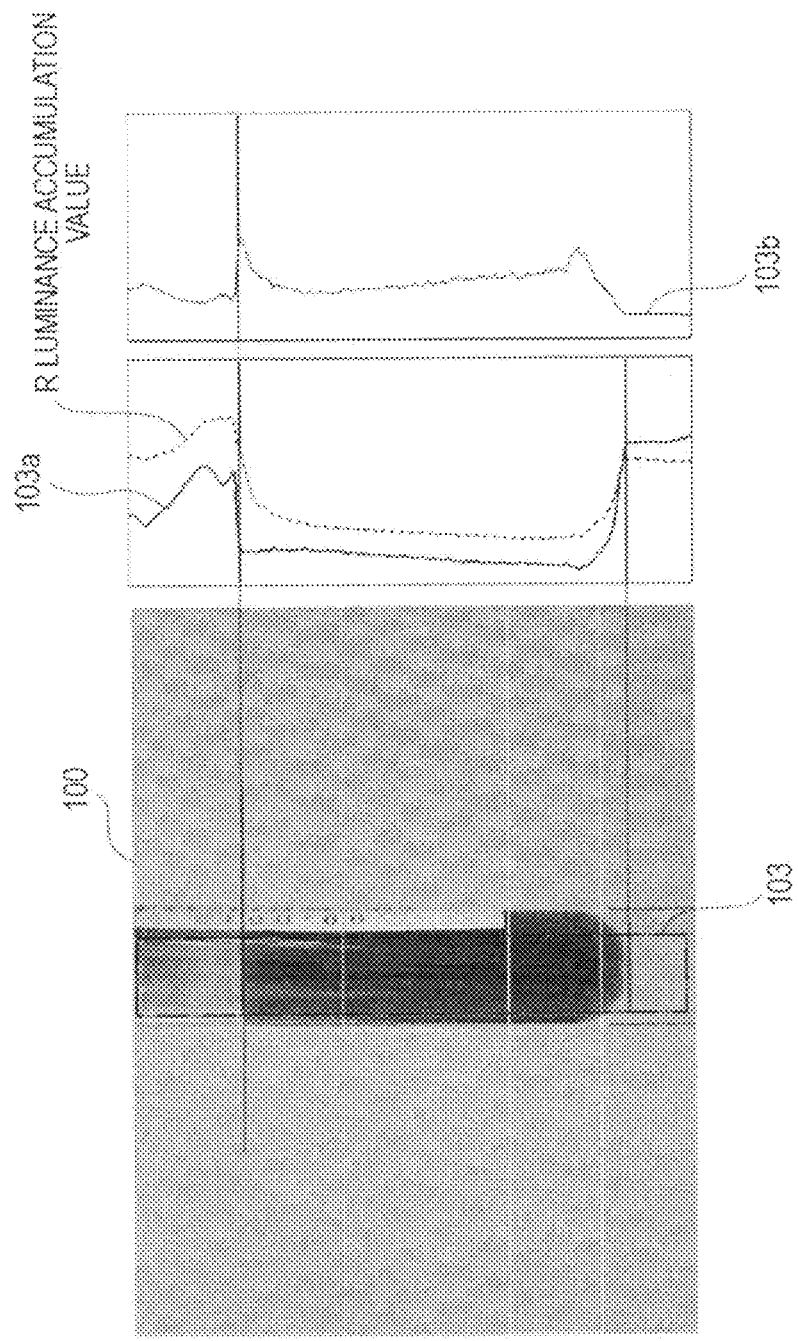
FIG. 19 is a schematic diagram for illustrating a process of detecting a position of the lower end of the image of the sample container.

Next, the CPU 71a detects a position of the lower end of the image of the sample container (Step S145). This process will be described in detail. FIG. 19 is a schematic diagram for illustrating a process of detecting a position of the lower end of the image of the sample container. First, the CPU 71a determines a processing area 103 for detecting the position of the lower end of the image of the sample container and a position of an image of a liquid surface of the blood sample in the image 100. The processing area 103 is an area at the slightly inner side from an area surrounded by the positions of the images of the right and left ends of the bar-code label detected in Step S144. This is because, the image of the bar-code label does not exist in the area between the image of the left end and the image of the right end of the bar-code label.

For each Y coordinate value in the processing area 103, the CPU 71a calculates a B luminance accumulation value by accumulating B values in an X direction, and calculates an R luminance accumulation value by accumulating R values. In addition, for each Y coordinate, the CPU 71a calculates a value (hereinafter, referred to as "R/B accumulation luminance ratio") which is obtained by dividing the R luminance accumulation value by the B luminance accumulation value. In the drawing, a graph of the B luminance accumulation value in the processing area 103 is denoted by reference numeral 103a and a graph of R/B in the processing area 103 is denoted by reference numeral 103b. As shown by the graph 103a, the B luminance accumulation value of the image of the blood sample in the sample container is lower than the B luminance accumulation values of the background image and an image of a portion in which the blood sample in the sample container does not exist. Moreover, in the image of the blood sample, the R/B accumulation luminance ratio is higher than in the other portion. Accordingly, the CPU 71a differentiates the B luminance accumulation value in a Y direction, and detects as the position of the lower end of the image of the sample container a position where the B luminance accumulation value is sharply lowered in a direction toward the upper side from the lower end of the processing area 103.

Next, the CPU 71a determines whether a blood plasma portion and a blood cell portion are separated in the blood sample (Step S146). In this process, it is determined that the blood plasma portion and the blood cell portion are separated, when the B luminance accumulation value and the R luminance accumulation value of the processing area 103 are scanned from the position of the lower end of the image of the sample container to the upper side and only the R luminance accumulation value is large.

When the blood plasma portion and the blood cell portion are separated (Yes in Step S146), the CPU 71a performs a first liquid surface image position detecting process of detecting the position of the image of the liquid surface of the blood sample (Step S147). When the blood plasma portion and the blood cell portion are not separated (No in Step S146), the CPU performs a second liquid surface image position detecting process of detecting the position of the image of the liquid surface of the blood sample (Step S148). In the first liquid surface image position detecting process, a position, where the B luminance accumulation value becomes large sharply in a direction toward the upper side from the image of the blood sample and the R/B accumulation luminance ratio is equal to or less than a predetermined value, is detected as the position of the image of the liquid surface. In the second liquid surface image position detecting process, a position, where the B luminance accumulation value becomes large sharply in a direction toward the upper side from the image of the blood sample, is detected as the position of the image of the liquid surface.

Next, the CPU 71a calculates the blood volume in the sample container 8 (Step S149). In this process, the CPU 71a calculates a blood volume BV by the following expressions (1) and (2).

$$R=(k \cdot W-2T)/2 \qquad (1)$$

$$BV=\pi R^2 \times (k \cdot H - R) + 2\pi R^3/3 \qquad (2)$$

R denotes a radius of an inner face of a sample container, k denotes a coefficient determined by scale of a captured image, W denotes a width of an image of a sample container, T denotes a thickness of a sample container and H denotes a height (a difference between a position of an image of a liquid surface and a position of an image of the lower end of a sample container) of an image of a blood sample. When calculating the blood volume BV, the CPU 71a associates the blood volume with the measuring order having the specimen ID of the blood sample as a target of imaging process and stores the blood volume in the hard disk 71*d* (Step S1410), and then completes the process.

<Blood Coagulation Determining Operation of System Control Apparatus 7>

The system control apparatus 7 takes an image captured by the camera 225*b* and performs image processing of the image to determine whether the blood sample in the sample container 8 is coagulated.

Figure 20:
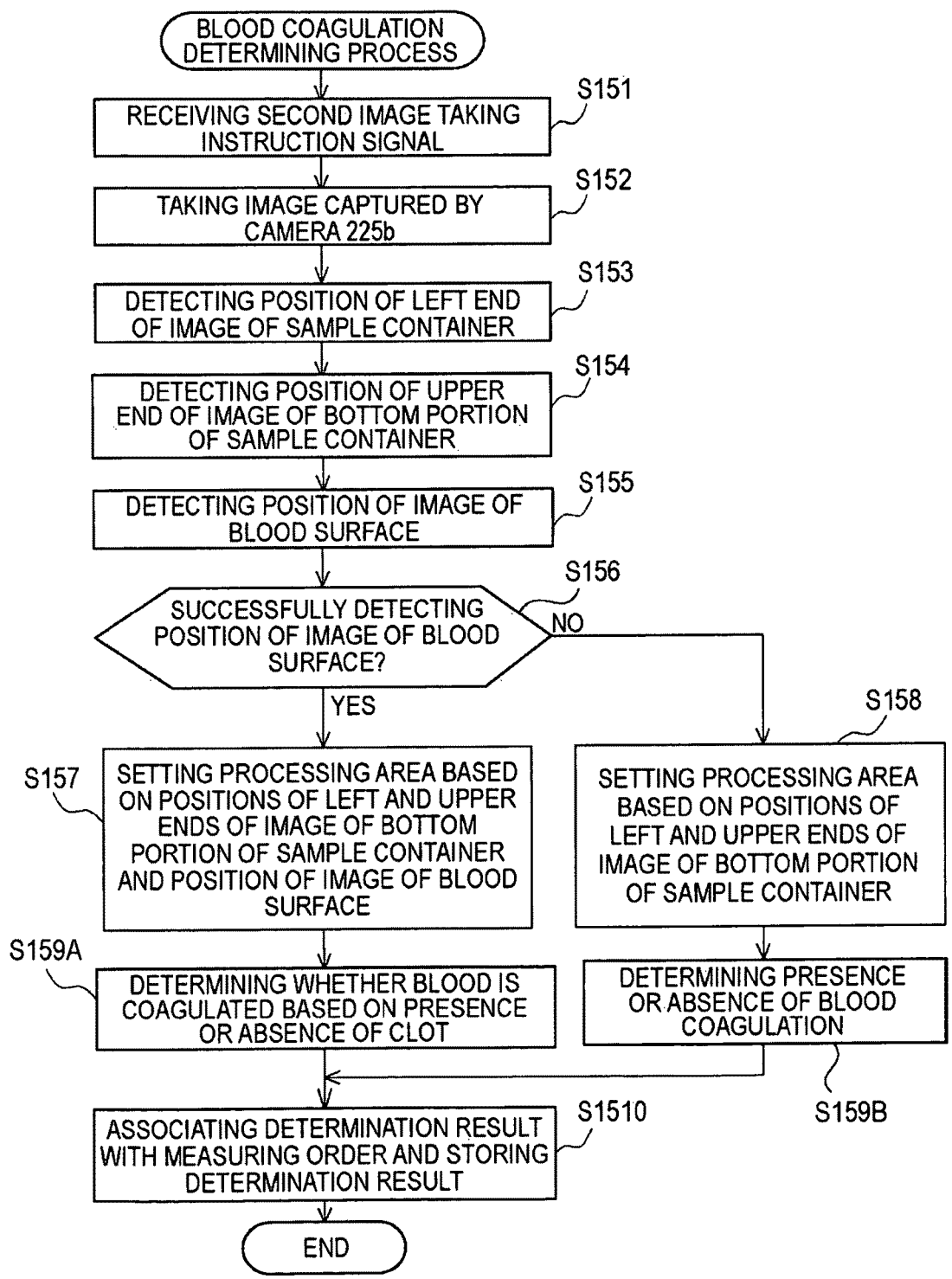
FIG. 20 is a flowchart showing the procedure of a blood coagulation determining process of the system control apparatus according to the first embodiment.

FIG. 20 is a flowchart showing the procedure of a blood coagulation determining process. As shown in FIG. 20, when the system control apparatus 7 receives the second image taking instruction signal transmitted from the sample putting apparatus 2 (Step S151), an interrupt request is generated for the CPU 71*a* of the system control apparatus 7 and a process of Step S152 is invoked.

Figure 21:
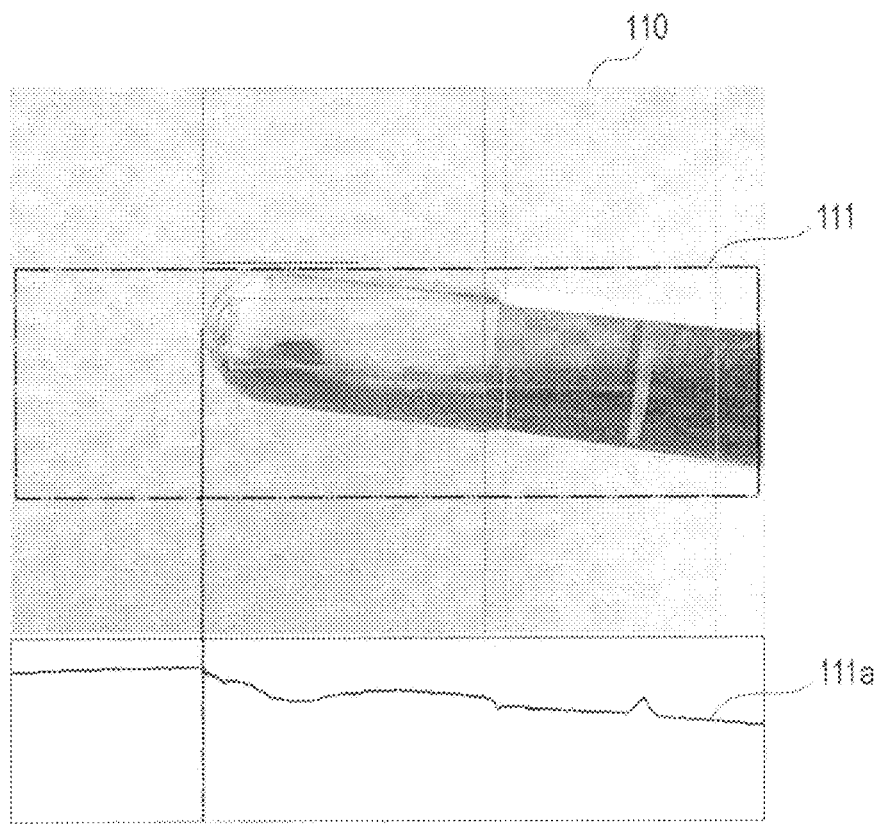
FIG. 21 is a schematic diagram for illustrating a process of detecting a position of the left end of the image of the sample container.

In Step S152, the CPU 71*a* takes the image captured by the camera 225*b* at that time (Step S152). Next, the CPU 71*a* detects a position of the left end of an image of the sample container 8 in the taken image (Step S153). This process will be described in detail. FIG. 21 is a schematic diagram for illustrating a process of detecting the position of the left end of the image of the sample container 8. An image 110 is a color image and has luminance information of RGB of respective pixels. A processing area 111 for obtaining the position of the left end of the image of the sample container 8 in the image 110 is subjected to the following process by the CPU 71*a*. The processing area 111 is a predetermined area, which includes an image of the vicinity of the bottom portion of the sample container 8. For each X coordinate, the CPU 71*a* calculates a B luminance accumulation value in a Y direction in the processing area 111. In the drawing, a graph of the B luminance accumulation value in the processing area 111 is denoted by reference numeral 111*a*. As shown by the graph 111*a*, the B luminance accumulation value related to the image of the sample container is lower than the B luminance accumulation value related to a background image. Accordingly, the CPU 71*a* differentiates the B luminance accumulation value in an X direction and detects as the position of the left end of the image of the sample container a position where the B luminance accumulation value scanned from the left to the right is lowered.

Figure 22:
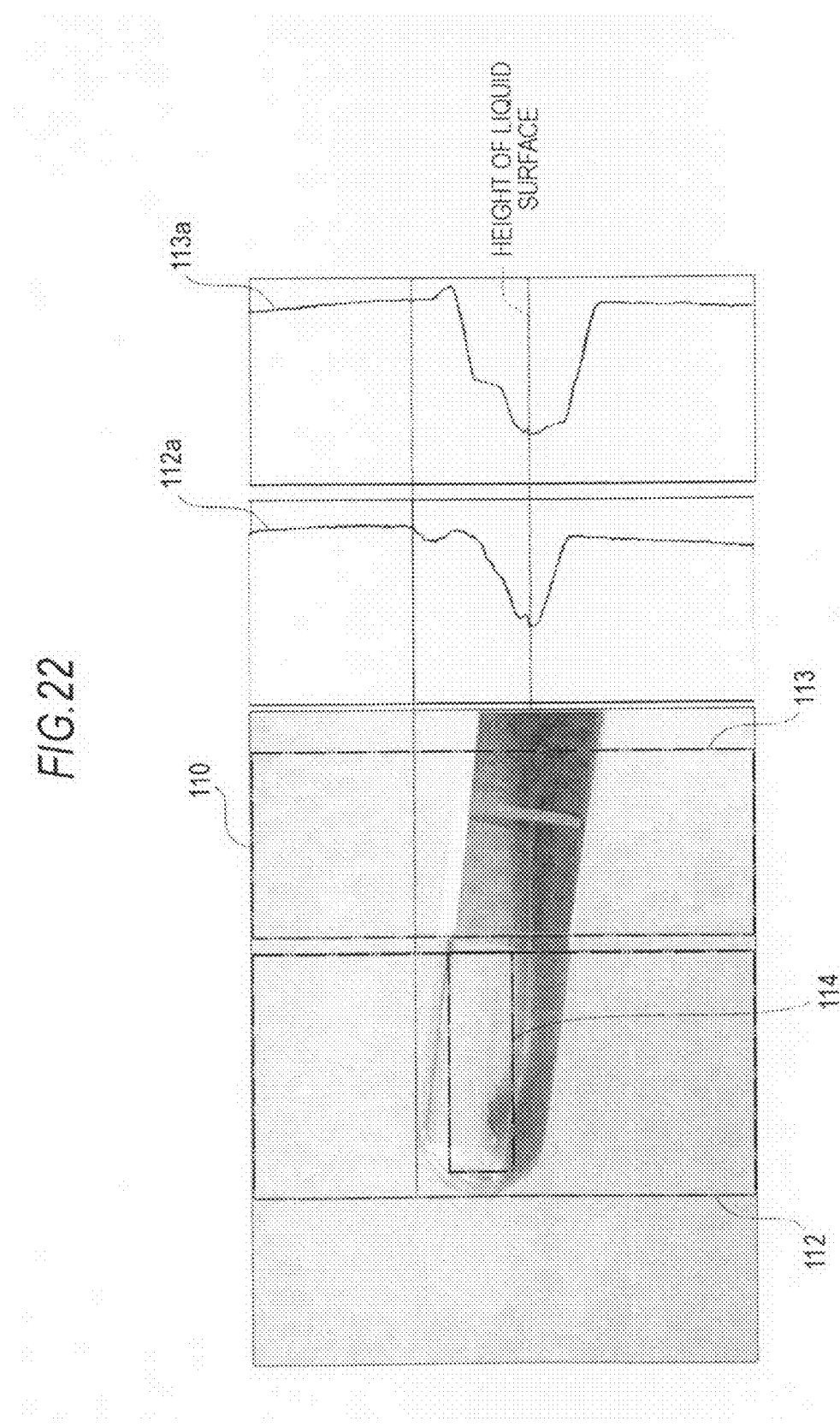
FIG. 22 is a schematic diagram for illustrating a process of detecting a position of the upper end of an image of a bottom portion of the sample container.

Next, the CPU 71*a* detects a position of the upper end of the image of the bottom portion of the sample container (Step S154). This process will be described in detail. FIG. 22 is a schematic diagram for illustrating a process of detecting the position of the upper end of the image of the bottom portion of the sample container. The CPU 71*a* determines a processing area 112 for detecting the position of the upper end of the image of the bottom portion of the sample container in the image 110. The processing area 112 is an area from the position of the left end of the image of the sample container detected in Step S153 to a position positioned on the right side thereof by a predetermined number of pixels. This is because, since the sample container 8 is imaged in a state in which the bottom portion of the sample container 8 is positioned higher than the lid 8*a* in the image, and it is required that the image of the bottom portion of the sample container is included in the processing area so that the bottom portion of the sample container 8 becomes the upper end of the sample container, the image of the bottom portion of the sample container 8 exists in an area on the right side of the position of the left end.

For each Y coordinate, the CPU 71*a* calculates a B luminance accumulation value in the X direction in the processing area 112. In the drawing, a graph of the B luminance accumulation value in the processing area 112 is denoted by reference numeral 112*a*. As shown by the graph 112*a*, the B luminance accumulation value related to the image of the sample container is lower than the B luminance accumulation value related to the background image. Accordingly, the CPU 71*a* differentiates the B luminance accumulation value in the Y direction, and detects as the position of the upper end of the image of the bottom portion of the sample container a position where the B luminance accumulation value is lowered when the B luminance accumulation value is scanned from the upper side to the lower side.

Next, the CPU 71*a* detects the position of the image of the liquid surface of the blood sample (Step S155). This process will be described in detail. The CPU 71*a* subjects a processing area 113 (see FIG. 22 for reference) for detecting the position of the image of the liquid surface of the blood sample in the image 110 to the following process. The processing area 113 is a predetermined area, which is positioned on the right side in the image 110. When the blood sample contains a clot formed by the aggregation of blood, the clot usually sinks to the bottom portion of the sample container 8 due to a weight thereof. Accordingly, when the sample container 8 is tilted to the second imaging position where the bottom portion of the sample container 8 is positioned on the left side in a front view, the blood sample in the sample container 8 moves toward the lid 8*a* (right side) of the sample container 8 and the blood sample in the bottom portion of the sample container 8 decreases. The clot sinking to the bottom of the sample container 8 rides on the inner face of the bottom portion of the sample container 8 and protrudes from the liquid surface of the shallow blood sample. Thus, only the liquid blood exists in the area on the right side in the image 110. The processing area 113 is provided in this portion and thus the processing area 113 includes an image of the liquid blood without an image of the clot. Accordingly, the processing area 113 is suitable for detection of the image of the liquid surface which is an image of a surface of liquid. For each Y coordinate value in the processing area 113, the CPU 71*a* calculates a B luminance accumulation value and an R luminance accumulation value. In the drawing, a graph of the B luminance accumulation value in the processing area 113 is denoted by reference numeral 113*a*. First, the CPU 71*a* sequentially checks an R/B accumulation luminance ratio toward the upper side from the lower end of the processing area 113 and determines whether the R/B accumulation luminance ratio is equal to or greater than a predetermined value. Herein, the R/B accumulation luminance ratio is large in the blood image. Accordingly, when the R/B accumulation luminance ratio is equal to or greater than the predetermined value, it can be determined that the blood is in the sample container. When it can be determined that the blood is not in the sample container, that is, when the R/B accumulation luminance ratio does not exceed the predetermined value in a direction of a Y axis of the entire processing area 113, it is regarded that detection of the position of the image of the liquid surface of the blood sample failed.

When it can be determined that the blood exists, the CPU 71*a* checks the B luminance accumulation value toward the upper side from a position (the R/B accumulation luminance ratio is equal to or greater than the predetermined value) where it is considered that the blood exists to detect a position, where a differential value of the B luminance accumulation value is equal to or greater than a predetermined value and the R/B accumulation luminance ratio is equal to or less than a predetermined value, as the position of the image of the blood surface. When there is not such a position, it is regarded that detection of the position of the image of the blood surface failed.

Next, the CPU 71*a* determines whether the detection of the position of the image of the blood surface in Step S155 is succeeded (Step S156). When the detection of the position of the image of the blood surface is succeeded (Yes in Step S156), a processing area for determining the presence or absence of blood coagulation is set based on the positions of the left and right ends of the image of the bottom portion of the sample container and the position of the image of the blood surface (Step S157). This processing area will be described with reference to FIG. 22. In the process of Step S157, a processing area 114, which is positioned on the right side of the left end of the image of the bottom portion of the sample container, on the lower side of the upper end of the image of the bottom portion of the sample container, and on the upper side of the image of the blood surface, is set. As shown in FIG. 22, when the blood is coagulated, the clot protrudes upward from the liquid surface in some cases. In this case, the image of the clot is in the processing area 114 positioned on the upper side of the image of the liquid surface. The processing area 114 is subjected to image processing and thus the coagulation of the blood can be detected.

Figure 23:
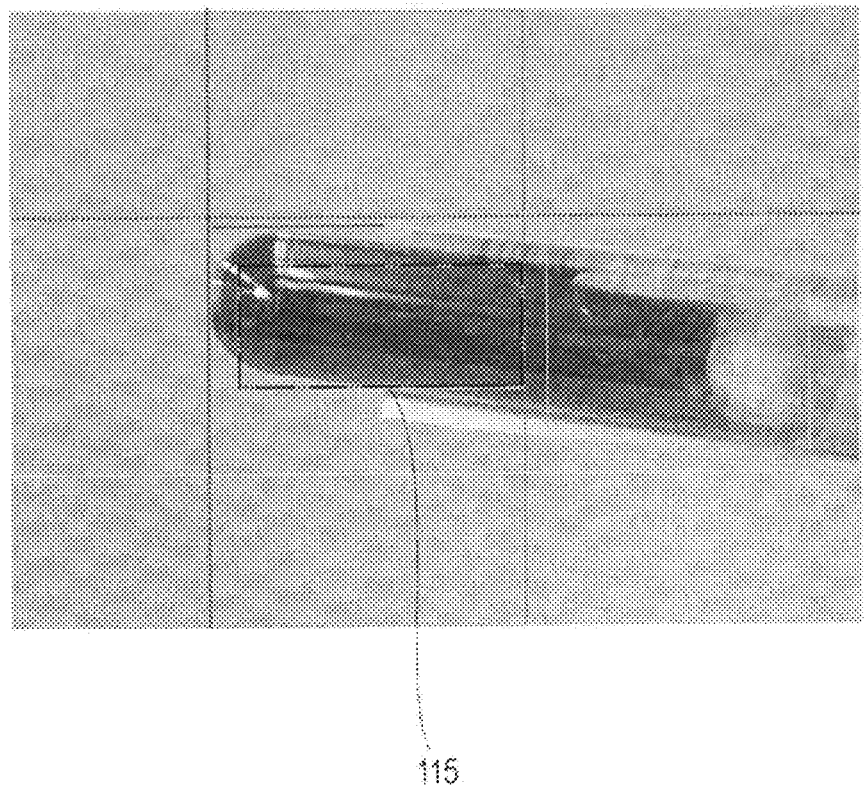
FIG. 23 is a schematic diagram for illustrating a processing area for determining blood coagulation when detection of a position of an image of a blood surface fails.

On the other hand, when the detection of the position of the image of the blood surface fails (No in Step S156), a processing area for determining the presence or absence of blood coagulation is set based on the positions of the left and right ends of the image of the bottom portion of the sample container (Step S158). FIG. 23 is a schematic diagram for illustrating a processing area for determining blood coagulation when the detection of the position of the image of the blood surface fails. As shown in FIG. 23, a processing area 115 having a predetermined size is positioned on the right side of the left end of the image of the bottom portion of the sample container and on the lower side of the upper end of the image of the bottom portion of the sample container in this case. When it can be determined that the blood exists and the position of the image of the blood surface cannot be detected, the blood has viscosity due to coagulation and adheres to the inner face of the sample container in some cases. In this case, the liquid surface cannot be confirmed even if the sample container 8 is tilted, and the blood image occupies a large portion of the processing area 115. The processing area 115 is subjected to image processing and thus the coagulation of the blood can be detected.

After setting the processing area for detecting blood coagulation, the CPU 71a determines the presence or absence of blood coagulation (Steps S159A and 159B). This process will be described as follows. In Step S159A, for each pixel included in the processing area 114, the CPU 71a calculates an R/B luminance ratio which is a ratio of an R value to a B value of a single pixel. In addition, the CPU 71a counts the number of pixels, each of which has the B value equal to or less than a predetermined value and the R/B luminance ratio equal to or less than a predetermined value, among all the pixels included in the processing area 114. When the number of pixels is equal to or greater than a predetermined value, that is, when a clot protrudes from the blood surface, it is determined that the blood is coagulated. When the number of pixels is less than the predetermined value, that is, when a clot does not protrude from the blood surface, it is determined that the blood is not coagulated. In this manner, the presence or absence of blood coagulation is determined based on whether the clot protrudes from the blood surface, and thus the presence or absence of blood coagulation can be determined with higher accuracy than in the case where the presence or absence of coagulation is determined based on a difference between an area of a blood portion in a state in which the sample container is vertically held and an area of a blood portion in a state in which the sample container is tilted. Moreover, since the blood coagulation can be determined from one captured image, processing power of the blood sample analyzing system 1 can be enhanced. In Step S159B, the CPU 71a subjects the pixels included in the processing area 115 to the same process as the coagulation determining process in Step S159A, and in this manner, blood coagulation is determined.

Figure 24A:
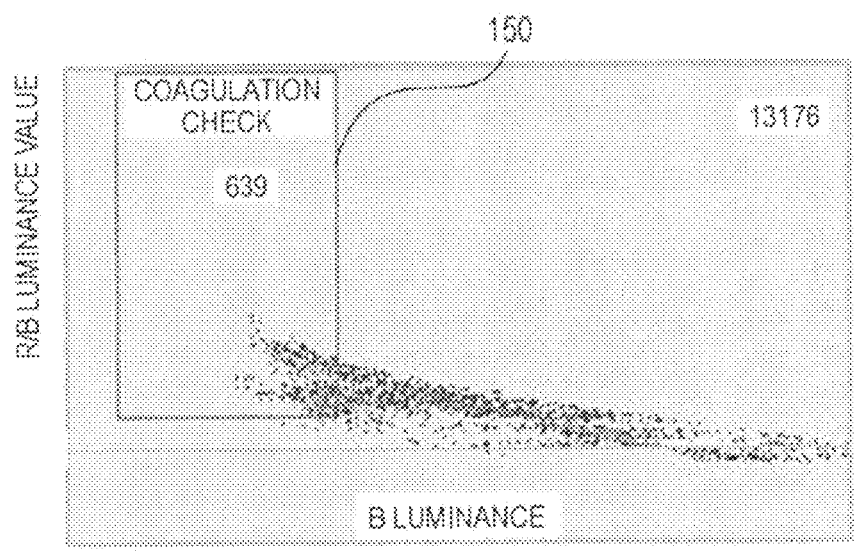
FIG. 24A is a scattergram showing a distribution state related to B values and R/B luminance ratios of pixels in the processing area in the image shown in FIG. 22.
Figure 24B:
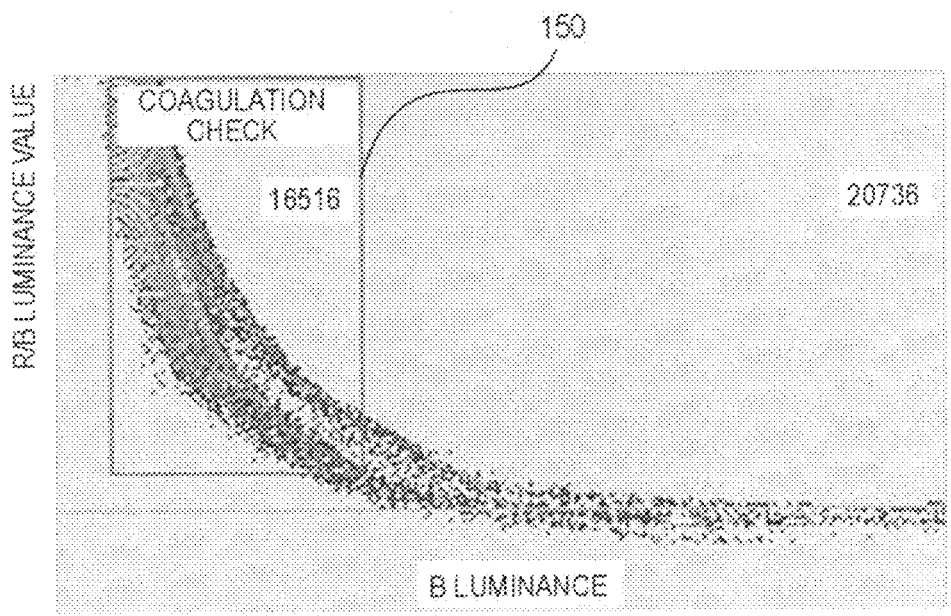
FIG. 24B is a scattergram showing a distribution state related to B values and R/B luminance ratios of pixels in the processing area in the image shown in FIG. 23.
Figure 24C:
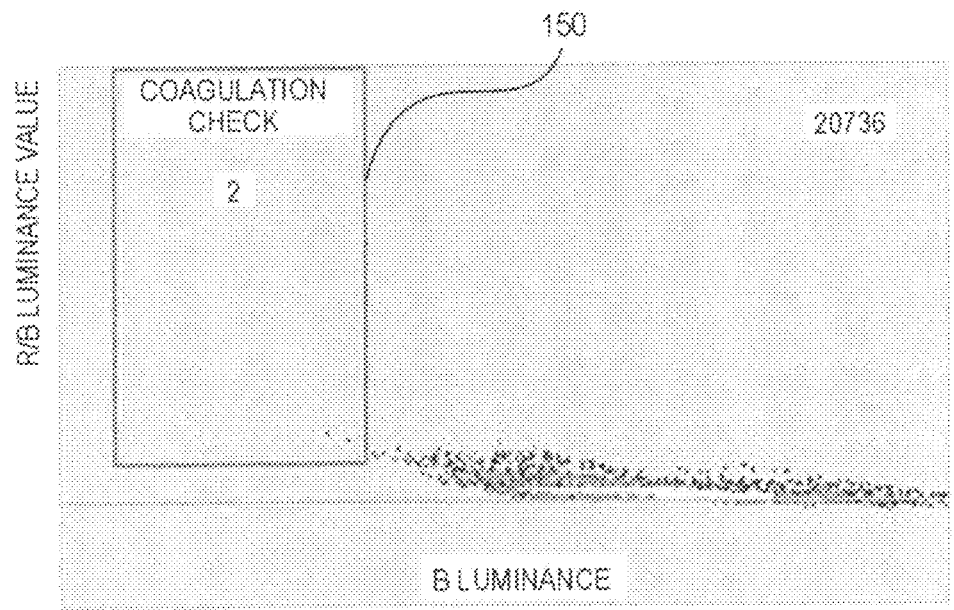
FIG. 24C is a scattergram showing a distribution state related to B values and R/B luminance ratios of pixels in the processing area for blood which is not coagulated.

FIG. 24A is a scattergram showing a distribution state related to the B values and the R/B luminance ratios of the pixels in the processing area 114 in the image shown in FIG. 22, FIG. 24B is a scattergram showing a distribution state related to the B values and the R/B luminance ratios of the pixels in the processing area 115 in the image shown in FIG. 23, and FIG. 24C is a scattergram showing a distribution state related to the B values and the R/B luminance ratios of the pixels in the processing area 114 for the blood which is not coagulated. In these drawings, a range satisfying the condition that the B luminance value is equal to or less than a predetermined value and the R/B luminance ratio is equal to or less than a predetermined value is represented by a rectangular frame 150. As shown in FIG. 24A, when a clot protrudes on a blood surface, a large number of pixels (several hundreds or more of pixels when the image 100 has a size of 640×480 dots) in all the pixels included in the processing area 114 satisfy the above condition. In addition, as shown in FIG. 24B, when it can be determined that blood exists and a position of an image of a blood surface cannot be detected, a very large number of pixels (10,000 pixels or more when the image 100 has a size of 640×480 dots) in all the pixels included in the processing area 115 satisfy the above condition. On the other hand, as shown in FIG. 24C, when a clot protrudes on a blood surface, only a very small number of pixels (several pixels when the image 100 has a size of 640×480 dots) in all the pixels included in the processing area 114 satisfy the above condition. When a size of an image is 640×480 dots, the above threshold is set to about 100 and thus blood coagulation can be detected with high accuracy.

When determining the presence or absence of blood coagulation, the CPU 71a associates a determination result with the measuring order having the specimen ID of the blood sample as a target of image processing and stores the result in the hard disk 71d (Step S1510), and then completes the process.

<Measuring Order Transmitting Operation of System Control Apparatus 7>

As described later, the sample transport apparatus 3 transmits a rack ID to the system control apparatus 7 to request a measuring order corresponding to the rack ID. The system control apparatus 7 transmits the measuring order to the sample transport apparatus 3 in accordance with the request.

Figure 25:
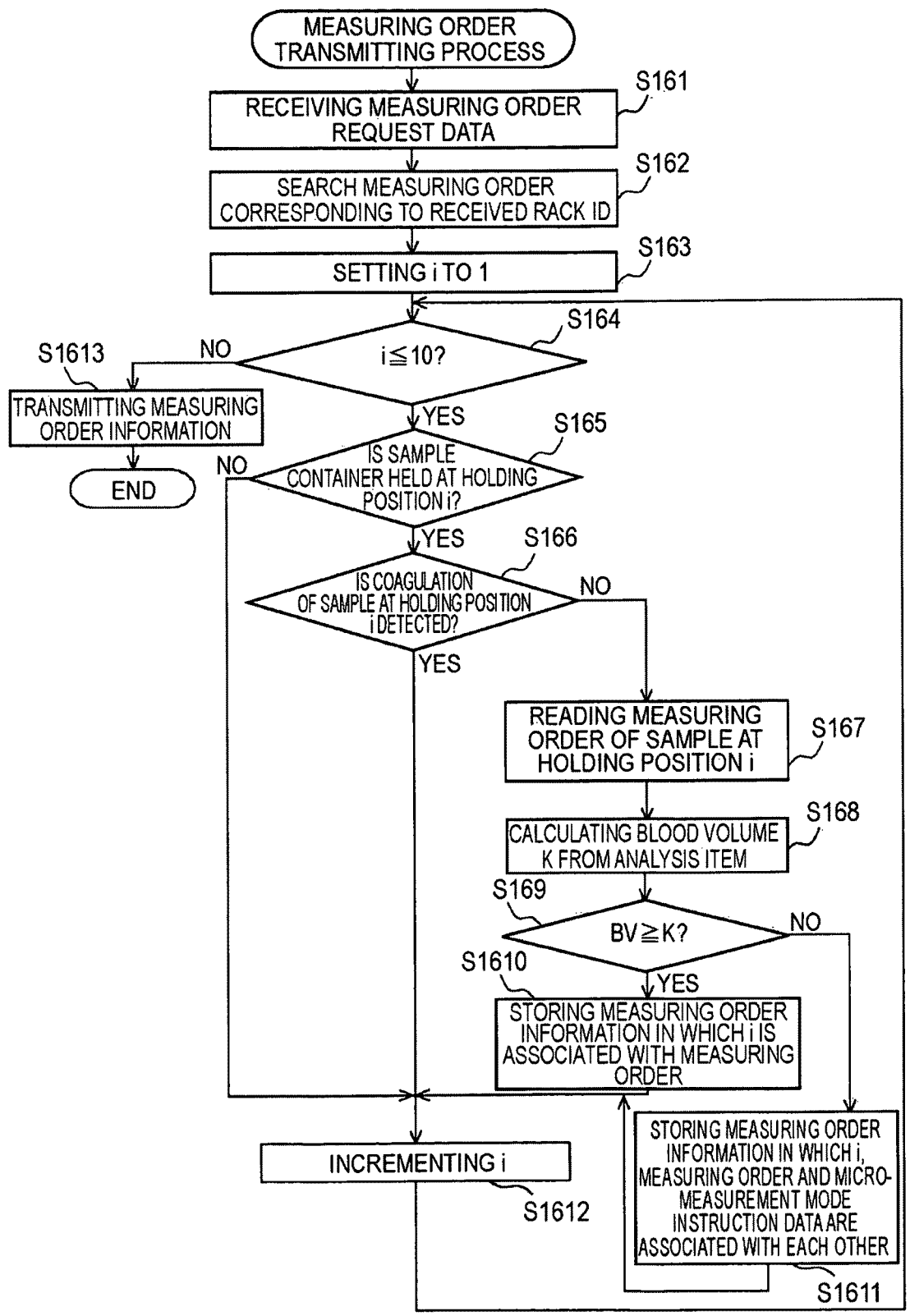
FIG. 25 is a flowchart showing the procedure of a measuring order transmitting process of the system control apparatus according to the first embodiment.

FIG. 25 is a flowchart showing the procedure of a measuring order transmitting process. As shown in FIG. 25, when request data of the measuring order including the rack ID transmitted from the sample transport apparatus 3 is received by the system control apparatus 7 (Step S161), an interrupt request is generated for the CPU 71a of the system control apparatus 7 and a process of Step S162 is invoked.

In Step S162, the CPU 71a searches the measuring order corresponding to the received rack ID from the hard disk 71d. Next, the CPU 71a sets a variable i indicating a holding position of the sample rack to 1 (Step S163) and determines whether i is equal to or less than 10 (Step S164). When i is equal to or less than 10 (Yes in Step S164), the CPU 71a determines whether the sample container is held at a holding position i (whether there is the measuring order corresponding to the holding position i) (Step S165). When the sample container is not held at the holding position i (No in Step S165), the CPU 71a performs a process of Step S1612.

When the sample container is held at the holding position i (Yes in Step S165), it is determined whether blood coagulation is detected in the sample at the holding position i (Step S166). When the blood coagulation is detected (Yes in Step S166), the CPU 71a performs a process of Step S1612.

On the other hand, when the blood coagulation is not detected in the sample at the holding position i (No in Step S166), the CPU 71a reads the measuring order of the blood sample at the holding position i from the hard disk 71d (Step S167). The CPU 71a determines a blood volume K necessary for analysis from an analysis item included in the measuring order (Step S168) and compares a blood volume BV detected in the blood sample at the holding position i with the necessary blood volume K to determine whether the expression $BV \geq K$ is satisfied (Step S169). When the expression $BV \geq K$ is satisfied (Yes in Step S169), the CPU 71a stores measuring order information in which the holding position i is associated with the measuring order in the RAM 71c (Step S1610) and performs a process of Step S1612.

On the other hand, when BV is less than K (No in Step S169), the CPU 71a stores measuring order information in which the holding position i, the measuring order and information instructing the micro-measurement mode are associated with each other in the RAM 71c (Step S1611) and performs a process of Step S1612. In Step S1612, the CPU 71a increments i by 1 and returns the process to Step S164. In Step S164, when i is not equal to or less than 10 (No in Step S164), the CPU 71a transmits the measuring order information stored in the RAM 71c to the sample transport apparatus 3 of a measuring order request source (Step S1613) and completes the process.

<Operation of Sample Transport Apparatus 3>

Figure 26:
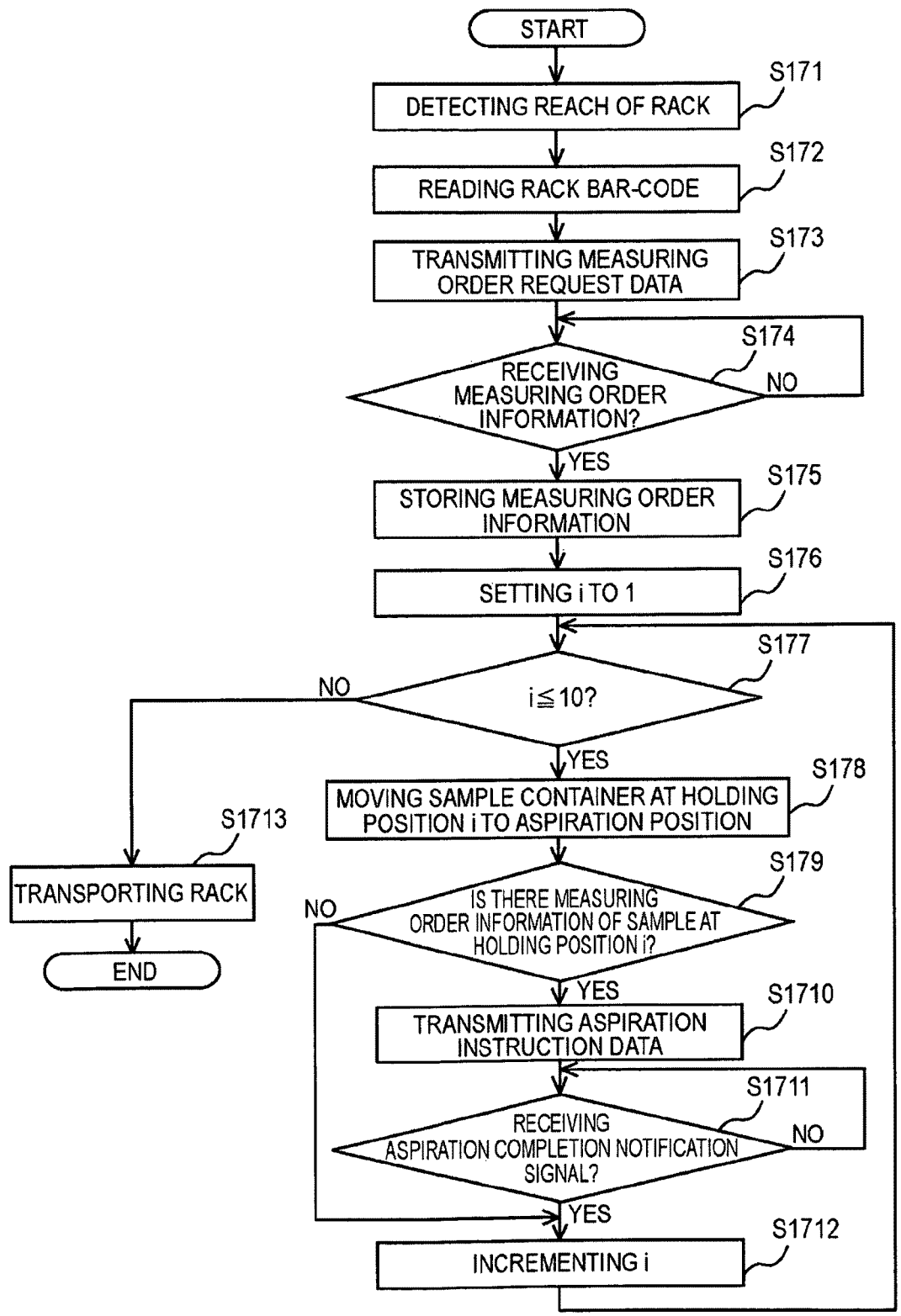
FIG. 26 is a flowchart showing the flow of an operation of a sample transport apparatus according to the first embodiment.

Herein, an operation of the sample transport apparatus 3 disposed in front of the blood cell analyzing apparatus 5 will be described. FIG. 26 is a flowchart showing the flow of the operation of the sample transport apparatus 3. When the sample rack 9 is transported to the rack slider 32 of the sample transport apparatus 3 from the upstream side of transportation, a sensor (not shown) detects the arrival of the sample rack 9. When a detection signal of the sample rack 9 is provided to the controller 31c from the sensor (Step S171), an interrupt request is generated for the CPU of the controller 31c and a process of Step S172 is invoked.

In Step S172, the controller 31c reads a rack bar-code of the sample rack 9 by a bar-code reader (not shown) to obtain a rack ID. The controller 31c transmits measuring order request data including the rack ID to the system control apparatus 7 (Step S173). Next, the controller 31c stands by to receive the measuring order information from the system control apparatus 7 (No in Step S174).

When the measuring order information is received by the sample transport apparatus 3 (Yes in Step S174), the controller 31c stores the received measuring order information in the memory of the sample transport apparatus 3 (Step S175). FIG. 27 is a schematic diagram showing the data structure of the measuring order information. The data stored in the memory of the sample transport apparatus 3 by the process of Step S175 is configured by a rack ID 160 and measuring order information 161a to 161j about the blood samples held in the sample rack 9. The measuring order information 161a to 161j includes holding position information, a measuring order and micro-measurement mode instruction data. The measuring order includes a specimen ID and analysis item data.

After storing the measuring order information in the memory, the controller 31c sets a variable i indicating the holding position of the sample rack to 1 (Step S176) and determines whether i is equal to or less than 10 (Step S177).

When i is equal to or less than 10 (Yes in Step S177), the controller 31c moves the sample container 8 at the holding position i to an aspiration position, where the blood cell analyzing apparatus 5 aspirates the sample, by the measuring line 31a (Step S178) and determines whether there is measuring order information about the sample at the holding position i in the measuring order information in the memory (Step S179). When there is not the measuring order information (No in Step S179), the controller 31c performs a process of Step S1712.

On the other hand, when there is the measuring order information about the sample at the holding position i (Yes in Step S179), the controller 31c transmits aspiration instruction data including the analysis item data and the specimen ID included in the measuring order information to the blood cell analyzing apparatus 5 (Step S1710). When micro-measurement mode instruction data is included in the measuring order information, the micro-measurement mode instruction data is included in the aspiration instruction data.

The controller 31c stands by to receive an aspiration completion notification signal from the blood cell analyzing apparatus 5 (No in Step S1711). When the aspiration completion notification signal is received from the blood cell analyzing apparatus 5 (Yes in Step S1711), the controller 31c performs a process of Step S1712.

In Step S1712, the controller 31c increments i by 1 and returns the process to Step S177. In Step S177, when i is not equal to or less than 10 (No in Step S177), the controller 31c conveys the sample rack 9 to the apparatus on the downstream side of transport (Step S1713) and completes the process.

As described above, regarding a blood sample, which is determined to have been coagulated and of which measuring order information is not generated, the sample container 8 containing the blood sample is stopped at an aspiration position, and then is transported from the aspiration position without the issue of aspiration instruction data. Regarding a blood sample, which is determined not to have been coagulated and of which measuring order information is generated, the sample container 8 is stopped at the aspiration position, and then aspiration instruction data is issued. This blood sample is aspirated by the measuring unit 51 as described later, and then is transported from the aspiration position after the aspiration completion notification signal is issued. Aspiration of the blood sample requires a predetermined time (for example, two seconds) and the predetermined time is longer than time (for example, one second) when the sample container of the blood sample which is determined to have been coagulated is stopped at the aspiration position. In this manner, by moving the blood sample, which is not required to be aspirated, from the aspiration position for a short time, a large number of blood samples cam be efficiently analyzed.

<Operation of Blood Cell Analyzing Apparatus 5>

Figure 28:
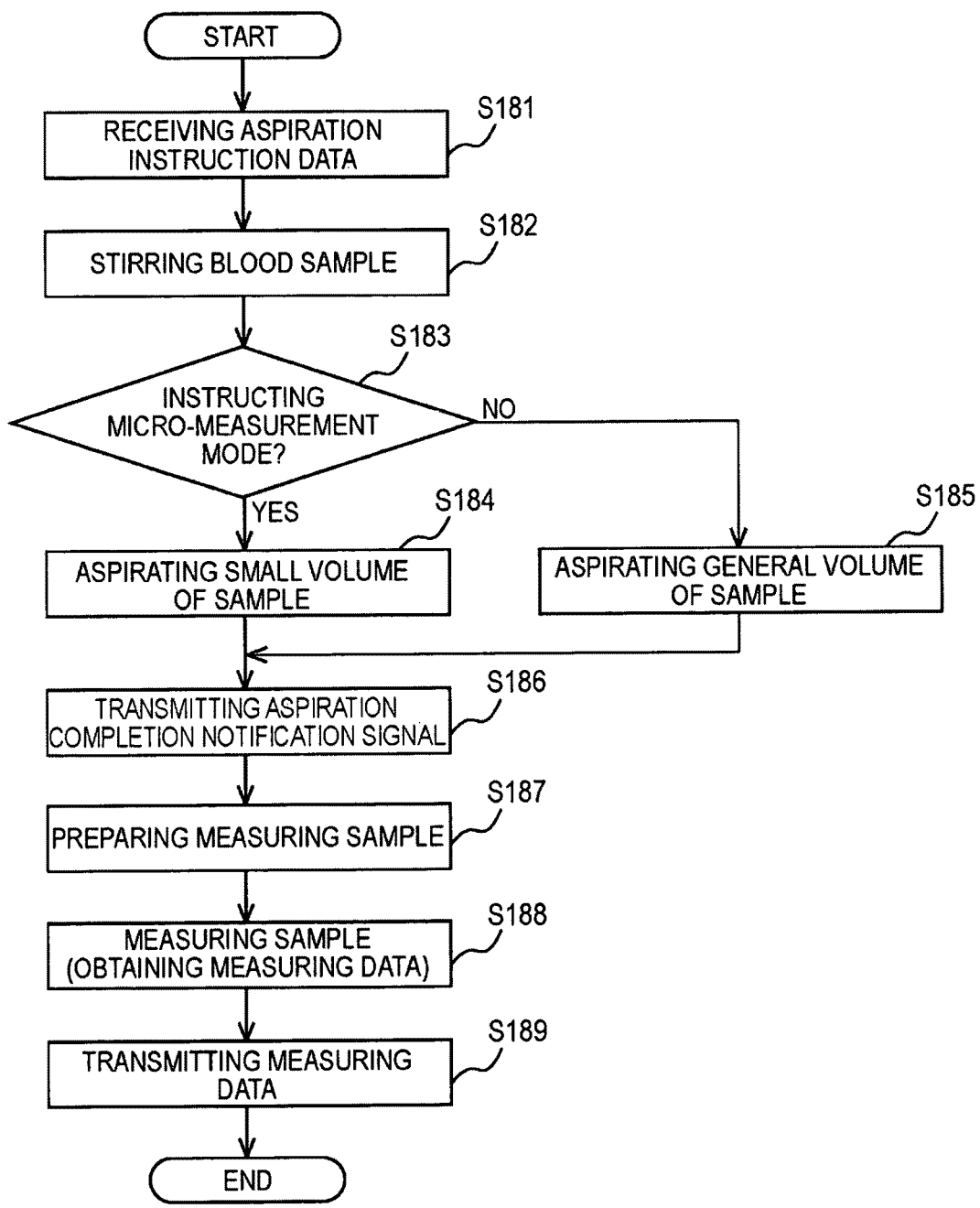
FIG. 28 is a flowchart showing the flow of an operation of the measuring unit of a blood cell analyzing apparatus according to the first embodiment.

Next, an operation of the blood cell analyzing apparatus 5 will be described. FIG. 28 is a flowchart showing the flow of an operation of the measuring unit 51 of the blood cell analyzing apparatus 5. When aspiration instruction data is received from the sample transport apparatus 3 to the measuring unit 51 (Step S181), an interrupt request is generated for the CPU of the controller 515 of the measuring unit 51 and a process of Step S182 is invoked.

In Step S182, the controller 515 stirs a blood sample in the sample container. Then, the controller 515 determines whether the aspiration instruction data includes micro-measurement mode instruction data (Step S183). When the micro-measurement mode instruction data is included (Yes in Step S183), the sample dispensing section 511 aspirates a smaller volume of the blood sample than in the normal-measurement mode (Step S184). When the micro-measurement mode instruction data is not included (No in Step S183), the controller 515 causes the sample dispensing section 511 to aspirate a general volume of the blood sample (Step S185). Next, the controller 515 transmits an aspiration completion notification signal to the sample transport apparatus 3 (Step S186).

Next, the controller 515 causes the measuring sample preparing section 512 to mix the aspirated blood sample, a reagent and a diluent and prepare a measuring sample (Step S187). After that, the controller 515 supplies the prepared measuring sample to the optical detecting section 513 to obtain measuring data including parameters such as peaks and pulse widths of a side-scattered light signal, a forward-scattered light signal and a fluorescent signal (Step S188). The controller 515 transmits the measuring data to the information processing unit 52 (Step S189) and completes the process.

The information processing unit 52 analyzes the received measuring data to classify blood cells included in the blood sample and count the number of blood cells for every type of blood cells. Furthermore, the information processing unit 52 creates a scattergram or a histogram and stores analysis result data including the specimen ID and these analysis results in the hard disk 521d. The image display section 522 displays an analysis result screen showing the analysis results.

<Operation of Sample Storing Apparatus 4>

The sample rack 9 delivered from the sample transport apparatus 3 on the downmost-stream side of transport is fed to the sample storing apparatus 4. The sample storing apparatus 4 transports the sample rack on the rack placing section and stores the sample rack.

(Second Embodiment)

[Configuration of Blood Sample Analyzing Apparatus]

Figure 29:
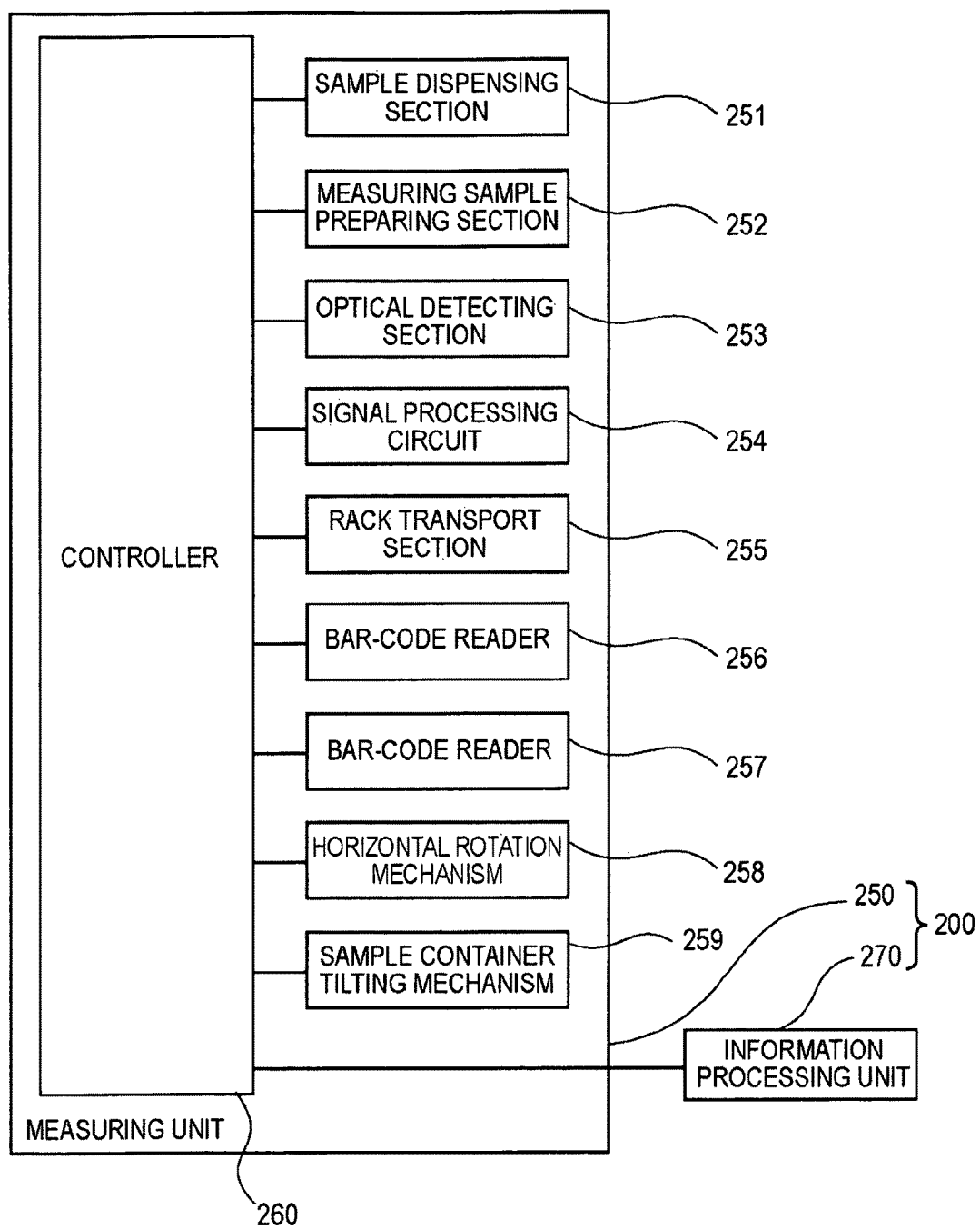
FIG. 29 is a block diagram showing the configuration of a blood sample analyzing apparatus according to a second embodiment.

FIG. 29 is a block diagram showing the configuration of a blood sample analyzing apparatus 200 according to this embodiment. The blood sample analyzing apparatus 200 as an optical flow cytometry type multiple blood cell analyzing apparatus obtains fluorescent intensity, side-scattered light intensity and the like of blood cells included in a blood sample, classifies the blood cells included in the sample on the basis of the above fluorescent intensity, side-scattered light intensity and the like, and counts the number of blood cells for every type. Moreover, the blood sample analyzing apparatus 200 creates a scattergram in which the classified blood cells are color-coded for every type, and displays the scattergram. The blood sample analyzing apparatus 200 includes a measuring unit 250 for measuring a blood sample and an information processing unit 270 for processing measuring data output from the measuring unit 250 and displaying an analysis result of the blood sample.

As shown in FIG. 29, the measuring unit 250 includes a sample dispensing section 251, a measuring sample preparing section 252, an optical detecting section 253, a signal processing circuit 254, a rack transport section 255, bar-code readers 256 and 257, a horizontal rotation mechanism 258, a sample container tilting mechanism 259 and a controller 260. The rack transport section 255 can transport the sample rack 9 and is configured to transport the sample container 8 held in the sample rack 9 to an aspiration position for aspirating the sample in the sample container 8 by the sample dispensing section 251 and to move the sample container 8 in which aspiration is completed from the aspiration position.

The rack transport section 255 is provided with a before-analysis placing table for placing the sample rack 9 storing the sample container 8 before analysis, an after-analysis placing table for storing the sample rack 9 storing the sample container 8 after analysis, and a transport path for the sample rack 9 from the before-analysis placing table to the after-analysis placing table through the aspiration position (not shown). In the transport path, the horizontal rotation mechanism 258 and the sample container tilting mechanism 259 are provided and the bar-code reader 256 for reading a rack bar-code of the sample rack 9 on the transport path and the bar-code reader 257 for reading a specimen bar-code of the sample container 8 are provided.

Two cameras and two white LEDs are disposed in front of the sample container tilting mechanism 259. One of the cameras images the sample container 8 which is taken out from the sample rack 9 and held in a vertical state by the sample container tilting mechanism 259, and the other camera images the sample container 8 which is vertically rotated and held in a state in which a bottom portion of the sample container 8 is positioned higher than a lid 8a by the sample container tilting mechanism 259. These cameras are connected to the information processing unit 270 by a cable for transmitting electric signals of captured images. Since the configurations and arrangement of the horizontal rotation mechanism 258, the sample container tilting mechanism 259, the cameras and the white LEDs are the same as in the first embodiment, a description thereof will be omitted.

Since the other configurations of the blood sample analyzing apparatus 200 are the same as the configurations of the blood cell analyzing apparatus 5 described in the first embodiment, a description thereof will be omitted.

<Operation of Blood Sample Analyzing Apparatus>

Figure 30A:
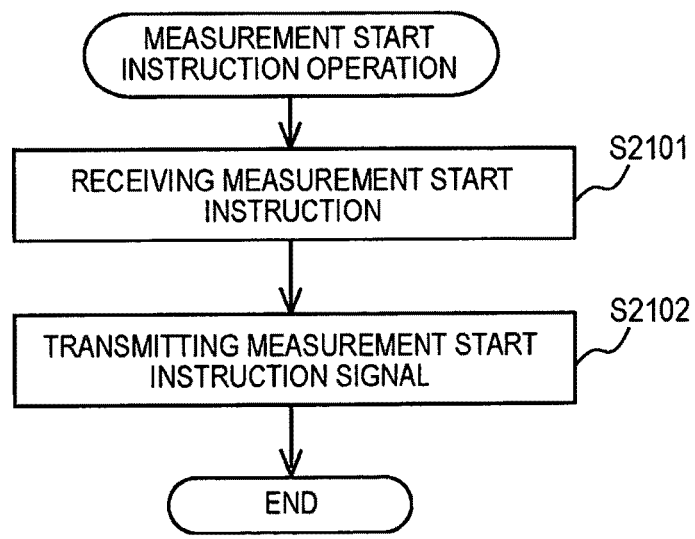
FIG. 30A is a flowchart showing the flow of a measurement start instruction operation of an information processing unit according to the second embodiment.
Figure 30C:
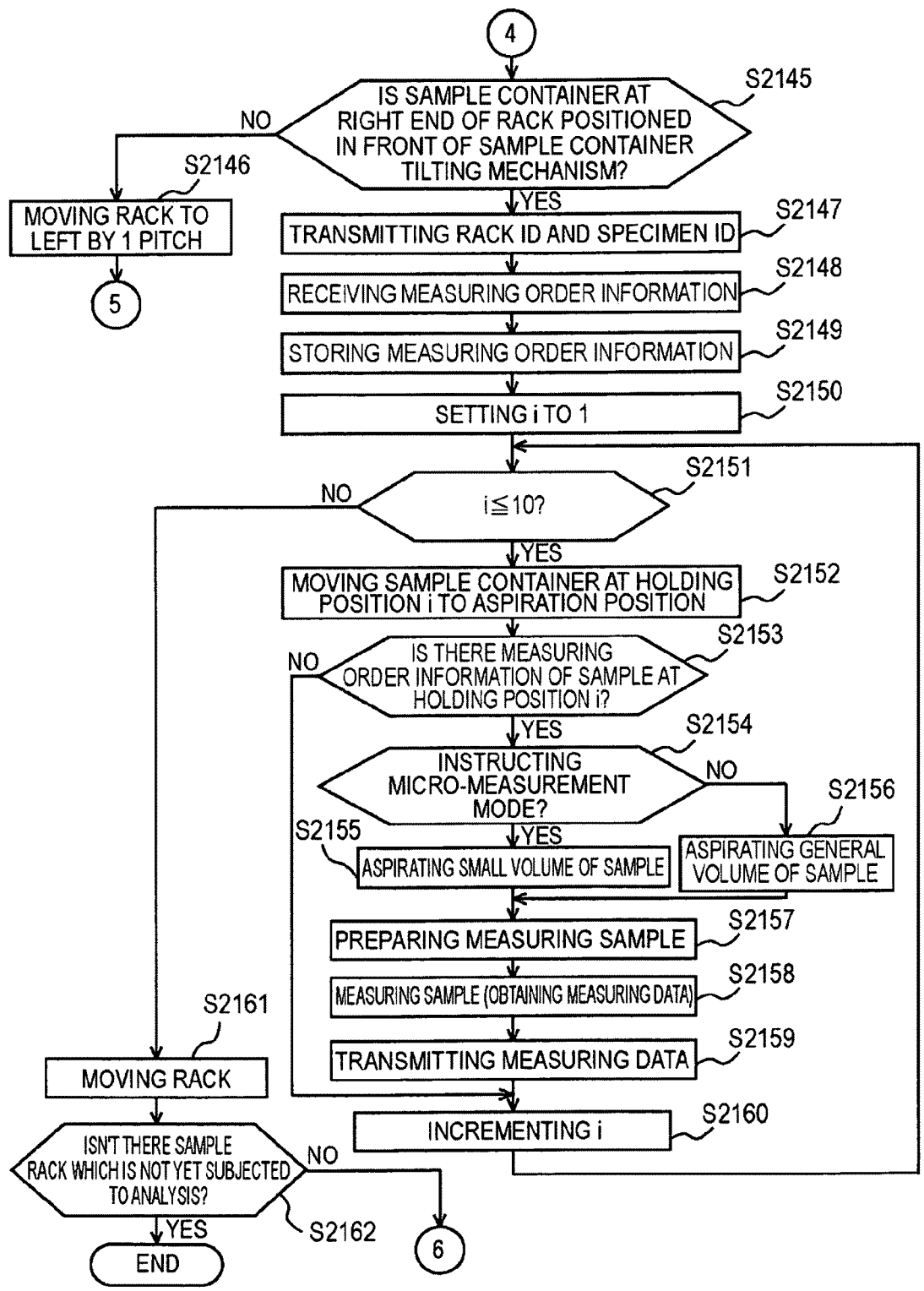
FIG. 30C is a flowchart (second half) showing the flow of the sample measuring operation of the measuring unit according to the second embodiment.

Next, an operation of the blood sample analyzing apparatus according to this embodiment will be described. FIGS. 30A to 30C are flowcharts showing the flow of an operation of the blood sample analyzing apparatus 200 according to this embodiment. FIG. 30A is a flowchart showing the flow of a measurement start instruction operation of the information processing unit 270, and FIGS. 30B and 30C are flowcharts showing the flow of a sample measuring operation of the measuring unit 250 in the sample analysis operation of the blood sample analyzing apparatus 200.

First, when a user starts the blood sample analyzing apparatus 200, an initialization process is executed in the measuring unit 250 and the information processing unit 270, and thus the measuring unit 250 is in a measurement stand-by state and the information processing unit 270 displays a main screen (not shown). Measuring order including a specimen (sample) number, patient information such as a name, age, sex and department of a patient associated with the specimen number and information such as an analysis item is input to the information processing unit 270 in advance by manual input of the user, and the measuring order is stored in a hard disk. In this state, when a start button displayed in the main screen is clicked, that is, when the user performs a start instruction operation, a CPU of the information processing unit 270 receives an instruction for measurement start (Step S201 of FIG. 30A), and when such an event is generated, a process of Step S2102 is invoked.

In Step S2102, the CPU of the information processing unit 270 generates a measurement start instruction signal and the signal is transmitted to the measuring unit 250 (Step S2102 of FIG. 30A). Then, the CPU completes the process related to the measurement start instruction operation. By issuing the measurement start instruction, the measuring operation of the measuring unit 250 shown in FIG. 30B is started. When the measurement start instruction signal is received by the measuring unit 250 (Step S2131 of FIG. 30B), the controller 260 of the measuring unit 250 controls the rack transport section 255 (Step S2132). Processes of Steps S2132 to S2147 are the same as the processes of Steps S103 to S118 described in the first embodiment, except that a transmission destination of information is the information processing unit 270 in Steps S2141, S2143 and S2147, and thus a description thereof will be omitted.

When receiving a first image taking instruction signal, the information processing unit 270 performs a blood volume detecting process, and when receiving a second image taking instruction signal, the information processing unit performs a blood coagulation determining process. Since the blood volume detecting process and the blood coagulation determining process are the same as in the first embodiment, a description thereof will be omitted. In addition, the information processing unit 270 searches measuring orders corresponding to a rack ID and a specimen ID, determines that a sample in which blood coagulation is detected by the blood coagulation determining process is not measured for each measuring order, and determines whether a sample, in which blood coagulation is not detected, is measured in the normal-measurement mode or in the micro-measurement mode by the measuring order and the blood volume detected by the blood volume detecting process. The processes are the same in Steps S162 to S1613 described in the first embodiment, except that a transmission destination of measuring order information is the measuring unit 250, and thus a description thereof will be omitted.

When an event in which measuring order information is received from the information processing unit 270 occurs (Step S2148), the controller 260 stores the received measuring order information in a memory of the controller 260 (Step S2149). Then, the controller 260 sets a variable i indicating a holding position of the sample rack to 1 (Step S2150) and determines whether i is equal to or less than 10 (Step S2151). When i is equal to or less than 10 (Yes in Step S2151), the controller 260 moves the sample container 8 at the holding position i to an aspiration position where the sample dispensing section 251 aspirates the sample (Step S2152), and determines whether there is a measuring order of the sample at the holding position i from the measuring order information in the memory (Step S2153). When there is not the measuring order (No in Step S2153), the controller 260 performs a process of Step S2160.

On the other hand, when there is the measuring order of the sample at the holding position i (Yes in Step S2153), the controller 260 determines whether micro-measurement mode instruction data is included in the measuring order information (Step S2154). When the micro-measurement mode instruction data is included (Yes in Step S2154), the controller causes the sample dispensing section 251 to aspirate a smaller volume of the blood sample than in the normal-measurement mode (Step S2155). When the micro-measurement mode instruction data is not included (No in Step S2154), the controller 260 causes the sample dispensing section 251 to aspirate a general volume of the blood sample (Step S2156).

Next, the controller 260 causes the measuring sample preparing section 252 to mix the aspirated blood sample, a reagent and a diluent and prepare a measuring sample (Step S2157). The controller supplies the prepared measuring sample to the optical detecting section 253 to obtain measuring data including parameters such as peaks and pulse widths of a side-scattered light signal, a forward-scattered light signal and a fluorescent signal (Step S2158). The controller 260 transmits the measuring data to the information processing unit 270 (Step S2159), increments i by 1 (Step S2160) and returns the process to Step S2151. In Step S2151, when i is not equal to or less than 10 (No in Step S2151), the controller 260 moves the sample rack 9 to a storage position on the downstream side of transport (Step S2161). Next, when the sample rack to be analyzed is placed on the before-analysis placing table of the rack transport section 255 (No in Step S2162), the controller 260 returns the process to Step S2132, and when the sample rack to be analyzed is not placed on the before-analysis placing table of the rack transport section 255 (Yes in Step S2162), the controller completes the process.

(Third Embodiment)

This embodiment is a blood sample analyzing system which transports a sample rack holding a sample container in which a blood sample is determined to have been coagulated by a skip line not supplying the sample rack to a blood cell analyzing apparatus.

[Configuration of Blood Sample Analyzing System]

The configuration of the blood sample analyzing system according to this embodiment is the same as the configuration of the blood sample analyzing apparatus 1 according to the first embodiment, except for a sample transport apparatus 330 (see FIG. 1 for reference). Accordingly, the same constituent elements are denoted by the same reference numerals and a description thereof will be omitted. The sample transport apparatus 330 according to this embodiment has the same configuration as the configuration of the sample transport apparatus 3 according to the first embodiment, except that a controller 331c of a conveyor 331 (see FIG. 9 for reference) is configured to perform the following operation. Accordingly, the same constituent elements are denoted by the same reference numerals and a description thereof will be omitted.

[Operation of Blood Sample Analyzing System]

The blood sample analyzing system according to this embodiment performs the same operation as the operation of the sample analyzing system 1 described in the first embodiment, except for the operation of the sample transport apparatus 3. A description of the same operation as the operation of the sample analyzing system 1 according to the first embodiment will be omitted.

<Operation of Sample Transport Apparatus 330>

Figure 31A:
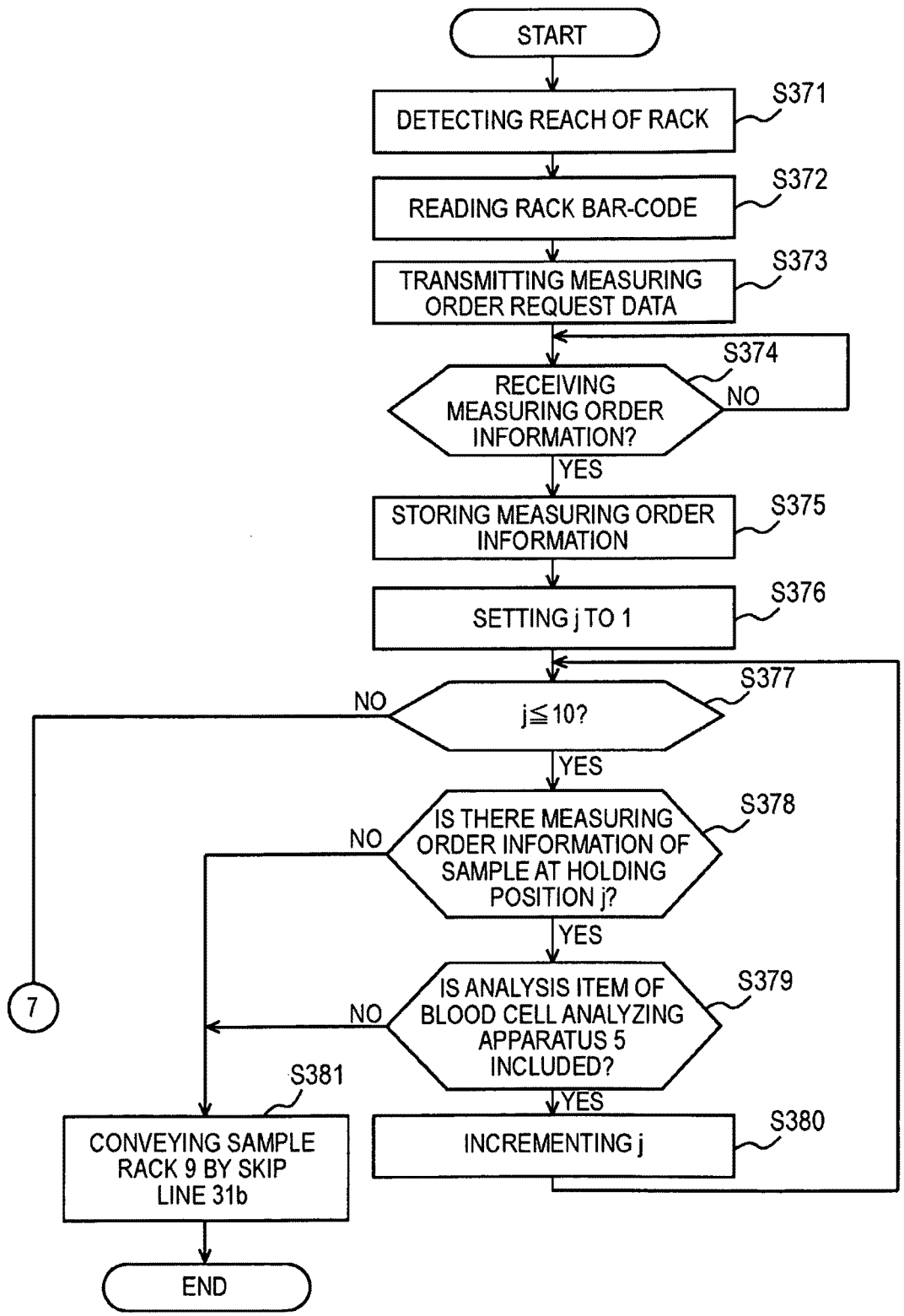
FIG. 31A is a flowchart (first half) showing the flow of an operation of a sample transport apparatus according to a third embodiment.
Figure 31B:
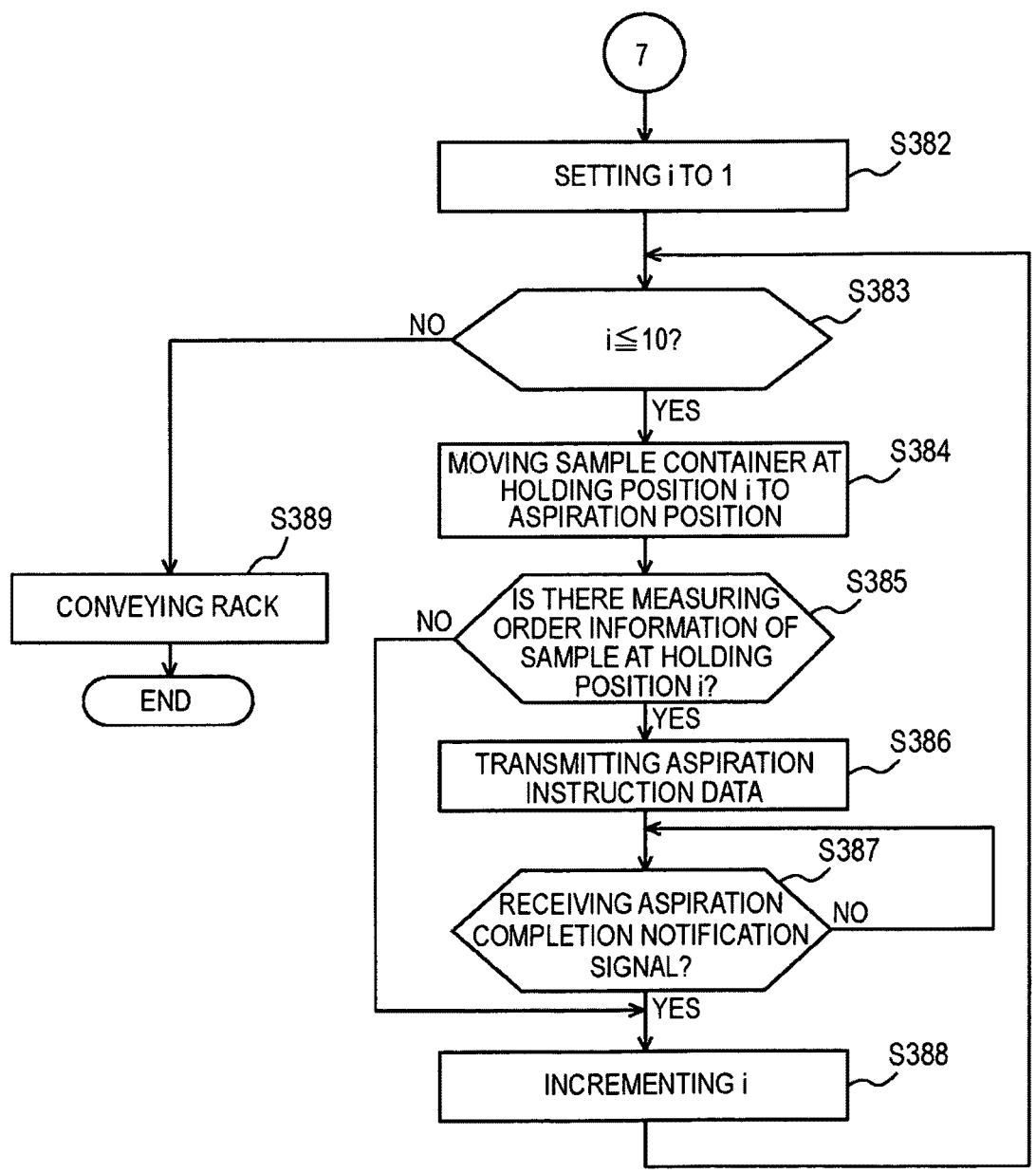
FIG. 31B is a flowchart (second half) showing the flow of the operation of the sample transport apparatus according to the third embodiment.

Herein, an operation of the sample transport apparatus 330 disposed in front of the blood cell analyzing apparatus 5 will be described. FIGS. 31A and 31B are flowchart showing the flow of the operation of the sample transport apparatus 330. Since processes of Steps S371 to S375 are the same as the processes of Steps S171 to S175 described in the first embodiment, a description thereof will be omitted.

After storing measuring order information in a memory, the controller 331c sets a variable j indicating a holding position of the sample rack to 1 (Step S376) and determines whether j is equal to or less than 10 (Step S377). When j is equal to or less than 10 (Yes in Step S377), the controller 331c determines whether there is measuring order information about a sample at the holding position j in the measuring order information in the memory (Step S378). When there is not the measuring order information (No in Step S378), the controller 331c performs a process of Step S381.

In Step S378, when there is the measuring order information about the sample at the holding position j (Yes in Step S378), the controller 331c determines whether there is an analysis item of the blood cell analyzing apparatus 5 in analysis items included in the measuring order (Step S379). The process of Step S379 in the sample transport apparatus 330 disposed in front of the smear preparing apparatus 6 is a process of determining whether preparing a smear is included in the analysis items of the measuring order.

When there is not the analysis item of the blood cell analyzing apparatus 5 in the analysis items included in the measuring order (No in Step S379), the controller 331c performs a process of Step S381. On the other hand, when there is the analysis item of the blood cell analyzing apparatus 5 in the analysis items included in the measuring order of the sample at the holding position j, the controller 331c increments j by 1 (Step S380) and returns the process to Step S377.

When there is not the measuring order information about the sample at the holding position j in Step S378, or when there is not the analysis item of the blood cell analyzing apparatus 5 in the analysis items included in the measuring order of the sample at the holding position j in Step S379, the controller 331c controls the rack slider 32 to put the sample rack 9 into the skip line 31b and convey the sample rack 9 to the apparatus on the downstream side (Step S381), and completes the process.

In Step S377, when j is not equal to or less than 10 (No in Step S377), the controller 331c performs a process of Step S382. Since processes of Steps S382 to S389 are the same as the processes of Steps S176 to S1713 described in the first embodiment, a description thereof will be omitted.

By controlling the operation of the sample transport apparatus 330 as described above, the sample rack 9 in which all the blood samples in the held sample containers are not coagulated is put into the measuring line 31a to be supplied to the blood cell analyzing apparatus 5 (smear preparing apparatus 6). On the other hand, the sample rack 9 which holds even one sample container 8 containing a coagulated blood sample is transported by the skip line 31b to be stored in the sample storing apparatus 4. An user can performs a proper operation, such as an operation of taking out the sample container 8 in which the blood sample is coagulated from the sample rack 9 stored in the sample storing apparatus 4, setting the sample rack 9 in the sample putting apparatus 2 again and analyzing the coagulated blood sample by a manual method.

(Fourth Embodiment)

This embodiment is a blood sample analyzing system which stores a sample rack holding a sample container in which a blood sample is determined to have been coagulated in a sample check unit, without supplying the sample rack to a blood cell analyzing apparatus.

[Configuration of Blood Sample Analyzing System]

The configuration of the blood sample analyzing system according to this embodiment is the same as the configuration of the blood sample analyzing apparatus 1 according to the first embodiment, except for a sample putting apparatus 420 and a system control apparatus 470 (see FIG. 1 for reference). Accordingly, the same constituent elements are denoted by the same reference numerals and a description thereof will be omitted. The sample putting apparatus 420 according to this embodiment has the same configuration as the configuration of the sample putting apparatus 2 according to the first embodiment, except that a controller 422 (see FIG. 5 for reference) of a sample check unit 421 is configured to perform the following operation. In addition, the system control apparatus 470 according to this embodiment has the same configuration of the system control apparatus 7 according to the first embodiment, except that the CPU 71a is configured to perform the following process by a system control program 474a (see FIG. 12 for reference) stored in the hard disk 71d. Accordingly, the same constituent elements are denoted by the same reference numerals and a description thereof will be omitted.

[Operation of Blood Sample Analyzing System]

The blood sample analyzing system according to this embodiment performs the same operation as the operation of the sample analyzing system 1 described in the first embodiment, except for the operations of the sample putting apparatus 420 and the system control apparatus 470. A description of the same operation as the operation of the sample analyzing system 1 according to the first embodiment will be omitted.

<Operation of Sample Putting Apparatus 420>

Figure 32A:
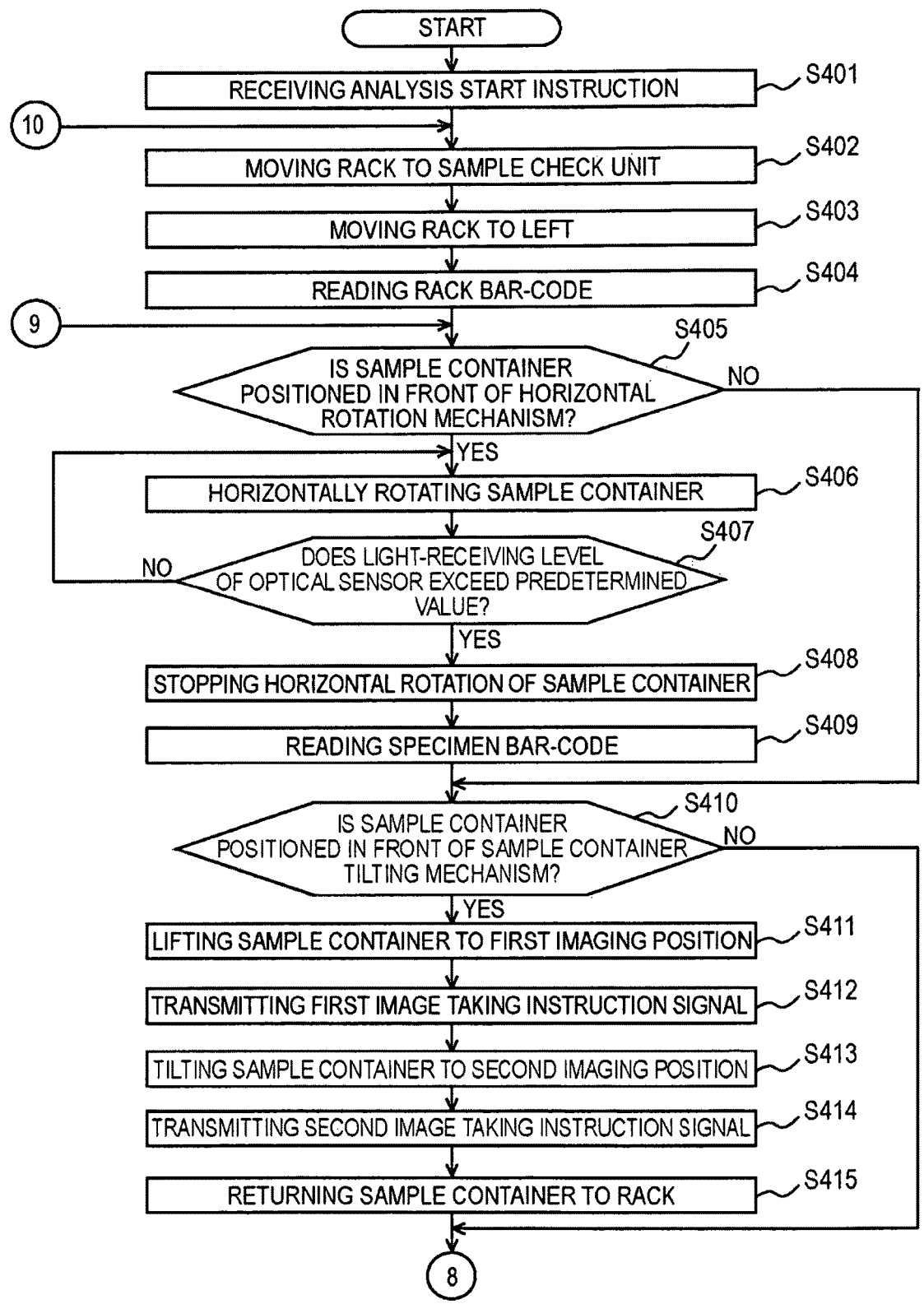
FIG. 32A is a flowchart (first half) showing the flow of an operation of a sample putting apparatus according to a fourth embodiment.
Figure 32B:
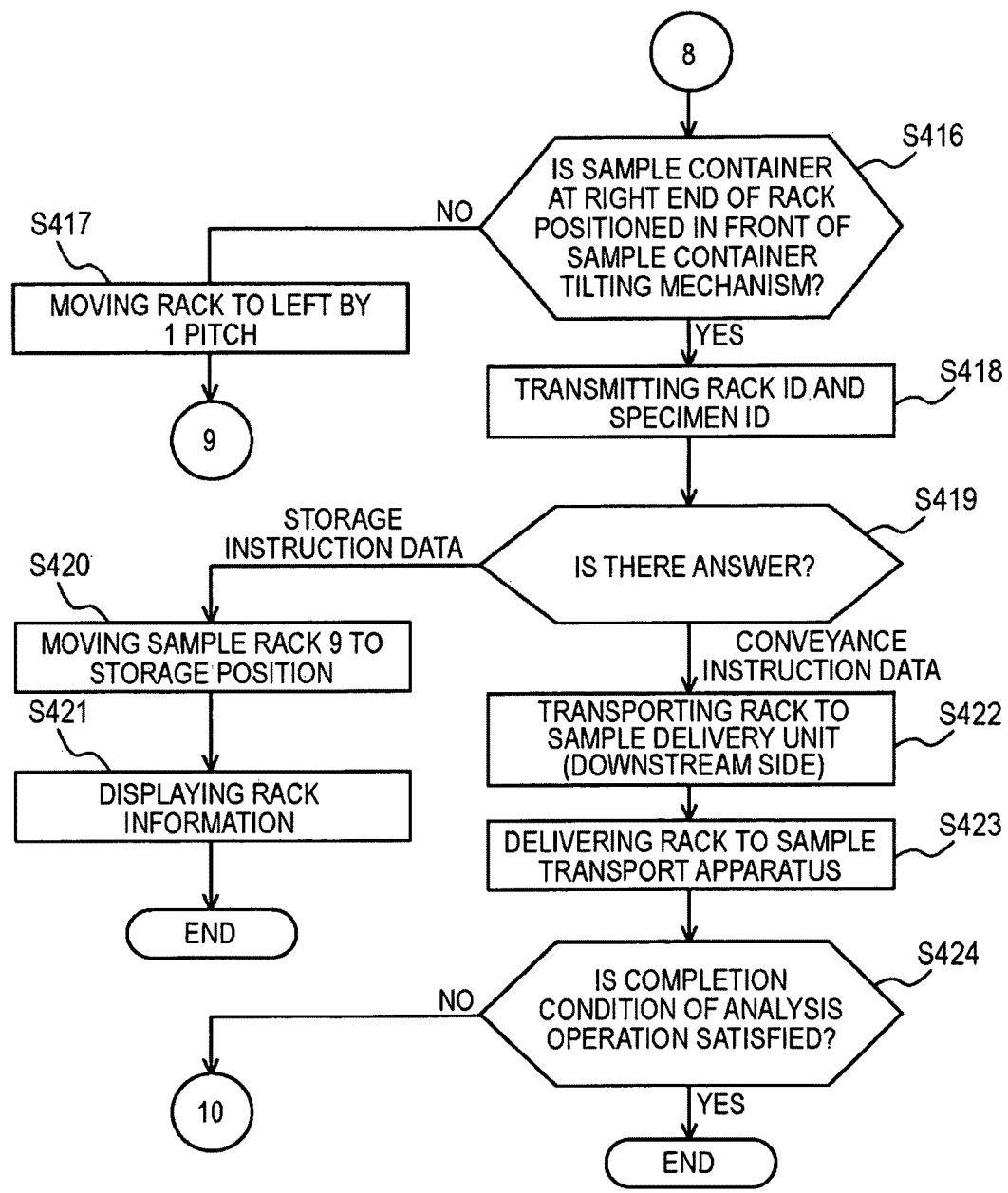
FIG. 32B is a flowchart (second half) showing the flow of the operation of the sample putting apparatus according to the fourth embodiment.

FIGS. 32A and 32B are flowcharts showing the flow of the operation of the sample putting apparatus according to this embodiment. Since processes of Steps S410 to S418 are the same as the processes of Steps S101 to S118 described in the first embodiment, a description thereof will be omitted.

The controller 422 transmits a rack ID of the sample rack 9 on a transport path of the sample check unit 421 and specimen IDs of all the sample containers 8 stored in the sample rack 9 to the system control apparatus 470, and then receives an answer from the system control apparatus 470 (Step S419). The controller 422 stands by until there is the answer from the system control apparatus 470 (No is Step S419). In Step S419, when the sample check unit 421 receives storage instruction data for instructing the storage of the sample rack 9 from the system control apparatus 470 ("storage instruction data" in Step S419), the controller 422 transports the sample rack 9 to the front side of the rack placing section 221 and places the sample rack 9 in the rack placing section 221 (Step S420). The storage instruction data includes the rack ID of the sample rack 9. In addition, it includes coagulation abnormality data indicating blood coagulation when there is a blood sample which is determined to have been coagulated, and includes specimen bar-code reading error data when an error occurs in reading a specimen bar-code. The coagulation abnormality data and the specimen bar-code reading error data corresponds to a holding position of the blood sample which is determined to have been coagulated and a holding position where the error in reading a specimen bar-code occurs, respectively.

Figure 33:
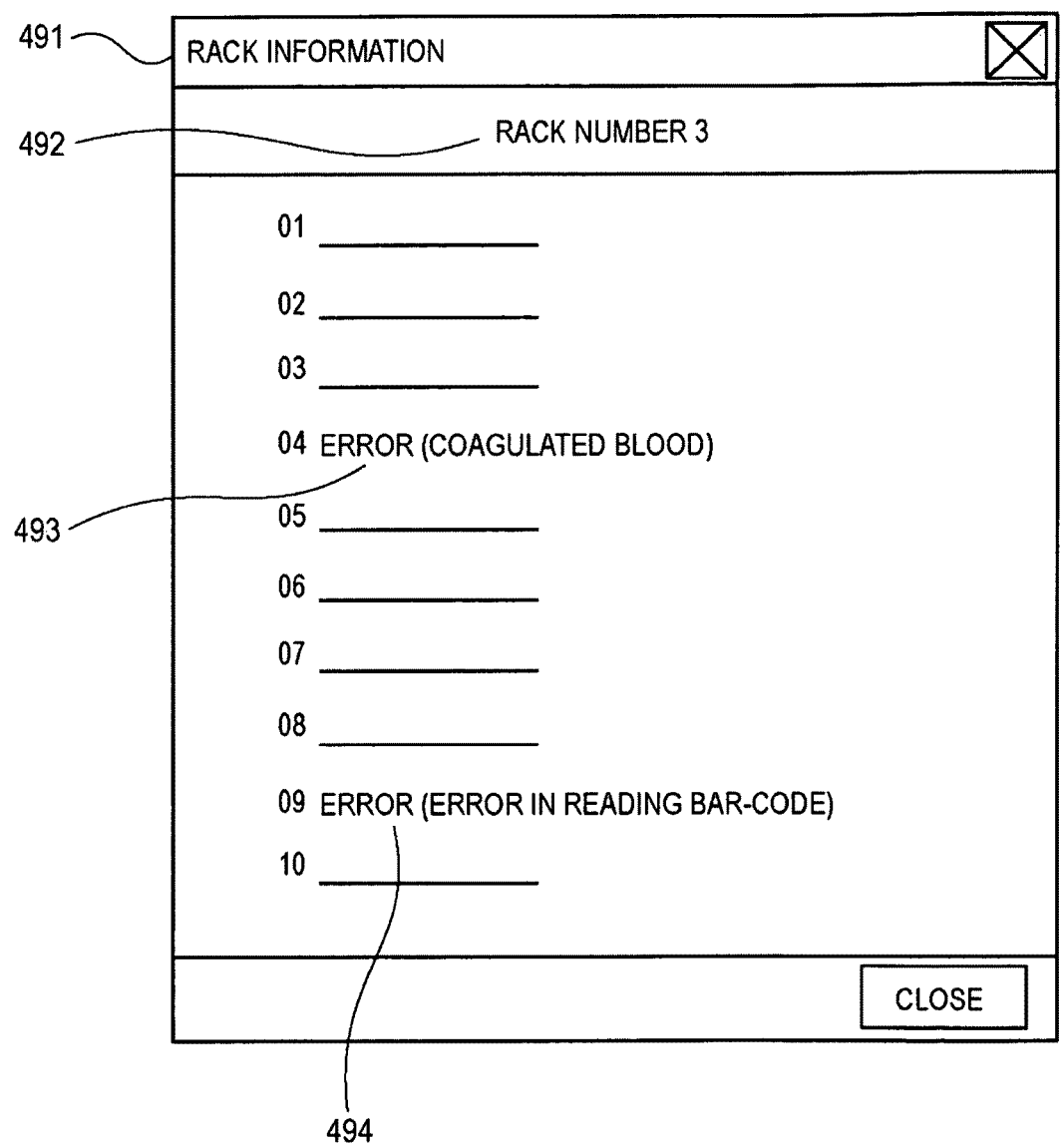
FIG. 33 is a diagram showing an example of a rack information display screen of a liquid crystal display section of the sample putting apparatus according to the fourth embodiment.

When receiving the storage instruction data, the controller 422 causes the liquid crystal display section 227 to display rack information (Step S421). FIG. 33 is a diagram showing an example of a rack information display screen of the liquid crystal display section 227. As shown in FIG. 33, a rack number (rack ID) 492, holding position numbers of sample racks, and error information 493 and 494 corresponding to the holding positions are included in a rack information display screen 491. The error information 493 indicates blood coagulation and the error information 494 indicates an error in reading a bar-code. An user confirms the screen to perform a proper operation, such as an operation of taking out the sample container 8 in which blood is coagulated from the sample rack 9 to analyze the blood sample by a manual method and taking out the sample container 8 in which an error occurs in reading a bar-code to read the specimen bar-code by the handy bar-code reader 222c again. Then, the controller 422 completes the process.

In Step S419, when the sample check unit 421 receives conveyance instruction data for instructing conveyance of the sample rack 9 from the system control apparatus 470 ("conveyance instruction data" in Step S419), the controller 422 performs a process of Step S422. Since processes of Steps S422 to S424 are the same as the processes of Steps S119 to S121 described in the first embodiment, a description thereof will be omitted.

<Operation of System Control Apparatus 470>

The system control apparatus 470 according to this embodiment can perform the following measuring order obtaining operation.

Figure 34:
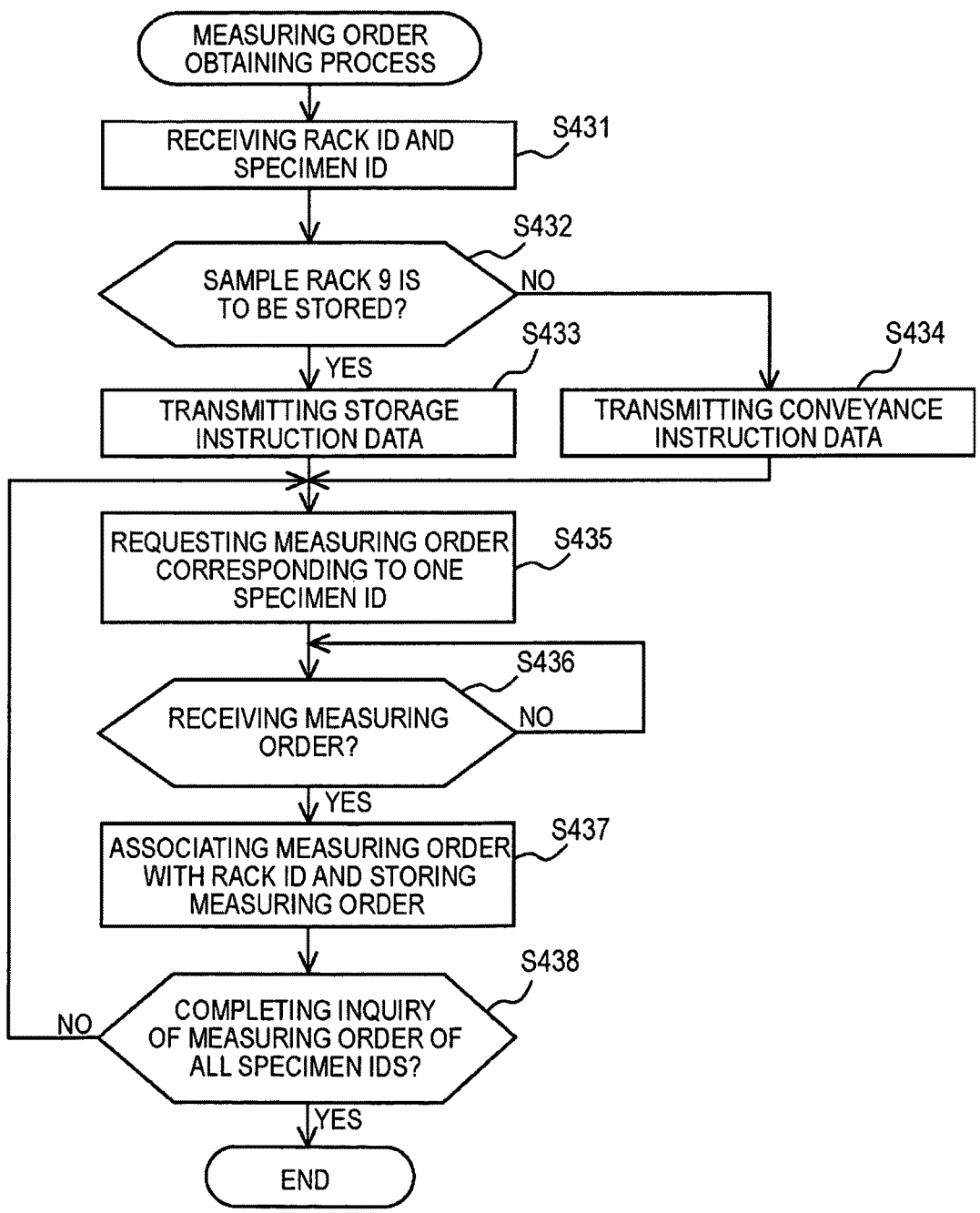
FIG. 34 is a flowchart showing the procedure of a measuring order obtaining process of a system control apparatus according to the fourth embodiment.

FIG. 34 is a flowchart showing the procedure of a measuring order obtaining process of the system control apparatus 470. As shown in FIG. 34, when an event in which a rack ID and a specimen ID transmitted from the sample putting apparatus 420 are received by the system control apparatus 470 (Step S431), a process of Step S432 is invoked in the CPU 71a of the system control apparatus 470.

In Step S432, the CPU 71a determines whether the sample rack 9 is to be stored. This process will be described in detail. First, the CPU 71a determines whether a blood sample which is determined to have been coagulated is included in blood samples each positioned at a holding position. Furthermore, the CPU 71a determines whether data indicating an error in reading a specimen bar-code is included in the data received in the above Step S431. Due to these processes, when a blood sample which is determined to have been coagulated is included, when the data indicating the error in reading a specimen bar-code is included, or when both of them are included, it is determined that the sample rack 9 is to be stored. On the other hand, when the sample rack 9 does not store the sample container 8 in which blood is coagulated and no error occurs in reading a specimen bar-code, it is determined that the sample rack 9 is not to be stored.

In Step S432, when it is determined that the sample rack 9 is to be stored (Yes in Step S432), the CPU 71a generates storage instruction data as described above and transmits the data to the sample putting apparatus 420 (Step S433). On the other hand, in Step S432, when it is determined that the sample rack 9 is not to be stored (No in Step S432), the CPU 71a generates conveyance instruction data and transmits the data to the sample putting apparatus 420 (Step S434). After transmitting one of the data, the CPU 71a performs a process of Step S435. Since processes of Steps S435 to S438 are the same as the processes of Steps S132 to S135 described in the first embodiment, a description thereof will be omitted.

(Other Embodiments)

In the above-described first and second embodiments, the configuration, in which the sample container 8 for a blood sample which is determined to have been coagulated is stopped at an aspiration position and transported from the aspiration position without being subjected to aspiration, has been described. However, the invention is not limited to this. A configuration, in which the sample container for a blood sample which is determined to have been coagulated is transported to an aspiration position and passes the aspiration position without being stopped, may be also employed. In this manner, by not stopping the sample container 8 for a coagulated blood sample at an aspiration position, a number of blood samples can be more efficiently analyzed.

In the above-described second embodiment, the blood sample analyzing apparatus, in which the sample container 8 for a blood sample which is determined to have been coagulated is stopped at an aspiration position for a shorter time than the sample container 8 for a blood sample which is determined not to have been coagulated, and transported from the aspiration position without being subjected to aspiration, has been described. However, the invention is not limited to this. For example, a blood sample analyzing apparatus, in which the sample rack 9 holding a sample container for a blood sample which is determined to have been coagulated is transported by a skip line, or a blood sample analyzing apparatus, in which the sample rack 9 holding a sample container for a blood sample which is determined to have been coagulated is transported to a storage position different from the aspiration position, may be also employed.

In the above-described third embodiment, the configuration, in which the sample rack 9 is transported by the skip line 31b and stored in the sample storing apparatus 4 when the sample rack 9 holds even one sample container 8 containing a coagulated blood sample, has been transported. However, the invention is not limited to this. A configuration, determination whether a blood sample in a held sample container is coagulated, whether the sample container is held at a holding position, and whether an analysis item of the blood cell analyzing apparatus 5 is included in a measuring order is performed at every holding position in the sample rack 9, and when even one sample container for a blood sample (that is, the blood sample is not coagulated and the measuring order includes the analysis item of the blood cell analyzing apparatus 5) which can be analyzed by the blood cell analyzing apparatus 5 is included in all the held sample containers, the sample rack 9 is transported by the measuring line 31a to supply the blood sample to the blood cell analyzing apparatus 5, may be also employed. In this case, a configuration, in which when the blood samples (that is, the blood samples are coagulated or the measuring order does not include the analysis item of the blood cell analyzing apparatus 5) in all the held sample containers cannot be analyzed by the blood cell analyzing apparatus 5, or when no sample container is held, the sample rack 9 is transported by the skip line 31b and stored in the sample storing apparatus 4, may be also employed. As being configured as described above, the sample rack 9 holding even one sample container 8 for a blood sample which can be analyzed by the blood cell analyzing apparatus 5 is supplied to the blood cell analyzing apparatus 5 to perform analysis, and thus a number of blood samples can be efficiently analyzed.

In the above-described first to fourth embodiments, the configuration, in which an image obtained by imaging the tilted sample container is processed, a position of an image of a blood surface in the image is detected, the processing area 114 is set to be higher than the position of the image of the blood surface and the processing area is processed to determine blood coagulation, has been described. However, the invention characterized in that the aspiration section or the transport section is controlled based on the result of the determination whether the blood is coagulated is not limited to this. A configuration, in which an image obtained by imaging the sample container 8 in a vertical state and an image obtained by imaging the sample container 8 in a tilted state are binarized to obtain area ratios of blood portions specified by the binarized images and a difference between the areas is compared with a predetermined reference value to perform determination of blood coagulation, may be also employed.

In the above-described first, third and fourth embodiments, the system control apparatuses 7 and 470 generate measuring order information of a blood sample which is determined not to have been coagulated and does not generate measuring order information of a blood sample which is determined to have been coagulated and the measuring order information is transmitted to the sample transport apparatuses 3 and 330. In addition, the sample transport apparatuses 3 and 330 are configured to transmit aspiration instruction data to the blood cell analyzing apparatus 5 or the smear preparing apparatus 6 in the case of the blood sample for which the measuring order information exists, and not to transmit the aspiration instruction data to the blood cell analyzing apparatus 5 or the smear preparing apparatus 6 in the case of the blood sample for which measuring order information does not exist. Accordingly, the sample dispensing section 511 is controlled to aspirate the blood sample which is determined not to have been coagulated and not to aspirate the blood sample which is determined to have been coagulated. However, the invention is not limited to this. For all the blood samples for which measuring orders are obtained, the system control apparatuses 7 and 470 generate measuring order information, and for the blood sample which is determined to have been coagulated, the system control apparatuses generates measuring order information including data for instructing prohibition of aspiration and transmit the measuring order information to the sample transport apparatuses 3 and 330. Moreover, the sample transport apparatuses 3 and 330 are configured to transmit aspiration instruction data to the blood cell analyzing apparatus 5 or the smear preparing apparatus 6 in the case of the blood sample for which measuring order information does not include data for instructing prohibition of aspiration, and not to transmit aspiration instruction data to the blood cell analyzing apparatus 5 or the smear preparing apparatus 6 in the case of the blood sample for which measuring order information includes data for instructing prohibition of aspiration. Due to this configuration, the sample dispensing section 511 may be controlled to aspirate the blood sample which is determined not to have been coagulated and not to aspirate the blood sample which is determined to have been coagulated.

In the above-described first, third and fourth embodiments, the configuration, in which the system control apparatuses 7 and 470 generate measuring order information and the controllers 31c and 331c of the sample transport apparatuses 3 and 330 provided separately from the system control apparatuses 7 and 470 issue aspiration instruction data, has been described. However, the invention is not limited to this. A configuration, in which the generation of measuring order information and the issue of aspiration instruction data are performed by one CPU, may be employed. A configuration, in which without generating measuring order information, one CPU issues aspiration instruction data for a blood sample which is determined not to have been coagulated and does not issue aspiration instruction data for a blood sample which is determined to have been coagulated, also may be employed.

In the above-described first, third and fourth embodiments, the configuration, in which the controllers 31c and 331c of the sample transport apparatuses 3 and 330 issue aspiration instruction data and controls the transport operation of the sample rack 9, has been described. However, the invention is not limited to this. A configuration, in which a CPU (for example, the CPU 71a of the system control apparatuses 7 and 470 or a CPU of the computer provided separately from this) provided separately from the controllers 31c and 331c issues aspiration instruction data and controls the transport operation of the sample rack 9, also may be employed.

In addition, a configuration, in which the sample transport apparatuses 3 and 330 transmit aspiration instruction data to the blood cell analyzing apparatus 5 or the smear preparing apparatus 6 in the case of the blood sample in which blood coagulation does not occur and transmits aspiration prohibition data to the blood cell analyzing apparatus 5 or the smear preparing apparatus 6 in the case of the blood sample in which blood coagulation occurs, and the blood sample is aspirated when the measuring unit 51 receives the aspiration instruction data and the aspiration is not performed when the measuring unit receives the aspiration prohibition data, may be employed.

In the above-described first to fourth embodiments, the configuration, in which the sample container 8 is held in a state in which the bottom portion of the sample container 8 is positioned higher than the lid 8a, and an image obtained by imaging the sample container 8 in this state is processed to determine blood coagulation, has been described. However, the invention is not limited to this. A configuration, in which the sample container 8 is held in a state in which the bottom portion of the sample container 8 and the lid 8a are the same in height, and an image obtained by imaging the sample container 8 in this state is processed to determine blood coagulation, also may be employed.

In the above-described first to fourth embodiments, the configuration, in which a position of an image of a blood surface is detected using the B luminance accumulation value in the processing area 113 of an image obtained by imaging a tilted sample container, has been described. However, the invention is not limited to this. If the position of the image of the liquid surface can be detected by an image process, the image of the liquid surface may be detected using any method. For example, since an image of a liquid surface to be detected corresponds to a horizontal portion of the liquid surface, the image is linear. Accordingly, the image obtained by imaging the tilted sample container is binarized to obtain the binarized image having a blood portion and the other portion as different values and a linear portion of a border between an area of "0" and an area of "1" of the binarized image may be detected as a position of the image of the liquid surface.

In the above-described first to fourth embodiments, the configuration, in which blood coagulation is determined by subjecting an image process to an image of the processing area 114 positioned higher than the position of the image of the blood surface, has been described. However, the invention is not limited to this. A configuration, in which an image obtained by imaging a tilted sample container is binarized to obtain the binarized image having a blood portion and the other portion as different values, a border between an area of "0" and an area of "1" of the binarized image is detected, and on the basis of a position (height of the liquid surface) of a linear portion of the border, a portion protruding upward from the linear portion, that is, a portion of a clot exists in the border, may be employed.

In the above-described first to fourth embodiments, the configuration, in which the number of pixels of which the B value is equal to or less than a predetermined value and the R/B luminance ratio is equal to or less than a predetermined value is counted in all the pixels included in the processing area 114 positioned higher than an image of a liquid surface of a blood sample to determine blood is coagulated when the number of pixels is equal to or greater than a predetermined value and to determine blood is not coagulated when the number of pixels are less than the predetermined value, has been described. However, the invention is not limited to this. A configuration, in which an image of the processing area 114 is binarized so that a blood portion is set to, for example "0" and the other portion is set to, for example "1", and an area of the blood portion obtained as described above is compared with a predetermined reference value to determine that blood is coagulated when the area is equal to or greater than a reference value and determine that blood is not coagulated when the area is less than the reference value, may be employed.

In the above-described first to fourth embodiments, the configuration, in which an image process is performed using a value related to the B value of the R/B luminance ratio, the R/B accumulation luminance ratio, the B luminance accumulation value and the B value to perform blood volume detection and determination of blood coagulation, has been described. However, the invention is not limited to this. A G value may be used in place of the B value.

In the above-described first embodiment, the configuration, in which the blood sample analyzing system 1 is provided with the blood cell analyzing apparatus 5 and the smear preparing apparatus 6, has been described. However, the invention is not limited to this. In place of the blood cell analyzing apparatus 5 and the smear preparing apparatus 6, other blood analyzing apparatuses such as a blood coagulation measuring apparatus, an immunity analyzing apparatus and a biochemical analyzing apparatus may be provided. Moreover, the blood sample analyzing system may be configured to include one sample analyzing apparatus or may be configured to include an arbitrary number of the sample analyzing apparatuses among the sample analyzing apparatuses.

In the above-described first to fourth embodiments, the configuration, in which the computer executes the blood volume detecting process and the blood coagulation determining process of the image processing program and thus the computer which is operated as the system control apparatus 7 and the information processing unit 270 detects a blood volume in a sample container and determines whether a blood sample in the sample container is coagulated, has been described. However, the invention is not limited to this. A configuration, in which the blood volume detecting process and the blood coagulation determining process can be executed by a dedicated hardware such as FPGA or ASIC which can execute the same process as the image processing program, may be employed.

In the above-described first embodiment, the configuration, in which the blood volume detecting process and the blood coagulation determining process are executed by the system control apparatus 7 provided independently from the sample check unit 22, has been described. However, the invention is not limited to this. A configuration, in which the blood volume detecting process and the blood coagulation determining process are performed by an image processing section composed of a CPU and the like and incorporated in the sample check unit 22 provided with the cameras 225a and 225b, also may be employed. A configuration, in which the system control apparatus 7 receiving a measuring order and transmitting the measuring order to the sample transport apparatus 3 does not perform the blood volume detecting process and the blood coagulation determining process and a dedicated image processing apparatus for executing the blood volume detecting process and the blood coagulation determining process is provided separately from the system control apparatus 7, also may be employed.

In the above-described first embodiment, the configuration, in which the single computer 7a performs all the processes of the system control program 74a, has been described. However, the invention is not limited to this. A distribution system for distributing the same process as the above-described system control program 74a to plural apparatuses (computers) and executing the process also can be employed.

What is claimed is:

1. A blood sample coagulation determining apparatus, comprising:
    a sample container holder capable of holding a sample container, the sample container having translucency and containing a blood sample, where a top opening of the sample container is sealed by a lid;
    an imaging part for imaging the sample container held by the sample container holder in a state that the bottom portion of the sample container is positioned at the same height as the lid or higher than the lid in a first direction, the imaging part operable to output a sample container image that defines the vicinity of the bottom portion of the sample container to identify a position of a blood clot relative to a liquid surface of the blood sample in the sample container; and
    a system control apparatus comprising a CPU and a memory and executing, by the CPU, instructions which process the sample container image and determine whether the blood sample in the sample container is coagulated, based on the presence or absence of a clot protruding from a liquid surface of the blood sample contained in the sample container by using the sample container image.

2. The blood sample coagulation determining apparatus of claim 1, wherein the sample container image further comprises an image of an area positioned higher than the liquid surface of the blood sample in the sample container.

3. The blood sample coagulation determining apparatus of claim 2, wherein
    the container image includes information related to a red color component for each pixel; and
    the system control apparatus further executes by the CPU instructions comprising the step of determining that the blood sample in the sample container is coagulated, based on the information about the red color component of each of pixels included in the image of the area positioned higher than the liquid surface.

4. The blood sample coagulation determining apparatus of claim 3, wherein the system control apparatus further executes by the CPU instructions comprising the steps of:
    counting a number of pixels satisfying a predetermined condition related to the red color component among the pixels included in the image of the area positioned higher than the liquid surface, and
    determining that the blood sample in the sample container is coagulated based on a count result.

5. The blood sample coagulation determining apparatus of claim 1, wherein the system control apparatus further executes by the CPU instructions comprising the steps of:
    detecting a position or height of the liquid surface in the sample container image, and
    determining that the blood sample in the sample container is coagulated based on the image of the clot positioned higher than the detected position or height of the liquid surface.

6. The blood sample coagulation determining apparatus of claim 5, wherein
    the system control apparatus further executes, by the CPU, instructions comprising the step of detecting the position or height of the liquid surface in the sample container image, based on a change in information related to the red color component in the second direction in the sample container image.

7. The blood sample coagulation determining apparatus of claim 5, wherein the system control apparatus further executes, by the CPU, instructions comprising the steps of:
    detecting a position of the bottom portion of the sample container from a background image in the sample container image,
    setting a first processing target area based on the detected position of the bottom portion of the sample container in the sample container image, wherein the first processing target area encompasses an image area where the clot is most likely present due to weight of the clot,
    setting a second processing target area in the sample container image which is located adjacent to the first processing target area in the first direction, wherein liquid blood is present in the second processing target area; and
    detecting the position or height of the liquid surface based on an image of the second processing target area.

8. The blood sample coagulation determining apparatus of claim 7, wherein the system control apparatus further executes by the CPU, instructions comprising the steps of:
    determining whether the position or height of the liquid surface is detected;
    upon determination that the position or height of the liquid surface is undetectable, determining that the blood sample in the sample container is coagulated based on the first processing target area.

9. The blood sample coagulation determining apparatus of claim 1, further comprising an illuminator for irradiating the sample container held by the sample container holder,
wherein the imaging part is positioned at a position in which the imaging part does not directly receive light reflected from the sample container which is irradiated by the illuminator.

10. The blood sample coagulation determining apparatus of claim 1, wherein imaging part images the sample container held by the sample container holder in a state that the bottom portion of the sample container is positioned higher than the lid in the first direction.

11. A blood sample coagulation determining method, comprising steps of:
holding a sample container having translucency and containing a blood sample, where a top opening of the sample container is sealed by a lid, in a tilted state that a bottom portion of the sample container is positioned at the same height as the lid or higher than the lid in a horizontal direction;
imaging the sample container held in the titled state and outputting a container image that defines the vicinity of the bottom portion of the sample container in the tilted state to identify a position of a blood clot relative to a liquid surface of the blood sample in the sample container; and
determining whether the blood sample in the sample container is coagulated, based on the presence or absence of a clot protruding from a liquid surface of the blood sample in the sample container in a vertical direction which intersects with the horizontal direction by using the container image.

12. The method of claim 11, wherein the step of determining further comprises determining whether the liquid surface is identifiable based on the container image.

13. The method of claim 12, wherein upon determination that the liquid surface is unidentifiable, determining whether the blood sample in the same container is coagulated based on the count result in the coagulation check range, wherein the count result is the larger than a count result in the coagulation check range when the liquid surface is identifiable.

14. The method of claim 11, wherein the step of determining is performed based on information about a red color component of each of pixels included in the container image of an area positioned higher than the liquid surface.

15. The method of claim 14, wherein the step of determining further comprises detecting a position or height of the liquid surface in the container image, based on a change in the information related to the red color component in the vertical direction in the container image.

16. The method of claim 15, wherein the step of determining comprises:
counting a number of pixels satisfying a predetermined condition related to the red color component among the pixels included in the container image of the area positioned higher than the liquid surface; and
determining that the blood sample in the sample container is coagulated based on a count result.

* * * * *